United States Patent
Rabuka et al.

(10) Patent No.: US 11,980,668 B2
(45) Date of Patent: May 14, 2024

(54) SULFATASE-CLEAVABLE LINKERS FOR ANTIBODY-DRUG CONJUGATES

(71) Applicant: R.P. Scherer Technologies, LLC, Carson City, NV (US)

(72) Inventors: David Rabuka, Kensington, CA (US); Junjie Liu, San Diego, CA (US); Stepan Chuprakov, Emeryville, CA (US); Romas Alvydas Kudirka, Redwood City, CA (US)

(73) Assignee: R.P. Scherer Technologies, LLC, Carson City, NV (US)

(*) Notice: Subject to any disclaimer, the term of this patent is extended or adjusted under 35 U.S.C. 154(b) by 518 days.

(21) Appl. No.: 17/287,792

(22) PCT Filed: Oct. 23, 2019

(86) PCT No.: PCT/US2019/057626
§ 371 (c)(1),
(2) Date: Apr. 22, 2021

(87) PCT Pub. No.: WO2020/096775
PCT Pub. Date: May 14, 2020

(65) Prior Publication Data
US 2021/0393789 A1    Dec. 23, 2021

Related U.S. Application Data

(60) Provisional application No. 62/758,356, filed on Nov. 9, 2018.

(51) Int. Cl.
*A61K 47/68* (2017.01)
*A61K 38/07* (2006.01)

(52) U.S. Cl.
CPC .......... *A61K 47/6803* (2017.08); *A61K 38/07* (2013.01); *A61K 47/6849* (2017.08); *A61K 47/6851* (2017.08); *A61K 47/6889* (2017.08)

(58) Field of Classification Search
None
See application file for complete search history.

(56) References Cited

U.S. PATENT DOCUMENTS

| | | |
|---|---|---|
| 9,310,374 B2 | 4/2016 | Kudirka et al. |
| 9,493,413 B2 | 11/2016 | Rabuka et al. |
| 2017/0044191 A1 | 2/2017 | Smaill et al. |

FOREIGN PATENT DOCUMENTS

| | | |
|---|---|---|
| WO | WO 2001/36003 | 5/2001 |
| WO | WO 2018/096504 | 5/2018 |
| WO | WO 2018/102726 | 6/2018 |

*Primary Examiner* — Karl J Puttlitz
(74) *Attorney, Agent, or Firm* — Rudy J. Ng; Bozicevic, Field & Francis LLP

(57) ABSTRACT

The present disclosure provides antibody-drug conjugate structures, that include a cleavable linker having a sulfatase-cleavable moiety. The disclosure also encompasses methods of production of such conjugates, as well as methods of using the same.

15 Claims, 5 Drawing Sheets

Specification includes a Sequence Listing.

SEQUENCE LISTING

<160> NUMBER OF SEQ ID NOS: 29

<210> SEQ ID NO 1
<211> LENGTH: 6
<212> TYPE: PRT
<213> ORGANISM: Artificial sequence
<220> FEATURE:
<223> OTHER INFORMATION: synthetic sequence

<400> SEQUENCE: 1

Leu Cys Thr Pro Ser Arg
1               5

<210> SEQ ID NO 2
<211> LENGTH: 6
<212> TYPE: PRT
<213> ORGANISM: Artificial sequence
<220> FEATURE:
<223> OTHER INFORMATION: synthetic sequence

<400> SEQUENCE: 2

Met Cys Thr Pro Ser Arg
1               5

<210> SEQ ID NO 3
<211> LENGTH: 6
<212> TYPE: PRT
<213> ORGANISM: Artificial sequence
<220> FEATURE:
<223> OTHER INFORMATION: synthetic sequence

<400> SEQUENCE: 3

Val Cys Thr Pro Ser Arg
1               5

```
<210> SEQ ID NO 4
<211> LENGTH: 6
<212> TYPE: PRT
<213> ORGANISM: Artificial sequence
<220> FEATURE:
<223> OTHER INFORMATION: synthetic sequence

<400> SEQUENCE: 4

Leu Cys Ser Pro Ser Arg
1               5

<210> SEQ ID NO 5
<211> LENGTH: 6
<212> TYPE: PRT
<213> ORGANISM: Artificial sequence
<220> FEATURE:
<223> OTHER INFORMATION: synthetic sequence

<400> SEQUENCE: 5

Leu Cys Ala Pro Ser Arg
1               5

<210> SEQ ID NO 6
<211> LENGTH: 6
<212> TYPE: PRT
<213> ORGANISM: Artificial sequence
<220> FEATURE:
<223> OTHER INFORMATION: synthetic sequence

<400> SEQUENCE: 6

Leu Cys Val Pro Ser Arg
1               5

<210> SEQ ID NO 7
<211> LENGTH: 6
<212> TYPE: PRT
<213> ORGANISM: Artificial sequence
<220> FEATURE:
<223> OTHER INFORMATION: synthetic sequence

<400> SEQUENCE: 7

Leu Cys Gly Pro Ser Arg
1               5

<210> SEQ ID NO 8
<211> LENGTH: 6
<212> TYPE: PRT
<213> ORGANISM: Artificial sequence
<220> FEATURE:
<223> OTHER INFORMATION: synthetic sequence

<400> SEQUENCE: 8

Ile Cys Thr Pro Ala Arg
1               5

<210> SEQ ID NO 9
<211> LENGTH: 6
<212> TYPE: PRT
<213> ORGANISM: Artificial sequence
<220> FEATURE:
<223> OTHER INFORMATION: synthetic sequence

<400> SEQUENCE: 9

Leu Cys Thr Pro Ser Lys
1               5
```

```
<210> SEQ ID NO 10
<211> LENGTH: 6
<212> TYPE: PRT
<213> ORGANISM: Artificial sequence
<220> FEATURE:
<223> OTHER INFORMATION: synthetic sequence

<400> SEQUENCE: 10

Met Cys Thr Pro Ser Lys
1               5

<210> SEQ ID NO 11
<211> LENGTH: 6
<212> TYPE: PRT
<213> ORGANISM: Artificial sequence
<220> FEATURE:
<223> OTHER INFORMATION: synthetic sequence

<400> SEQUENCE: 11

Val Cys Thr Pro Ser Lys
1               5

<210> SEQ ID NO 12
<211> LENGTH: 6
<212> TYPE: PRT
<213> ORGANISM: Artificial sequence
<220> FEATURE:
<223> OTHER INFORMATION: synthetic sequence

<400> SEQUENCE: 12

Leu Cys Ser Pro Ser Lys
1               5

<210> SEQ ID NO 13
<211> LENGTH: 6
<212> TYPE: PRT
<213> ORGANISM: Artificial sequence
<220> FEATURE:
<223> OTHER INFORMATION: synthetic sequence

<400> SEQUENCE: 13

Leu Cys Ala Pro Ser Lys
1               5

<210> SEQ ID NO 14
<211> LENGTH: 6
<212> TYPE: PRT
<213> ORGANISM: Artificial sequence
<220> FEATURE:
<223> OTHER INFORMATION: synthetic sequence

<400> SEQUENCE: 14

Leu Cys Val Pro Ser Lys
1               5

<210> SEQ ID NO 15
<211> LENGTH: 6
<212> TYPE: PRT
<213> ORGANISM: Artificial sequence
<220> FEATURE:
<223> OTHER INFORMATION: synthetic sequence

<400> SEQUENCE: 15

Leu Cys Gly Pro Ser Lys
1               5
```

```
<210> SEQ ID NO 16
<211> LENGTH: 6
<212> TYPE: PRT
<213> ORGANISM: Artificial sequence
<220> FEATURE:
<223> OTHER INFORMATION: synthetic sequence

<400> SEQUENCE: 16

Leu Cys Thr Pro Ser Ala
1               5

<210> SEQ ID NO 17
<211> LENGTH: 6
<212> TYPE: PRT
<213> ORGANISM: Artificial sequence
<220> FEATURE:
<223> OTHER INFORMATION: synthetic sequence

<400> SEQUENCE: 17

Ile Cys Thr Pro Ala Ala
1               5

<210> SEQ ID NO 18
<211> LENGTH: 6
<212> TYPE: PRT
<213> ORGANISM: Artificial sequence
<220> FEATURE:
<223> OTHER INFORMATION: synthetic sequence

<400> SEQUENCE: 18

Met Cys Thr Pro Ser Ala
1               5

<210> SEQ ID NO 19
<211> LENGTH: 6
<212> TYPE: PRT
<213> ORGANISM: Artificial sequence
<220> FEATURE:
<223> OTHER INFORMATION: synthetic sequence

<400> SEQUENCE: 19

Val Cys Thr Pro Ser Ala
1               5

<210> SEQ ID NO 20
<211> LENGTH: 6
<212> TYPE: PRT
<213> ORGANISM: Artificial sequence
<220> FEATURE:
<223> OTHER INFORMATION: synthetic sequence

<400> SEQUENCE: 20

Leu Cys Ser Pro Ser Ala
1               5

<210> SEQ ID NO 21
<211> LENGTH: 6
<212> TYPE: PRT
<213> ORGANISM: Artificial sequence
<220> FEATURE:
<223> OTHER INFORMATION: synthetic sequence

<400> SEQUENCE: 21

Leu Cys Ala Pro Ser Ala
1               5

<210> SEQ ID NO 22
```

```
<211> LENGTH: 6
<212> TYPE: PRT
<213> ORGANISM: Artificial sequence
<220> FEATURE:
<223> OTHER INFORMATION: synthetic sequence

<400> SEQUENCE: 22

Leu Cys Val Pro Ser Ala
1               5

<210> SEQ ID NO 23
<211> LENGTH: 6
<212> TYPE: PRT
<213> ORGANISM: Artificial sequence
<220> FEATURE:
<223> OTHER INFORMATION: synthetic sequence

<400> SEQUENCE: 23

Leu Cys Gly Pro Ser Ala
1               5

<210> SEQ ID NO 24
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (2)..(2)
<223> OTHER INFORMATION: Xaa is Cys or Ser

<400> SEQUENCE: 24

Leu Xaa Thr Pro Ser Arg
1               5

<210> SEQ ID NO 25
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (2)..(2)
<223> OTHER INFORMATION: Xaa at position 2 is 2-formylglycine

<400> SEQUENCE: 25

Leu Xaa Thr Pro Ser Arg
1               5

<210> SEQ ID NO 26
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is present or absent and, when present, can
      be any amino acid
<220> FEATURE:
<221> NAME/KEY: MISC_FEATURE
<222> LOCATION: (2)..(2)
<223> OTHER INFORMATION: Xaa is cysteine or serine
<220> FEATURE:
<221> NAME/KEY: MISC_FEATURE
<222> LOCATION: (3)..(3)
<223> OTHER INFORMATION: Xaa can be any amino acid, though usually an
      aliphatic amino acid, a polar, uncharged amino acid, or a sulfur
```

```
       containing amino acid (i.e., other than an aromatic amino acid or
       a charged amino acid), e.g., S, T, A, V, G or C, e.g., S, T, A, V
       or G
<220> FEATURE:
<221> NAME/KEY: MISC_FEATURE
<222> LOCATION: (4)..(4)
<223> OTHER INFORMATION: Xaa is proline or alanine
<220> FEATURE:
<221> NAME/KEY: MISC_FEATURE
<222> LOCATION: (5)..(5)
<223> OTHER INFORMATION: Xaa can be any amino acid, though usually an
       aliphatic amino acid, a polar, uncharged amino acid, or a sulfur
       containing amino acid (i.e., other than an aromatic amino acid or
       a charged amino acid), e.g., S, T, A, V, G or C, e.g., S, T, A, V
       or G
<220> FEATURE:
<221> NAME/KEY: MISC_FEATURE
<222> LOCATION: (6)..(6)
<223> OTHER INFORMATION: Xaa is a basic amino acid (e.g., arginine (R),
       and may be lysine (K) or histidine (H), e.g., lysine), or an
       aliphatic amino acid (alanine (A), glycine (G), leucine (L),
       valine (V), isoleucine (I), or proline (P), e.g., A, G, L, V, or I

<400> SEQUENCE: 26

Xaa Xaa Xaa Xaa Xaa Xaa
1               5

<210> SEQ ID NO 27
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa may be present or absent and, when present,
      can be any amino acid
<220> FEATURE:
<221> NAME/KEY: MISC_FEATURE
<222> LOCATION: (3)..(3)
<223> OTHER INFORMATION: Xaa can be any amino acid, e.g., an aliphatic
      amino acid, a sulfur-containing amino acid, or a polar, uncharged
      amino acid, (i.e., other than an aromatic amino acid or a charged
      amino acid), e.g., S, T, A, V, G, or C, e.g., S, T, A, V or G
<220> FEATURE:
<221> NAME/KEY: MISC_FEATURE
<222> LOCATION: (5)..(5)
<223> OTHER INFORMATION: Xaa can be any amino acid, e.g., an aliphatic
      amino acid, a sulfur-containing amino acid, or a polar, uncharged
      amino acid, (i.e., other than an aromatic amino acid or a charged
      amino acid), e.g., S, T, A, V, G, or C, e.g., S, T, A, V or G
<220> FEATURE:
<221> NAME/KEY: MISC_FEATURE
<222> LOCATION: (6)..(6)
<223> OTHER INFORMATION: Xaa is a basic amino acid (e.g., arginine (R),
      and may be lysine (K) or histidine (H), e.g., lysine), or an
      aliphatic amino acid (alanine (A), glycine (G), leucine (L),
      valine (V), isoleucine (I), or proline (P), e.g., A, G, L, V, or I

<400> SEQUENCE: 27

Xaa Cys Xaa Pro Xaa Xaa
1               5

<210> SEQ ID NO 28
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa may be present or absent and, when present,
      can be any amino acid
```

```
<220> FEATURE:
<221> NAME/KEY: MOD_RES
<222> LOCATION: (2)..(2)
<223> OTHER INFORMATION: Xaa is formylglycine
<220> FEATURE:
<221> NAME/KEY: MISC_FEATURE
<222> LOCATION: (3)..(3)
<223> OTHER INFORMATION: Xaa can be any amino acid, e.g., an aliphatic
      amino acid, a sulfur-containing amino acid, or a polar, uncharged
      amino acid, (i.e., other than an aromatic amino acid or a charged
      amino acid), e.g., S, T, A, V, G or C, e.g., S, T, A, V or G
<220> FEATURE:
<221> NAME/KEY: MISC_FEATURE
<222> LOCATION: (4)..(4)
<223> OTHER INFORMATION: Xaa is either proline or alanine
<220> FEATURE:
<221> NAME/KEY: MISC_FEATURE
<222> LOCATION: (5)..(5)
<223> OTHER INFORMATION: Xaa can be any amino acid, e.g., an aliphatic
      amino acid, a sulfur-containing amino acid, or a polar, uncharged
      amino acid, (i.e., other than an aromatic amino acid or a charged
      amino acid), e.g., S, T, A, V, G or C, e.g., S, T, A, V or G
<220> FEATURE:
<221> NAME/KEY: MISC_FEATURE
<222> LOCATION: (6)..(6)
<223> OTHER INFORMATION: Xaa is a basic amino acid (e.g., arginine (R),
      and may be lysine (K) or histidine (H), usually lysine), or an
      aliphatic amino acid (alanine (A), glycine (G), leucine (L),
      valine (V), isoleucine (I), or proline (P), e.g., A,G,L,V, or I

<400> SEQUENCE: 28

Xaa Xaa Xaa Xaa Xaa Xaa
1               5

<210> SEQ ID NO 29
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa may be present or absent and, when present,
      can be any amino acid
<220> FEATURE:
<221> NAME/KEY: MOD_RES
<222> LOCATION: (2)..(2)
<223> OTHER INFORMATION: Xaa is FGly'
<220> FEATURE:
<221> NAME/KEY: MISC_FEATURE
<222> LOCATION: (3)..(3)
<223> OTHER INFORMATION: Xaa can be any amino acid, e.g., an aliphatic
      amino acid, a sulfur-containing amino acid, or a polar, uncharged
      amino acid, (i.e., other than an aromatic amino acid or a charged
      amino acid), e.g., S, T, A, V, G or C, e.g., S, T, A, V or G.
<220> FEATURE:
<221> NAME/KEY: MISC_FEATURE
<222> LOCATION: (4)..(4)
<223> OTHER INFORMATION: Xaa is proline or alanine
<220> FEATURE:
<221> NAME/KEY: MISC_FEATURE
<222> LOCATION: (5)..(5)
<223> OTHER INFORMATION: Xaa can be any amino acid, e.g., an aliphatic
      amino acid, a sulfur-containing amino acid, or a polar, uncharged
      amino acid, (i.e., other than an aromatic amino acid or a charged
      amino acid), e.g., S, T, A, V, G or C, e.g., S, T, A, V or G.
<220> FEATURE:
<221> NAME/KEY: MISC_FEATURE
```

```
<222> LOCATION: (6)..(6)
<223> OTHER INFORMATION: Xaa is a basic amino acid (e.g., arginine (R),
      and may be lysine (K) or histidine (H), usually lysine), or an
      aliphatic amino acid (alanine (A), glycine (G), leucine (L),
      valine (V), isoleucine (I), or proline (P), e.g., A, G, L, V, or I

<400> SEQUENCE: 29

Xaa Xaa Xaa Xaa Xaa Xaa
1               5
```

SULFATASE-CLEAVABLE LINKERS FOR ANTIBODY-DRUG CONJUGATES

CROSS-REFERENCE TO RELATED APPLICATIONS

This application claims the benefit of U.S. Provisional Application No. 62/758,356, filed Nov. 9, 2018, the disclosure of which is incorporated herein by reference in its entirety.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects. Chemical modification of proteins may extend these advantages by rendering them more potent, stable, or multimodal.

SUMMARY

Sulfate esters have hydrolytic stabilities while the cleavage by sulfatases is very efficient. The majority of sulfatases exist in the lysosome, which may facilitate the use of sulfatase activity as an enzymatic cleavable modality for antibody-drug conjugate (ADC) payload release.

The present disclosure provides antibody-drug conjugate structures, that include a cleavable linker having a sulfatase-cleavable moiety. The disclosure also encompasses methods of production of such conjugates, as well as methods of using the same.

Aspects of the present disclosure include a conjugate that includes an antibody, a drug, and cleavable linker that links the antibody to the drug and comprises a sulfatase-cleavable moiety.

In some embodiments, the sulfatase-cleavable moiety includes a sulfate-containing group. In some embodiments, the sulfate-containing group includes an aryl sulfonic acid or an aryl sulfate ester. In some embodiments, the sulfate-containing group includes an amino-benzyloxycarbonyl group substituted with an aryl sulfonic acid or an aryl sulfate ester. For example, the amino-benzyloxycarbonyl group can be a meta-amino-benzyloxycarbonyl group substituted with an aryl sulfonic acid or an aryl sulfate ester, or an ortho-amino-benzyloxycarbonyl group substituted with an aryl sulfonic acid or an aryl sulfate ester, or a para-amino-benzyloxycarbonyl group substituted with an aryl sulfonic acid or an aryl sulfate ester.

In some embodiments, the conjugate is of formula (I):

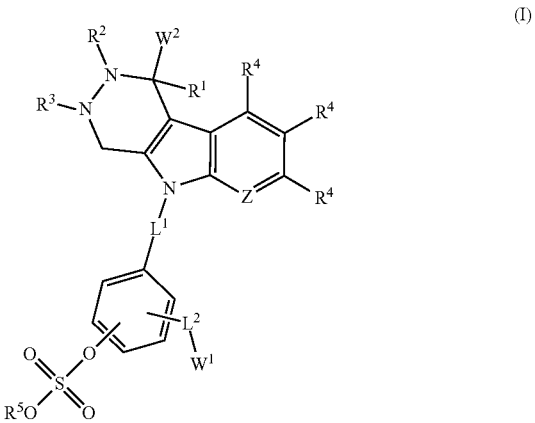

wherein

Z is $CR^4$ or N;

$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$R^5$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$L^1$ is a first linker;

$L^2$ is a second linker;

$W^1$ is the drug; and $W^2$ is the antibody.

In some embodiments, the conjugate is of formula (Ia):

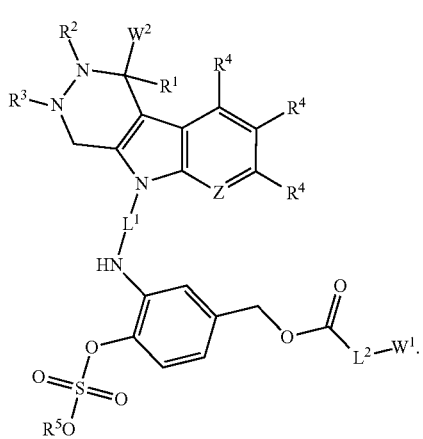

(Ia)

In some embodiments, the conjugate is of formula (Ib):

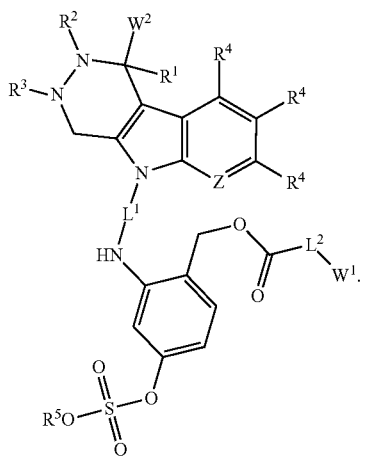

(Ib)

In some embodiments, the conjugate is of formula (Ic):

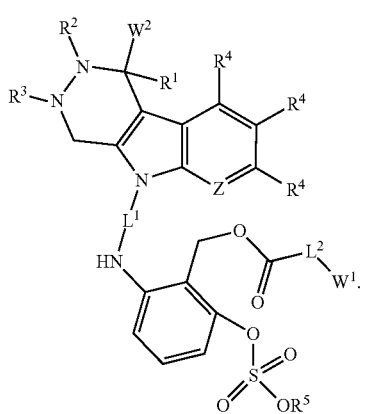

(Ic)

In some embodiments, the conjugate is of formula (Id):

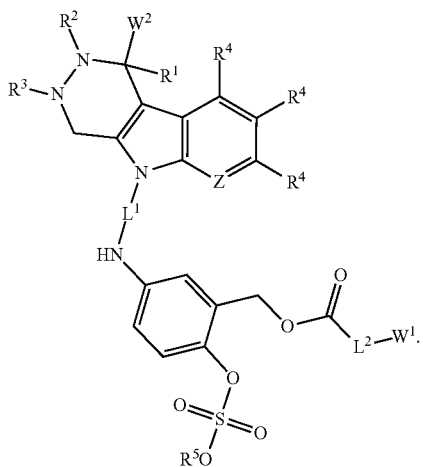

(Id)

In some embodiments, the conjugate is of formula (Ie):

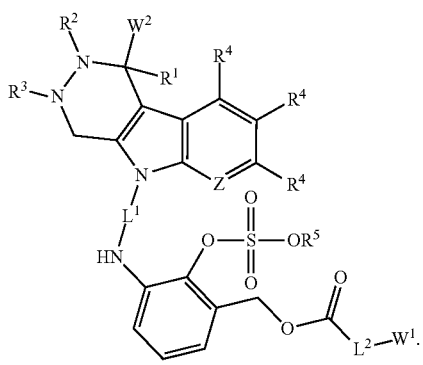

(Ie)

In some embodiments, $L^1$ includes:

-$(T^1-V^1)_a$-$(T^2-V^2)_b$-$(T^3-V^3)_c$-$(T^4-V^4)_d$-, wherein
a, b, c and d are each independently 0 or 1;
$T^1$, $T^2$, $T^3$ and $T^4$ are each independently selected from $(C_1-C_{12})$alkyl, substituted $(C_1-C_{12})$alkyl, (EDA)$_w$, (PEG)$_n$, (AA)$_p$, —(CR$^{13}$OH)$_m$—, piperidin-4-amino (4AP), an acetal group, a hydrazine, a disulfide, and an ester, wherein EDA is an ethylene diamine moiety, PEG is a polyethylene glycol, and AA is an amino acid residue, wherein each w is an integer from 1 to 20, each n is an integer from 1 to 30, each p is an integer from 1 to 20, and each m is an integer from 1 to 12;
$V^1$, $V^2$, $V^3$ and $V^4$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein each q is an integer from 1 to 6;
each $R^{13}$ is independently selected from hydrogen, an alkyl, a substituted alkyl, an aryl, and a substituted aryl; and
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, $L^2$ includes:

$$-(T^5-V^5)_e-(T^6-V^6)_f-(T^7-V^7)_g-(T^8-V^8)_h-,$$

wherein e, f, g and h are each independently 0 or 1;

$T^5$, $T^6$, $T^7$ and $T^8$ are each independently selected from $(C_1-C_{12})$alkyl, substituted $(C_1-C_{12})$alkyl, $(EDA)_w$, $(PEG)_n$, $(AA)_p$, $-(CR^{13}OH)_m-$, piperidin-4-amino (4AP), an acetal group, a hydrazine, a disulfide, and an ester, wherein EDA is an ethylene diamine moiety, PEG is a polyethylene glycol, and AA is an amino acid residue, wherein each w is an integer from 1 to 20, each n is an integer from 1 to 30, each p is an integer from 1 to 20, and each m is an integer from 1 to 12;

$V^5$, $V^6$, $V^7$ and $V^8$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$ and $-P(O)OH-$, wherein each q is an integer from 1 to 6;

each $R^{13}$ is independently selected from hydrogen, an alkyl, a substituted alkyl, an aryl, and a substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments:

$T^1$ is selected from a $(C_1-C_{12})$alkyl and a substituted $(C_1-C_{12})$alkyl;

$T^2$, $T^3$, and $T^4$ are each independently selected from $(EDA)_w$, $(PEG)_n$, $(C_1-C_{12})$alkyl, substituted $(C_1-C_{12})$alkyl, $(AA)_p$, $-(CR^{13}OH)_m-$, 4-amino-piperidine (4AP), an acetal group, a hydrazine, and an ester; and $V^1$, $V^2$, $V^3$ and $V^4$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$, and $-P(O)OH-$;

wherein:

$(PEG)_n$ is

[structure image]

where n is an integer from 1 to 30;

EDA is an ethylene diamine moiety having the following structure:

[structure image]

where y is an integer from 1 to 6 and r is 0 or 1;

4-amino-piperidine (4AP) is

[structure image]

each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In some embodiments:

$T^1$ is $(C_1-C_{12})$alkyl and $V^1$ is $-CO-$;

$T^2$ is 4AP and $V^2$ is a covalent bond;

$T^3$ is $(PEG)_n$ and $V^3$ is $-CONR^{15}-$; and $T^4$ is $(C_1-C_{12})$alkyl and $V^4$ is $-CO-$.

In some embodiments, the drug is an auristatin. In some embodiments, the drug is a maytansine.

Aspects of the present disclosure include a compound of formula (II):

(II)

[structure image]

wherein

Z is $CR^4$ or N;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$R^5$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$L^1$ is a first linker;

$L^2$ is a second linker; and $W^1$ is a drug.

In some embodiments, the compound is of formula (IIa):

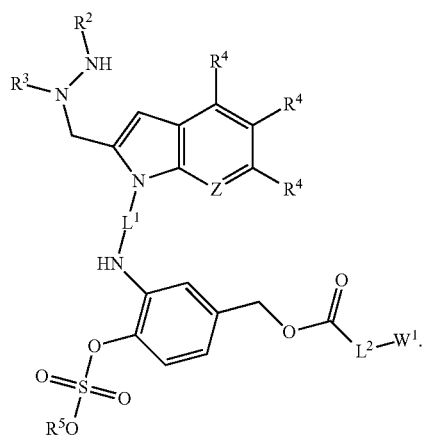

(IIa)

In some embodiments, the compound is of formula (IIb):

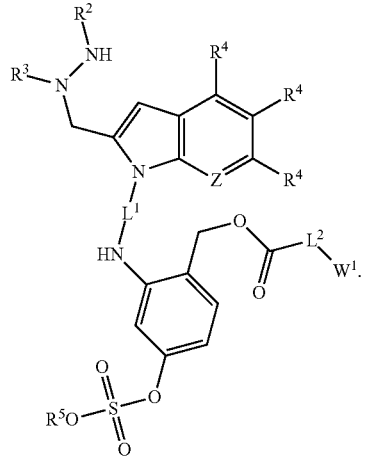

(IIb)

In some embodiments, the compound is of formula (IIc):

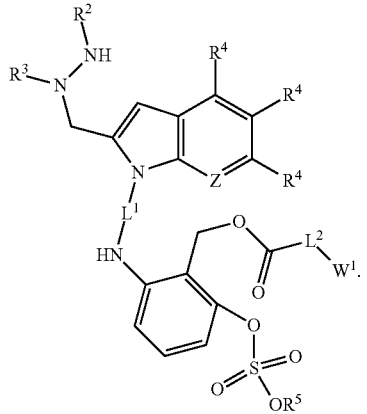

(IIc)

In some embodiments, the compound is of formula (IId):

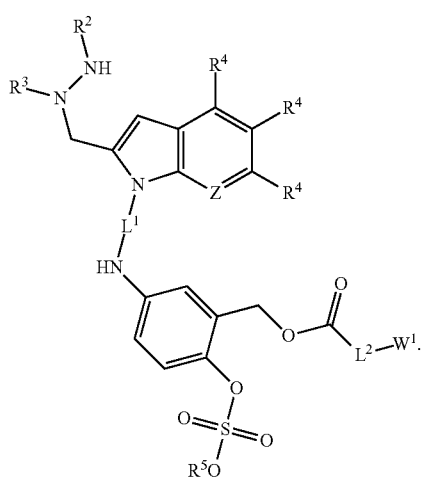

(IId)

In some embodiments, the compound is of formula (IIe):

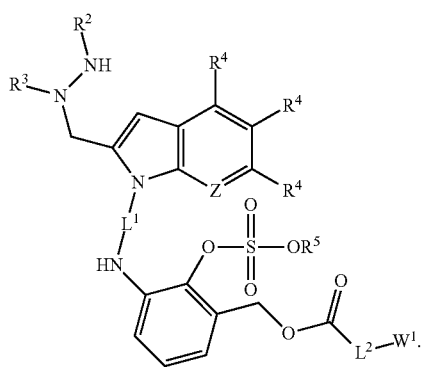

(IIe)

In some embodiments, $L^1$ includes:

$$-(T^1-V^1)_a-(T^2-V^2)_b-(T^3-V^3)_c-(T^4-V^4)_d,$$

wherein
a, b, c and d are each independently 0 or 1;
$T^1$, $T^2$, $T^3$ and $T^4$ are each independently selected from $(C_1-C_{12})$alkyl, substituted $(C_1-C_{12})$alkyl, $(EDA)_w$, $(PEG)_n$, $(AA)_p$, $—(CR^{13}OH)_m—$, piperidin-4-amino (4AP), an acetal group, a hydrazine, a disulfide, and an ester, wherein EDA is an ethylene diamine moiety, PEG is a polyethylene glycol, and AA is an amino acid residue, wherein each w is an integer from 1 to 20, each n is an integer from 1 to 30, each p is an integer from 1 to 20, and each m is an integer from 1 to 12;
$V^1$, $V^2$, $V^3$ and $V^4$ are each independently selected from the group consisting of a covalent bond, —CO—, $—NR^{15}—$, $—NR^{15}(CH_2)_q—$, $—NR^{15}(C_6H_4)—$, $—CONR^{15}—$, $—NR^{15}CO—$, —C(O)O—, —OC(O)—, —O—, —S—, —S(O)—, —$SO_2$—, —$SO_2NR^{15}$—, —$NR^{15}SO_2$— and —P(O)OH—, wherein each q is an integer from 1 to 6;
each $R^{13}$ is independently selected from hydrogen, an alkyl, a substituted alkyl, an aryl, and a substituted aryl; and
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, $L^2$ includes:

$-(T^5-V^5)_e-(T^6-V^6)_f-(T^7-V^7)_g-(T^8-V^8)_h-$, wherein
e, f, g and h are each independently 0 or 1;
$T^5$, $T^6$, $T^7$ and $T^8$ are each independently selected from $(C_1-C_{12})$alkyl, substituted $(C_1-C_{12})$alkyl, $(EDA)_w$, $(PEG)_n$, $(AA)_p$, $—(CR^{13}OH)_m—$, piperidin-4-amino (4AP), an acetal group, a hydrazine, a disulfide, and an ester, wherein EDA is an ethylene diamine moiety, PEG is a polyethylene glycol, and AA is an amino acid residue, wherein each w is an integer from 1 to 20, each n is an integer from 1 to 30, each p is an integer from 1 to 20, and each m is an integer from 1 to 12;
$V^5$, $V^6$, $V^7$ and $V^8$ are each independently selected from the group consisting of a covalent bond, —CO—, $—NR^{15}—$, $—NR^{15}(CH_2)_q—$, $—NR^{15}(C_6H_4)—$, $—CONR^{15}—$, $—NR^{15}CO—$, —C(O)O—, —OC(O)—, —O—, —S—, —S(O)—, —$SO_2$—, —$SO_2NR^{15}$—, —$NR^{15}SO_2$— and —P(O)OH—, wherein each q is an integer from 1 to 6;
each $R^{13}$ is independently selected from hydrogen, an alkyl, a substituted alkyl, an aryl, and a substituted aryl; and
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments:
$T^1$ is selected from a $(C_1-C_{12})$alkyl and a substituted $(C_1-C_{12})$alkyl;
$T^2$, $T^3$, and $T^4$ are each independently selected from $(EDA)_w$, $(PEG)_n$, $(C_1-C_{12})$alkyl, substituted $(C_1-C_{12})$alkyl, $(AA)_p$, $—(CR^{13}OH)_m—$, 4-amino-piperidine (4AP), an acetal group, a hydrazine, and an ester; and
$V^1$, $V^2$, $V^3$ and $V^4$ are each independently selected from the group consisting of a covalent bond, —CO—, $—NR^{15}—$, $—NR^{15}(CH_2)_q—$, $—NR^{15}(C_6H_4)—$, $—CONR^{15}—$, $—NR^{15}CO—$, —C(O)O—, —OC(O)—, —O—, —S—, —S(O)—, —$SO_2$—, —$SO_2NR^{15}$—, —$NR^{15}SO_2$—, and —P(O)OH—;

wherein:
$(PEG)_n$ is

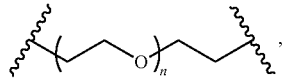

where n is an integer from 1 to 30;
EDA is an ethylene diamine moiety having the following structure:

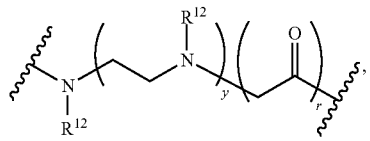

where y is an integer from 1 to 6 and r is 0 or 1;
4-amino-piperidine (4AP) is

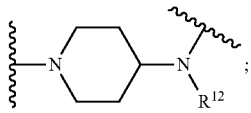

each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring; and
$R^{13}$ is selected from hydrogen, an alkyl, a substituted alkyl, an aryl, and a substituted aryl.

In some embodiments,
$T^1$ is $(C_1-C_{12})$alkyl and $V^1$ is —CO—;
$T^2$ is 4AP and $V^2$ is a covalent bond;
$T^3$ is $(PEG)_n$ and $V^3$ is $—CONR^{15}—$; and
$T^4$ is $(C_1-C_{12})$alkyl and $V^4$ is —CO—.

In some embodiments, the drug is an auristatin. In some embodiments, the drug is a maytansine.

Aspects of the present disclosure include a pharmaceutical composition, which includes a conjugate of the present disclosure, and a pharmaceutically-acceptable excipient.

Aspects of the present disclosure include a method, which includes administering to a subject an effective amount of a conjugate of the present disclosure.

Aspects of the present disclosure include a method of treating cancer in a subject, where the method includes administering to the subject a therapeutically effective amount of a pharmaceutical composition comprising a conjugate of the present disclosure, where the administering is effective to treat cancer in the subject.

DEFINITIONS

Figure 1:
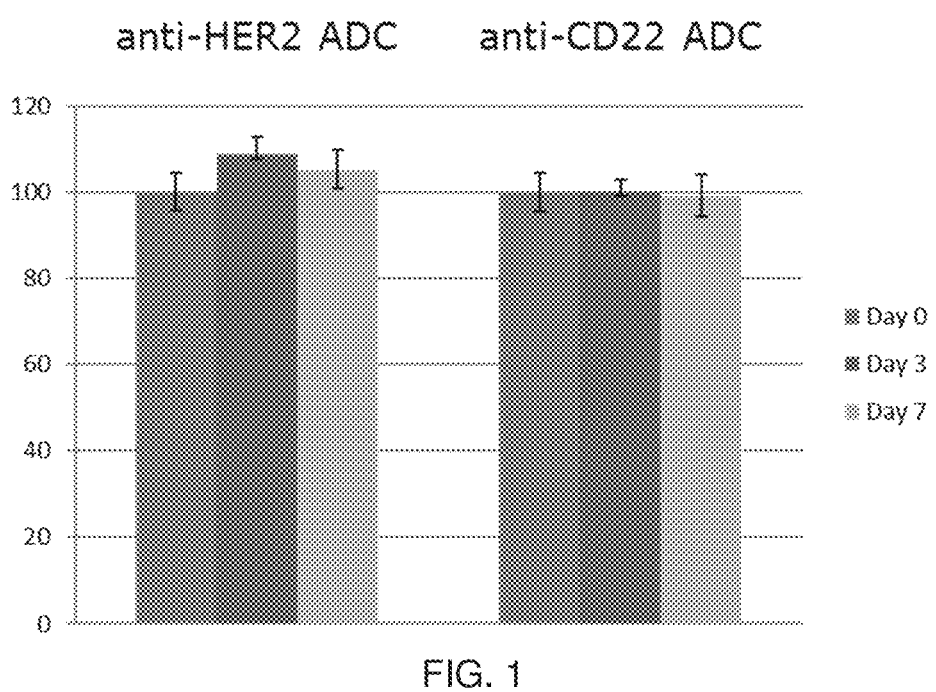
FIG. 1 shows a graph of the serum stability over time of antibody-drug conjugates (ADCs) containing a sulfatase-cleavable linker, according to embodiments of the present disclosure.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

The term "substituted alkyl" refers to an alkyl group as defined herein wherein one or more carbon atoms in the alkyl chain (except the C$_1$ carbon atom) have been optionally replaced with a heteroatom such as —O—, —N—, —S—, —S(O)$_n$—(where n is 0 to 2), —NR—(where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups-alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups-alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group-alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O) substituted alkyl, NR$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O) alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic. To satisfy valence requirements, any heteroatoms in such heteroaryl rings may or may not be bonded to H or a substituent group, e.g., an alkyl group or other substituent as described herein. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups-alkylene-heteroaryl where alkylene and heteroaryl are defined herein.

This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from nitrogen, sulfur, or oxygen, where, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$-moieties. To satisfy valence requirements, any heteroatoms in such heterocyclic rings may or may not be bonded to one or more H or one or more substituent group(s), e.g., an alkyl group or other substituent as described herein.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocloooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, and —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Sulfate" or "sulfate ester" refers the group —O—SO$_2$—OH, —O—SO$_2$—O-alkyl, —O—SO$_2$—O-substituted alkyl, —O—SO$_2$—O-alkenyl, —O—SO$_2$—O-substituted alkenyl, —O—SO$_2$—O-cycloalkyl, —O—SO$_2$—O-substituted cycloalkyl, —O—SO$_2$—O-cycloalkenyl, —O—SO$_2$—O-substituted cycloalkenyl, —O—SO$_2$—O-aryl, —O—SO$_2$—O-substituted aryl, —O—SO$_2$—O-heteroaryl, —O—SO$_2$—O-substituted heteroaryl, —O—SO$_2$—O-heterocyclic, and —O—SO$_2$—O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The terms "amino acid side chain" or "side chain of an amino acid" and the like may be used to refer to the substituent attached to the α-carbon of an amino acid residue, including natural amino acids, unnatural amino acids, and amino acid analogs. An amino acid side chain can also include an amino acid side chain as described in the context of the modified amino acids and/or conjugates described herein.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(⅘): 489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

An immunoglobulin polypeptide immunoglobulin light or heavy chain variable region is composed of a framework region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen.

A "parent Ig polypeptide" is a polypeptide comprising an amino acid sequence which lacks an aldehyde-tagged constant region as described herein. The parent polypeptide may comprise a native sequence constant region, or may comprise a constant region with pre-existing amino acid sequence modifications (such as additions, deletions and/or substitutions).

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of a sulfatase motif and Formylglycine Generating Enzyme (FGE), which react to form a reaction product of a converted aldehyde tag containing a formylglycine (FGly) in lieu of cysteine or serine in the motif. Other exemplary reactive partners include an aldehyde of an fGly residue of a converted aldehyde tag (e.g., a reactive aldehyde group) and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antibody-drug conjugate structures, that include a cleavable linker having a sulfatase-cleavable moiety. The disclosure also encompasses methods of production of such conjugates, as well as methods of using the same.

Antibody-Drug Conjugates

The present disclosure provides a conjugate, e.g., an antibody-drug conjugate (ADC). By "conjugate" is meant a first moiety (e.g., an antibody) is stably associated with a second moiety (e.g., a drug or active agent). For example, an antibody-drug conjugate includes a drug (e.g., a maytansine or an auristatin active agent moiety) stably associated with another moiety (e.g., the antibody). By "stably associated" is meant that a moiety is bound to another moiety or structure under standard conditions. In certain embodiments, the first and second moieties are bound to each other through one or more covalent bonds.

In certain embodiments, the conjugate is a polypeptide conjugate, which includes a polypeptide (e.g., an antibody) conjugated to a second moiety. In certain embodiments, the moiety conjugated to the polypeptide can be any of a variety of moieties of interest such as, but not limited to, a detectable label, a drug, a water-soluble polymer, or a moiety for immobilization of the polypeptide to a membrane or a surface. In certain embodiments, the conjugate is a drug conjugate, where a polypeptide is an antibody, thus providing an antibody-drug conjugate. For instance, the conjugate can be a drug conjugate, where a polypeptide is conjugated to a drug or an active agent moiety. For example, the drug or active agent can be a maytansine. "Maytansine", "maytansine moiety", "maytansine active agent moiety" and "maytansinoid" refer to a maytansine and analogs and derivatives thereof, and pharmaceutically active maytansine moieties and/or portions thereof. A maytansine conjugated to the polypeptide can be any of a variety of maytansinoid moieties such as, but not limited to, maytansine and analogs and derivatives thereof as described herein. In other instances, the drug or active agent can be an auristatin, or an analog or derivative thereof, or a pharmaceutically active auristatin moiety and/or a portion thereof. An auristatin conjugated to the polypeptide can be any of a variety of auristatin moieties such as, but not limited to, an auristatin and analogs and derivatives thereof as described herein.

In certain embodiments, the conjugate is an antibody-drug conjugate where the antibody and the drug are linked together by a linker. In some instances, the linker is a cleavable linker. A cleavable linker is a linker that includes one or more cleavable moieties, where the cleavable moiety includes one or more bonds that can dissociate under certain conditions, thus separating the cleavable linker into two or more separatable portions. For example, the cleavable moiety may include one or more covalent bonds, which under certain conditions, can dissociate or break apart to separate the cleavable linker into two or more portions. As such a cleavable linker can be included in an antibody-drug conjugate, such that under appropriate conditions, the cleavable linker is cleaved to separate or release the drug from the antibody at a desired target site of action for the drug.

A cleavable moiety may be a chemically cleavable moiety or an enzymatically cleavable moiety. For example, the cleavable moiety may be an enzymatically cleavable moiety. An enzymatically cleavable moiety is a cleavable moiety that can be separated into two or more portions as described above through the enzymatic action of an enzyme. In some embodiments, the cleavable moiety is a sulfatase-cleavable moiety. By "sulfatase-cleavable moiety" is meant that the cleavable moiety can be separated or cleaved through the enzymatic action of a sulfatase enzyme. As such, in certain embodiments, a cleavable linker of the present disclosure includes a sulfatase-cleavable moiety, which can be cleaved under appropriate conditions to separate or release the drug from the antibody at a desired target site of action for the drug. For example, the sulfatase enzyme may facilitate the hydrolysis of the sulfatase-cleavable moiety to cleave or separate the cleavable linker into two or more portions as described above.

A sulfatase enzyme may recognize a specific moiety or portion of the cleavable linker, such as a cleavable moiety (e.g., sulfatase-cleavable moiety) as described herein. The sulfatase enzyme may recognize and perform its enzymatic activity on the cleavable moiety. In certain embodiments, the sulfatase-cleavable moiety that is recognized and cleaved by the sulfatase enzyme includes a sulfate-containing group. For example, the sulfate-containing group can include an aryl sulfonic acid or an aryl sulfate ester. In some cases, the sulfate-containing group includes an aryl sulfonic acid (e.g., phenyl sulfonic acid). In some cases, the sulfate-containing group includes an aryl sulfate ester (e.g., phenyl sulfate ester). For instance, the sulfate-containing group can include an amino-benzyloxycarbonyl group substituted with the aryl sulfonic acid or the aryl sulfate ester. In some instances, the sulfate-containing group includes a meta-amino-benzyloxycarbonyl group substituted with the aryl sulfonic acid or the aryl sulfate ester. In some instances, the sulfate-containing group includes an ortho-amino-benzyloxycarbonyl group substituted with the aryl sulfonic acid or the aryl sulfate ester. In some instances, the sulfate-containing group includes a para-amino-benzyloxycarbonyl group substituted with the aryl sulfonic acid or the aryl sulfate ester. The sulfatase enzyme may facilitate the hydrolysis of the sulfate-containing group to cleave or separate the cleavable linker into two or more portions as described above.

The moiety of interest (e.g., drug or active agent) can be conjugated to the polypeptide (e.g., antibody) at any desired site of the polypeptide. Thus, the present disclosure provides, for example, a modified polypeptide having a moiety conjugated at a site at or near the C-terminus of the polypeptide. Other examples include a modified polypeptide having a moiety conjugated at a position at or near the N-terminus of the polypeptide. Examples also include a modified polypeptide having a moiety conjugated at a position between the C-terminus and the N-terminus of the polypeptide (e.g., at an internal site of the polypeptide). Combinations of the above are also possible where the modified polypeptide is conjugated to two or more moieties.

In certain embodiments, a conjugate of the present disclosure includes a drug or active agent conjugated to an amino acid reside of a polypeptide at the α-carbon of an amino acid residue. Stated another way, a conjugate includes a polypeptide where the side chain of one or more amino acid residues in the polypeptide have been modified to be attached to a drug or active agent (e.g., attached to a drug or active agent through a linker as described herein). For example, a conjugate includes a polypeptide where the α-carbon of one or more amino acid residues in the polypeptide has been modified to be attached to a maytansine (e.g., attached to a maytansine through a linker as described herein). In other instances, the conjugate includes a polypeptide where the α-carbon of one or more amino acid residues in the polypeptide has been modified to be attached to an auristatin (e.g., attached to an auristatin through a linker as described herein).

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, one or more moieties may be conjugated to a single amino acid residue of the polypeptide. In some cases, one moiety is conjugated to an amino acid residue of the polypeptide. In other embodiments, two moieties may be conjugated to the same amino acid residue of the polypeptide. In other embodiments, a first moiety is conjugated to a first amino acid residue of the polypeptide and a second moiety is conjugated to a second amino acid residue of the polypeptide. Combinations of the above are also possible, for example where a polypeptide is conjugated to a first moiety at a first amino acid residue and conjugated to two other moieties at a second amino acid residue. Other combinations are also possible, such as, but not limited to, a polypeptide conjugated to first and second moieties at a first amino acid residue and conjugated to third and fourth moieties at a second amino acid residue, etc.

The one or more amino acid residues of the polypeptide that are conjugated to the one or more moieties may be naturally occurring amino acids, unnatural amino acids, or combinations thereof. For instance, the conjugate may include a moiety conjugated to a naturally occurring amino acid residue of the polypeptide. In other instances, the conjugate may include a moiety conjugated to an unnatural amino acid residue of the polypeptide. One or more moieties may be conjugated to the polypeptide at a single natural or unnatural amino acid residue as described above. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to one or two moieties, such that multiple sites in the polypeptide are modified.

As described herein, a polypeptide may be conjugated to one or more moieties. In certain embodiments, the moiety of interest is a chemical entity, such as a drug or a detectable label. For example, a drug (e.g., maytansine or auristatin) may be conjugated to the polypeptide, or in other embodiments, a detectable label may be conjugated to the polypeptide. Thus, for instance, embodiments of the present disclosure include, but are not limited to, the following: a conjugate of a polypeptide and a drug; a conjugate of a polypeptide and a detectable label; a conjugate of two or more drugs and a polypeptide; a conjugate of two or more detectable labels and a polypeptide; and the like.

In certain embodiments, the polypeptide and the moiety of interest are conjugated through a coupling moiety. For example, the polypeptide and the moiety of interest may each be bound (e.g., covalently bonded) to the coupling moiety, thus indirectly binding the polypeptide and the moiety of interest (e.g., a drug, such as maytansine) together through the coupling moiety. In some cases, the coupling moiety includes a hydrazinyl-indolyl or a hydrazinyl-pyrrolo-pyridinyl compound, or a derivative of a hydrazinyl-indolyl or a hydrazinyl-pyrrolo-pyridinyl compound. For instance, a general scheme for coupling a moiety of interest (e.g., a maytansine) to a polypeptide through a hydrazinyl-indolyl or a hydrazinyl-pyrrolo-pyridinyl coupling moiety is shown in the general reaction scheme below. Hydrazinyl-indolyl and hydrazinyl-pyrrolo-pyridinyl coupling moiety are also referred to herein as a hydrazino-iso-Pictet-Spengler (HIPS) coupling moiety and an aza-hydrazino-iso-Pictet-Spengler (azaHIPS) coupling moiety, respectively.

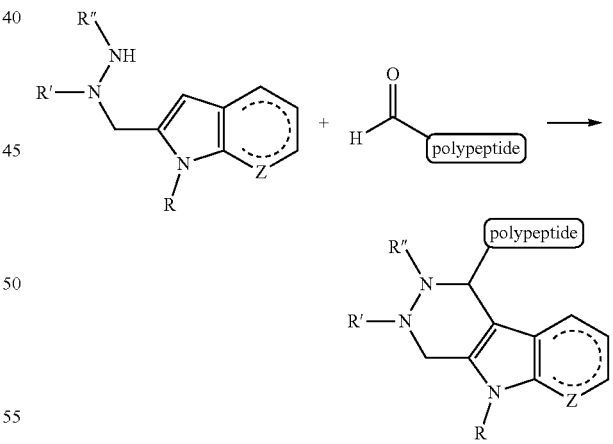

In the reaction scheme above, R is the moiety of interest (e.g., a drug or active agent) that is conjugated to the polypeptide. As shown in the reaction scheme above, a polypeptide that includes a 2-formylglycine residue (fGly) is reacted with a drug or active agent that has been modified to include a coupling moiety (e.g., a hydrazinyl-indolyl or a hydrazinyl-pyrrolo-pyridinyl coupling moiety) to produce a polypeptide conjugate attached to the coupling moiety, thus attaching the drug or active agent to the polypeptide through the coupling moiety.

As described herein, the moiety can be any of a variety of moieties such as, but not limited to, chemical entity, such as a detectable label, or a drug. R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. Z may be $CR^{21}$, $NR^{22}$, N, O or S, where $R^{21}$ and $R^{22}$ are each independently selected from any of the substituents described for R' and R" above.

Other hydrazinyl-indolyl or hydrazinyl-pyrrolo-pyridinyl coupling moieties are also possible, as shown in the conjugates and compounds described herein. For example, the hydrazinyl-indolyl or hydrazinyl-pyrrolo-pyridinyl coupling moieties may be modified to be attached (e.g., covalently attached) to a linker. As such, embodiments of the present disclosure include a hydrazinyl-indolyl or hydrazinyl-pyrrolo-pyridinyl coupling moiety attached to a drug or active agent through a linker. Various embodiments of the linker that may couple the hydrazinyl-indolyl or hydrazinyl-pyrrolo-pyridinyl coupling moiety to the drug or active agent are described in detail herein. For example, in some instances, the linker is a cleavable linker, such as a cleavable linker having a sulfatase-cleavable moiety, as described herein.

In certain embodiments, the polypeptide may be conjugated to a moiety of interest, where the polypeptide is modified before conjugation to the moiety of interest. Modification of the polypeptide may produce a modified polypeptide that contains one or more reactive groups suitable for conjugation to the moiety of interest. In some cases, the polypeptide may be modified at one or more amino acid residues to provide one or more reactive groups suitable for conjugation to the moiety of interest (e.g., a moiety that includes a coupling moiety, such as a hydrazinyl-indolyl or a hydrazinyl-pyrrolo-pyridinyl coupling moiety as described above). For example, the polypeptide may be modified to include a reactive aldehyde group (e.g., a reactive aldehyde). A reactive aldehyde may be included in an "aldehyde tag" or "ald-tag", which as used herein refers to an amino acid sequence derived from a sulfatase motif (e.g., L(C/S)TPSR) that has been converted by action of a formylglycine generating enzyme (FGE) to contain a 2-formylglycine residue (referred to herein as "FGly"). The FGly residue generated by an FGE may also be referred to as a "formylglycine". Stated differently, the term "aldehyde tag" is used herein to refer to an amino acid sequence that includes a "converted" sulfatase motif (i.e., a sulfatase motif in which a cysteine or serine residue has been converted to FGly by action of an FGE, e.g., L(FGly)TPSR). A converted sulfatase motif may be derived from an amino acid sequence that includes an "unconverted" sulfatase motif (i.e., a sulfatase motif in which the cysteine or serine residue has not been converted to FGly by an FGE, but is capable of being converted, e.g., an unconverted sulfatase motif with the sequence: L(C/S) TPSR). By "conversion" as used in the context of action of a formylglycine generating enzyme (FGE) on a sulfatase motif refers to biochemical modification of a cysteine or serine residue in a sulfatase motif to a formylglycine (FGly) residue (e.g., Cys to FGly, or Ser to FGly). Additional aspects of aldehyde tags and uses thereof in site-specific protein modification are described in U.S. Pat. Nos. 7,985, 783 and 8,729,232, the disclosures of each of which are incorporated herein by reference.

In some cases, the modified polypeptide containing the FGly residue may be conjugated to the moiety of interest by reaction of the FGly with a compound (e.g., a compound containing a hydrazinyl-indolyl or a hydrazinyl-pyrrolo-pyridinyl coupling moiety, as described above). For example, an FGly-containing polypeptide may be contacted with a reactive partner-containing drug under conditions suitable to provide for conjugation of the drug to the polypeptide. In some instances, the reactive partner-containing drug may include a hydrazinyl-indolyl or a hydrazinyl-pyrrolo-pyridinyl coupling moiety as described above. For example, a drug or active agent may be modified to include a hydrazinyl-indolyl or a hydrazinyl-pyrrolo-pyridinyl coupling moiety. In some cases, the drug or active agent is attached to a hydrazinyl-indolyl or a hydrazinyl-pyrrolo-pyridinyl, such as covalently attached to a hydrazinyl-indolyl or a hydrazinyl-pyrrolo-pyridinyl through a linker, such as a cleavable linker as described in detail herein.

In certain embodiments, a conjugate of the present disclosure includes a polypeptide (e.g., an antibody) having at least one modified amino acid residue. The modified amino acid residue of the polypeptide may be coupled to a drug or active agent containing a hydrazinyl-indolyl or a hydrazinyl-pyrrolo-pyridinyl coupling moiety as described above. In certain embodiments, the modified amino acid residue of the polypeptide (e.g., antibody) may be derived from a cysteine or serine residue that has been converted to an FGly residue as described above. In certain embodiments, the FGly residue is conjugated to a drug or active agent containing a hydrazinyl-indolyl or a hydrazinyl-pyrrolo-pyridinyl coupling moiety as described above to provide a conjugate of the present disclosure where the drug or active agent is conjugated to the polypeptide through the hydrazinyl-indolyl or hydrazinyl-pyrrolo-pyridinyl coupling moiety. As used herein, the term FGly' refers to the modified amino acid residue of the polypeptide (e.g., antibody) that is coupled to the moiety of interest (e.g., a drug or active agent).

In certain embodiments, the conjugate includes at least one modified amino acid residue of the formula (I) described herein. For instance, the conjugate may include at least one modified amino acid residue (FGly') as described above. In some embodiments, the conjugate is of formula (I):

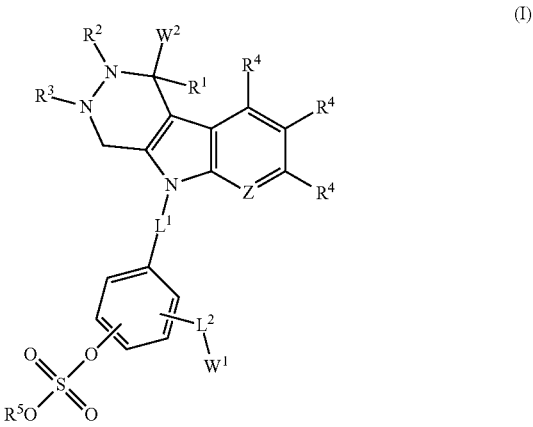

(I)

wherein is $CR^4$ or N;

$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$R^5$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$L^1$ is a first linker;

$L^2$ is a second linker;

$W^1$ is the drug; and $W^2$ is the antibody.

In certain embodiments, the conjugate is of formula (Ia):

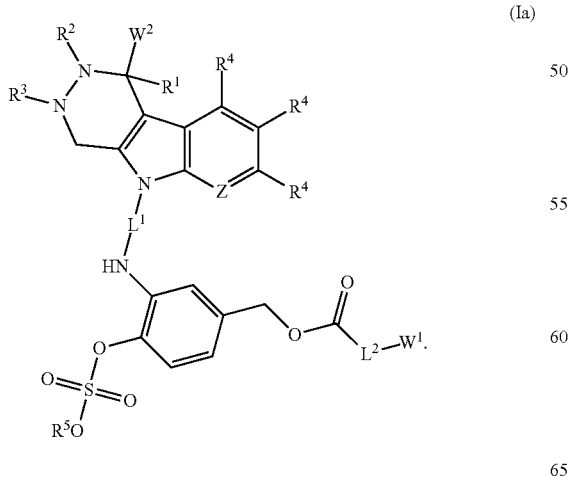

(Ia)

In certain embodiments, the conjugate is of formula (Ib):

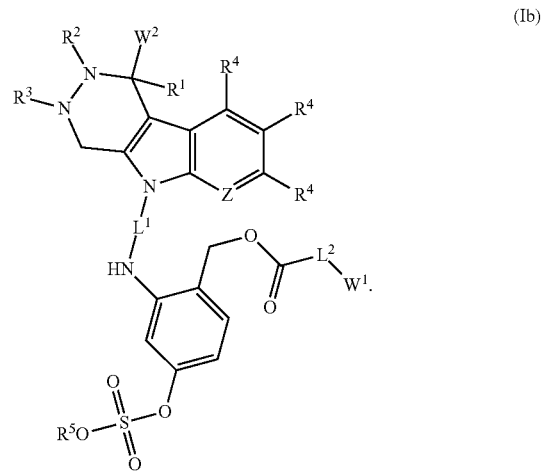

(Ib)

In certain embodiments, the conjugate is of formula (Ic):

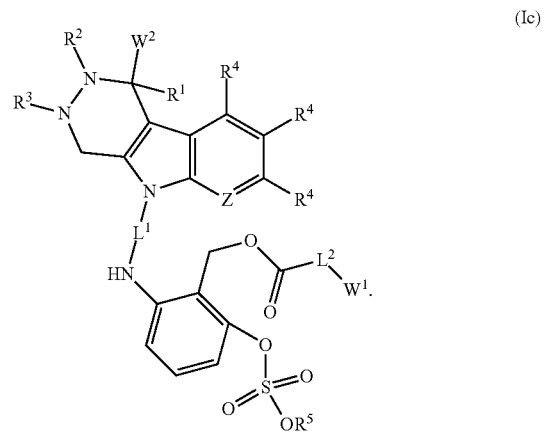

(Ic)

In certain embodiments, the conjugate is of formula (Id):

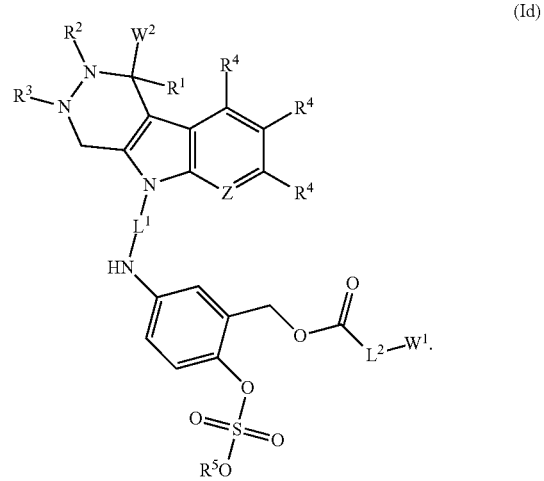

(Id)

In certain embodiments, the conjugate is of formula (Ie):

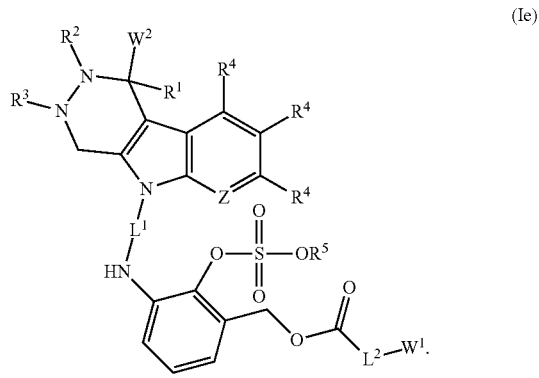

(Ie)

The substituents related to conjugates of formula (I) are described in more detail below. References to formula (I) are intended to also encompass formulae (Ia), (Ib), (Ic), (Id), and (Ie).

In certain embodiments, Z is $CR^4$ or N. In certain embodiments, Z is $CR^4$. In certain embodiments, Z is N.

In certain embodiments, $R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^1$ is hydrogen. In certain embodiments, $R^1$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^1$ is methyl. In certain embodiments, $R^1$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^1$ is alkynyl or substituted alkynyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^1$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^1$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^1$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^1$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl.

In certain embodiments, $R^2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^2$ is hydrogen. In certain embodiments, $R^2$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^2$ is methyl. In certain embodiments, $R^2$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^2$ is alkynyl or substituted alkynyl. In certain embodiments, $R^2$ is alkoxy or substituted alkoxy. In certain embodiments, $R^2$ is amino or substituted amino. In certain embodiments, $R^2$ is carboxyl or carboxyl ester. In certain embodiments, $R^2$ is acyl or acyloxy. In certain embodiments, $R^2$ is acyl amino or amino acyl. In certain embodiments, $R^2$ is alkylamide or substituted alkylamide. In certain embodiments, $R^2$ is sulfonyl. In certain embodiments, $R^2$ is thioalkoxy or substituted thioalkoxy. In certain embodiments, $R^2$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^2$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^2$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^2$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^3$ is hydrogen. In certain embodiments, $R^3$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^3$ is methyl. In certain embodiments, $R^3$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl or acyloxy. In certain embodiments, $R^3$ is acyl amino or amino acyl. In certain embodiments, $R^3$ is alkylamide or substituted alkylamide. In certain embodiments, $R^3$ is sulfonyl. In certain embodiments, $R^3$ is thioalkoxy or substituted thioalkoxy. In certain embodiments, $R^3$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^3$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^3$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^3$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ and $R^3$ are optionally cyclically linked to form a 5 or 6-membered heterocyclyl. In certain embodiments, $R^2$ and $R^3$ are cyclically linked to form a 5 or 6-membered heterocyclyl. In certain embodiments, $R^2$ and $R^3$ are cyclically linked to form a 5-membered heterocyclyl. In certain embodiments, $R^2$ and $R^3$ are cyclically linked to form a 6-membered heterocyclyl.

In certain embodiments, each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^4$ are described in more detail as follows. In certain embodiments, $R^4$ is hydrogen. In certain embodiments, each $R^4$ is hydrogen. In certain embodiments, $R^4$ is halogen, such as F, Cl, Br or I. In certain embodiments, $R^4$ is F. In certain embodiments, $R^4$ is Cl. In certain embodiments, $R^4$ is Br. In certain embodiments, $R^4$ is I. In certain embodiments, $R^4$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^4$ is methyl. In certain embodiments, $R^4$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^4$ is alkynyl or substituted alkynyl. In certain embodiments, $R^4$ is alkoxy or substituted alkoxy. In certain embodiments, $R^4$ is amino or substituted amino. In certain embodiments, $R^4$ is carboxyl or carboxyl ester. In certain embodiments, $R^4$ is acyl or acyloxy. In certain embodiments, $R^4$ is acyl amino or amino acyl. In certain embodiments, $R^4$ is alkylamide or substituted alkylamide. In certain embodiments, $R^4$ is sulfonyl. In certain embodiments, $R^4$ is thioalkoxy or substituted thioalkoxy. In certain embodiments, $R^4$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl (e.g., phenyl or substituted phenyl). In certain embodiments, $R^4$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^4$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^4$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^5$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^5$ is hydrogen. In certain embodiments, $R^5$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^5$ is methyl. In certain embodiments, $R^5$ is ethyl. In certain embodiments, $R^5$ is propyl (e.g., n-propyl or isopropyl). In certain embodiments, $R^5$ is butyl (e.g., n-butyl, isobutyl, sec-butyl, or t-butyl). In certain embodiments, $R^5$ is pentyl (e.g., n-pentyl or neopentyl, etc.). In certain embodiments, $R^5$ is neopentyl.

In certain embodiments, $R^5$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^5$ is alkynyl or substituted alkynyl. In certain embodiments, $R^5$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl (e.g., phenyl or substituted phenyl). In certain embodiments, $R^5$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^5$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^5$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $W^1$ is a drug. For example, $W^1$ can be a maytansinoid. Further description of the maytansinoid is found in the disclosure herein. In some instances, $W^1$ is an auristatin. Further description of the auristatin is found in the disclosure herein.

In certain embodiments, $W^2$ is an antibody. Further description of antibodies that find use in the subject conjugates is found in the disclosure herein.

In certain embodiments, the compounds of formula (I) include one or more linkers. The linker may be utilized to bind a coupling moiety to one or more moieties of interest and/or one or more polypeptides. In some embodiments, the linker binds a coupling moiety to either a polypeptide or a chemical entity such as a drug. The linker may be bound (e.g., covalently bonded) to the coupling moiety (e.g., as described herein) at any convenient position. For example, the linker may attach a hydrazinyl-indolyl or a hydrazinyl-pyrrolo-pyridinyl coupling moiety to a drug (e.g., a maytansine or an auristatin). The hydrazinyl-indolyl or hydrazinyl-pyrrolo-pyridinyl coupling moiety may be used to conjugate the linker (and thus the drug) to a polypeptide, such as an antibody. For example, the coupling moiety may be used to conjugate the linker (and thus the drug) to a modified amino acid residue of the polypeptide, such as an FGly reside of an antibody.

In certain embodiments, the linker includes one or more linkers, such as a first linker, $L^1$, and a second linker $L^2$. In addition, the linker may include a cleavable moiety, such as a sulfatase-cleavable moiety as described herein. In some instances, the sulfatase-cleavable moiety includes a sulfate-containing group. In some cases, the linker includes one or more linkers, such as a first linker, $L^1$, and a second linker $L^2$, and a sulfatase-cleavable moiety (e.g., sulfate-containing group). As such, the linker may be composed of a first linker ($L^1$), a second linker ($L^2$), and a sulfate-containing group. For example, the linker may include a first linker ($L^1$) that links the sulfatase-cleavable moiety (e.g., sulfate-containing group) to a coupling moiety (e.g., a hydrazinyl-indolyl or hydrazinyl-pyrrolo-pyridinyl coupling moiety as described herein), and a second linker ($L^2$) that links the sulfatase-cleavable moiety (e.g., sulfate-containing group) to a chemical entity, such as a drug as described herein. As such, the linker may include a first linker ($L^1$) that links the sulfatase-cleavable moiety (e.g., sulfate-containing group) to an antibody (e.g., through a hydrazinyl-indolyl or hydrazinyl-pyrrolo-pyridinyl coupling moiety as described herein), and a second linker ($L^2$) that links the sulfatase-cleavable moiety (e.g., sulfate-containing group) to a chemical entity, such as a drug as described herein.

For example, as shown in formula (I) above, $L^1$ is attached to $W^2$ through the coupling moiety, and thus $W^2$ is indirectly bonded to the first linker $L^1$ through the coupling moiety. As described above, $W^2$ is an antibody, and thus $L^1$ is attached through the coupling moiety to an antibody, e.g., the first linker $L^1$ is indirectly bonded to the antibody through the coupling moiety (e.g., through a hydrazinyl-indolyl or hydrazinyl-pyrrolo-pyridinyl coupling moiety as described herein). In addition, as shown in formula (I) above, $L^1$ is attached to the sulfatase-cleavable moiety (e.g., a sulfate-containing group). As such, $W^2$ (e.g., the antibody) is indirectly bonded to the sulfatase-cleavable moiety (e.g., sulfate-containing group) through the first linker $L^1$.

In addition, as shown in formula (I) above, $L^2$ is attached to $W^1$, and thus the sulfatase-cleavable moiety (e.g., sulfate-containing group) is indirectly bonded to $W^1$ through the second linker $L^2$. As described above, $W^1$ is a drug, and thus the second linker $L^2$ attaches the sulfatase-cleavable moiety (e.g., sulfate-containing group) to the drug, e.g., the sulfatase-cleavable moiety is indirectly bonded to the drug through the second linker, $L^2$.

Any convenient linkers may be utilized for the first linker ($L^1$) and the second linker ($L^2$) in the subject conjugates and compounds. In certain embodiments, the first linker ($L^1$) and the second linker ($L^2$) each independently may include a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, the first linker ($L^1$) and the second linker ($L^2$) each independently may include an alkyl or substituted alkyl group. In certain embodiments, the first linker ($L^1$) and the second linker ($L^2$) each independently may include an alkenyl or substituted alkenyl group. In certain embodiments, the first linker ($L^1$) and the second linker ($L^2$) each independently may include an alkynyl or substituted alkynyl group. In certain embodiments, the first linker ($L^1$) and the second linker ($L^2$) each independently may include an alkoxy or substituted alkoxy group. In certain embodiments, the first linker ($L^1$) and the second linker ($L^2$) each independently may include an amino or substituted amino group. In certain embodiments, the first linker ($L^1$) and the second linker ($L^2$) each independently may include a carboxyl or carboxyl ester group. In certain embodiments, the first linker ($L^1$) and the second linker ($L^2$) each independently may include an acyl amino group. In certain embodiments, the first linker ($L^1$) and the second linker ($L^2$) each independently may include an alkylamide or substituted alkylamide group. In certain embodiments, the first linker ($L^1$) and the second linker ($L^2$) each independently may include an aryl or substituted aryl group. In certain embodiments, the first linker ($L^1$) and the second linker ($L^2$) each independently may include a heteroaryl or substituted heteroaryl group. In certain embodiments, the first linker ($L^1$) and the second linker ($L^2$) each independently may include a cycloalkyl or substituted cycloalkyl group. In certain embodiments, the first linker ($L^1$) and the second linker ($L^2$) each independently may include a heterocyclyl or substituted heterocyclyl group.

In certain embodiments, the first linker ($L^1$) and the second linker ($L^2$) each independently may include a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Other linkers are also possible, as shown in the conjugates and compounds described in more detail below.

In some embodiments, $L^1$ is a first linker described by the formula -$(L^{11})_a$-$(L^{12})_b$-$(L^{13})_c$-$(L^{14})_d$-, wherein $L^{11}$, $L^{12}$, $L^{13}$ and $L^{14}$ are each independently a first linker subunit, and a, b, c and d are each independently 0 or 1, wherein the sum of a, b, c and d is 1 to 4.

In certain embodiments, the sum of a, b, c and d is 1. In certain embodiments, the sum of a, b, c and d is 2. In certain embodiments, the sum of a, b, c and d is 3. In certain embodiments, the sum of a, b, c and d is 4. In certain embodiments, a, b, c and d are each 1. In certain embodiments, a, b and c are each 1 and d is 0. In certain embodiments, a and b are each 1 and c and d are each 0. In certain embodiments, a is 1 and b, c and d are each 0.

In certain embodiments, $L^{11}$ is attached to the hydrazinyl-indolyl or the hydrazinyl-pyrrolo-pyridinyl coupling moiety (e.g., as shown in formula (I) above). In certain embodiments, $L^{12}$, if present, is attached to the cleavable moiety (e.g., sulfatase-cleavable moiety, such as a sulfate-containing group). In certain embodiments, $L^{13}$, if present, is attached to the cleavable moiety (e.g., sulfatase-cleavable moiety, such as a sulfate-containing group). In certain embodiments, $L^{14}$, if present, is attached to the cleavable moiety (e.g., sulfatase-cleavable moiety, such as a sulfate-containing group).

Any convenient linker subunits may be utilized in the first linker $L^1$. Linker subunits of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocyclic groups, combinations thereof, and substituted versions thereof. In some embodiments, each of $L^{11}$, $L^{12}$, $L^{13}$ and $L^{14}$ (if present) comprise one or more groups independently selected from a polyethylene glycol, a modified polyethylene glycol, an amino acid residue, an alkyl group, a substituted alkyl, an aryl group, a substituted aryl group, and a diamine (e.g., a linking group that includes an alkylene diamine).

In some embodiments, $L^{11}$ (if present) comprises a polyethylene glycol, a modified polyethylene glycol, an amino acid residue, an alkyl group, a substituted alkyl, an aryl group, a substituted aryl group, or a diamine. In some embodiments, $L^{11}$ comprises a polyethylene glycol. In some embodiments, $L^{11}$ comprises a modified polyethylene glycol. In some embodiments, $L^{11}$ comprises an amino acid residue. In some embodiments, $L^{11}$ comprises an alkyl group or a substituted alkyl. In some embodiments, $L^{11}$ comprises an aryl group or a substituted aryl group. In some embodiments, $L^{11}$ comprises a diamine (e.g., a linking group comprising an alkylene diamine).

In some embodiments, $L^{12}$ (if present) comprises a polyethylene glycol, a modified polyethylene glycol, an amino acid residue, an alkyl group, a substituted alkyl, an aryl group, a substituted aryl group, or a diamine. In some embodiments, $L^{12}$ comprises a polyethylene glycol. In some embodiments, $L^{12}$ comprises a modified polyethylene glycol. In some embodiments, $L^{12}$ comprises an amino acid residue. In some embodiments, $L^{12}$ comprises an alkyl group or a substituted alkyl. In some embodiments, $L^{12}$ comprises an aryl group or a substituted aryl group. In some embodiments, $L^{12}$ comprises a diamine (e.g., a linking group comprising an alkylene diamine).

In some embodiments, $L^{13}$ (if present) comprises a polyethylene glycol, a modified polyethylene glycol, an amino acid residue, an alkyl group, a substituted alkyl, an aryl group, a substituted aryl group, or a diamine. In some embodiments, $L^{13}$ comprises a polyethylene glycol. In some embodiments, $L^{13}$ comprises a modified polyethylene glycol. In some embodiments, $L^{13}$ comprises an amino acid residue. In some embodiments, $L^{13}$ comprises an alkyl group or a substituted alkyl. In some embodiments, $L^{13}$ comprises an aryl group or a substituted aryl group. In some embodiments, $L^{13}$ comprises a diamine (e.g., a linking group comprising an alkylene diamine).

In some embodiments, $L^{14}$ (if present) comprises a polyethylene glycol, a modified polyethylene glycol, an amino acid residue, an alkyl group, a substituted alkyl, an aryl group, a substituted aryl group, or a diamine. In some embodiments, $L^{14}$ comprises a polyethylene glycol. In some embodiments, $L^{14}$ comprises a modified polyethylene glycol. In some embodiments, $L^{14}$ comprises an amino acid residue. In some embodiments, $L^{14}$ comprises an alkyl group or a substituted alkyl. In some embodiments, $L^{14}$ comprises an aryl group or a substituted aryl group. In some embodiments, $L^{14}$ comprises a diamine (e.g., a linking group comprising an alkylene diamine).

In some embodiments, $L^1$ is a first linker comprising $-(L^{11})_a-(L^{12})_b-(L^{13})_c-(L^{14})_d-$, where:

$-(L^{11})_a-$ is $-(T^1-V^1)_a-$;

$-(L^{12})_b-$ is $-(T^2-V^2)_b-$;

$-(L^{13})_c-$ is $-(T^3-V^3)_c-$; and $-(L^{14})_d-$ is $-(T^4-V^4)_d-$, wherein $T^1$, $T^2$, $T^3$ and $T^4$, if present, are tether groups; $V^1$, $V^2$, $V^3$ and $V^4$, if present, are covalent bonds or linking functional groups; and a, b, c and d are each independently 0 or 1, wherein the sum of a, b, c and d is 1 to 4.

As described above, in certain embodiments, $L^{11}$ is attached to the hydrazinyl-indolyl or the hydrazinyl-pyrrolo-pyridinyl coupling moiety (e.g., as shown in formula (I) above). As such, in certain embodiments, $T^1$ is attached to the hydrazinyl-indolyl or the hydrazinyl-pyrrolo-pyridinyl coupling moiety (e.g., as shown in formula (I) above). In certain embodiments, $V^1$ is attached to the cleavable moiety (e.g., sulfatase-cleavable moiety, such as a sulfate-containing group). In certain embodiments, $L^{12}$, if present, is attached to the cleavable moiety (e.g., sulfatase-cleavable moiety, such as a sulfate-containing group). As such, in certain embodiments, $T^2$, if present, is attached to the cleavable moiety (e.g., sulfatase-cleavable moiety, such as a sulfate-containing group), or $V^2$, if present, is attached to the cleavable moiety (e.g., sulfatase-cleavable moiety, such as a sulfate-containing group). In certain embodiments, $L^{13}$, if present, is attached to the cleavable moiety (e.g., sulfatase-cleavable moiety, such as a sulfate-containing group). As such, in certain embodiments, $T^3$, if present, is attached to the cleavable moiety (e.g., sulfatase-cleavable moiety, such as a sulfate-containing group), or $V^3$, if present, is attached to the cleavable moiety (e.g., sulfatase-cleavable moiety, such as a sulfate-containing group). In certain embodiments, $L^{14}$, if present, is attached to the cleavable moiety (e.g., sulfatase-cleavable moiety, such as a sulfate-containing group). As such, in certain embodiments, $T^4$, if present, is attached to the cleavable moiety (e.g., sulfatase-cleavable moiety, such as a sulfate-containing group), or $V^4$, if present, is attached to the cleavable moiety (e.g., sulfatase-cleavable moiety, such as a sulfate-containing group).

Regarding the tether groups, $T^1$, $T^2$, $T^3$ and $T^4$, any convenient tether groups may be utilized in the subject linkers. In some embodiments, $T^1$, $T^2$, $T^3$ and $T^4$ each comprise one or more groups independently selected from a $(C_1-C_{12})$alkyl, a substituted $(C_1-C_{12})$alkyl, an $(EDA)_w$, $(PEG)_n$, $(AA)_p$, $-(CR^{13}OH)_h-$, piperidin-4-amino (4AP), an acetal group, a disulfide, a hydrazine, and an ester, where w is an integer from 1 to 20, n is an integer from 1 to 30, p is an integer from 1 to 20, and h is an integer from 1 to 12.

In certain embodiments, the tether group (e.g., $T^1$, $T^2$, $T^3$ and/or $T^4$) includes a $(C_1-C_{12})$alkyl or a substituted $(C_1-C_{12})$alkyl. In certain embodiments, $(C_1-C_{12})$alkyl is a straight chain or branched alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, $(C_1-C_{12})$alkyl may be an alkyl or substituted alkyl, such as $C_1-C_{12}$ alkyl, or $C_1-C_{10}$ alkyl, or $C_1-C_6$ alkyl, or $C_1-C_3$ alkyl. In some instances, $(C_1-C_{12})$alkyl is a $C_2$-alkyl. For example, $(C_1-C_{12})$alkyl may be an alkylene or substituted alkylene, such as $C_1-C_{12}$ alkylene, or $C_1-C_{10}$ alkylene, or $C_1-C_6$ alkylene, or $C_1-C_3$ alkylene. In some instances, $(C_1-C_{12})$alkyl is a $C_2$-alkylene (e.g., $CH_2CH_2$).

In certain embodiments, substituted $(C_1-C_{12})$alkyl is a straight chain or branched substituted alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, substituted $(C_1-C_{12})$alkyl may be a substituted alkyl, such as substituted $C_1-C_{12}$ alkyl, or substituted $C_1-C_{10}$ alkyl, or substituted $C_1-C_6$ alkyl, or substituted $C_1-C_3$ alkyl. In some instances, substituted $(C_1-C_{12})$alkyl is a substituted $C_2$-alkyl. For example, substituted $(C_1-C_{12})$alkyl may be a substituted alkylene, such as substituted $C_1-C_{12}$ alkylene, or substituted $C_1-C_{10}$ alkylene, or substituted $C_1-C_6$ alkylene, or substituted $C_1-C_3$ alkylene. In some instances, substituted $(C_1-C_{12})$alkyl is a substituted $C_2$-alkylene.

In certain embodiments, the tether group (e.g., $T^1$, $T^2$, $T^3$ and/or $T^4$) includes an ethylene diamine (EDA) moiety, e.g., an EDA containing tether. In certain embodiments, $(EDA)_w$ includes one or more EDA moieties, such as where w is an integer from 1 to 50, such as from 1 to 40, from 1 to 30, from 1 to 20, from 1 to 12 or from 1 to 6, such as 1, 2, 3, 4, 5 or 6). The linked ethylene diamine (EDA) moieties may optionally be substituted at one or more convenient positions with any convenient substituents, e.g., with an alkyl, a substituted alkyl, an acyl, a substituted acyl, an aryl or a substituted aryl. In certain embodiments, the EDA moiety is described by the structure:

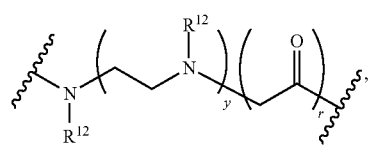

where y is an integer from 1 to 6, or is 0 or 1, and each $R^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, y is 1, 2, 3, 4, 5 or 6. In certain embodiments, y is 1 and r is 0. In certain embodiments, y is 1 and r is 1. In certain embodiments, y is 2 and r is 0. In certain embodiments, y is 2 and r is 1. In certain embodiments, each $R^{12}$ is independently selected from hydrogen, an alkyl, a substituted alkyl, an aryl and a substituted aryl. In certain embodiments, any two adjacent $R^{12}$ groups of the EDA may be cyclically linked, e.g., to form a piperazinyl ring. In certain embodiments, y is 1 and the two adjacent $R^{12}$ groups are an alkyl group, cyclically linked to form a piperazinyl ring. In certain embodiments, y is 1 and the adjacent $R^{12}$ groups are selected from hydrogen, an alkyl (e.g., methyl) and a substituted alkyl (e.g., lower alkyl-OH, such as ethyl-OH or propyl-OH).

In certain embodiments, the tether group (e.g., $T^1$, $T^2$, $T^3$ and/or $T^4$) includes a 4-amino-piperidine (4AP) moiety (also referred to herein as piperidin-4-amino, P4A). The 4AP moiety may optionally be substituted at one or more convenient positions with any convenient substituents, e.g., with an alkyl, a substituted alkyl, a polyethylene glycol moiety, an acyl, a substituted acyl, an aryl or a substituted aryl. In certain embodiments, the 4AP moiety is described by the structure:

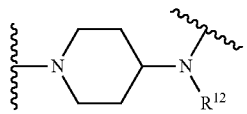

where $R^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is a polyethylene glycol moiety. In certain embodiments, $R^{12}$ is a carboxy modified polyethylene glycol.

In certain embodiments, $R^{12}$ includes a polyethylene glycol moiety described by the formula: $(PEG)_k$, which may be represented by the structure:

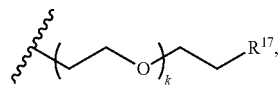

where k is an integer from 1 to 20, such as from 1 to 18, or from 1 to 16, or from 1 to 14, or from 1 to 12, or from 1 to 10, or from 1 to 8, or from 1 to 6, or from 1 to 4, or 1 or 2, such as 1, 2, 3, 4, 5, 6, 7, 8, 9, 10, 11, 12, 13, 14, 15, 16, 17, 18, 19 or 20. In some instances, k is 2. In certain embodiments, $R^{17}$ is selected from OH, COOH, or COOR, where R is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{17}$ is COOH.

In certain embodiments, a tether group (e.g., $T^1$, $T^2$, $T^3$ and/or $T^4$) includes $(PEG)_n$, where $(PEG)_n$ is a polyethylene glycol or a modified polyethylene glycol linking unit. In certain embodiments, $(PEG)_n$ is described by the structure:

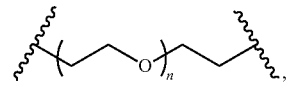

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 2. In some instances, n is 3. In some instances, n is 6. In some instances, n is 12.

In certain embodiments, a tether group (e.g., $T^1$, $T^2$, $T^3$ and/or $T^4$) includes $(AA)_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In certain embodiments, p is 1. In certain embodiments, p is 2.

In certain embodiments, a tether group (e.g., $T^1$, $T^2$, $T^3$ and/or $T^4$) includes a moiety described by the formula $—(CR^{13}OH)_h—$, where h is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, h is 1. In certain embodiments, h is 2. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{13}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{13}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{13}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{13}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^{13}$ is selected from hydrogen, an alkyl, a substituted alkyl, an aryl, and a substituted aryl. In these embodiments, alkyl, substituted alkyl, aryl, and substituted aryl are as described above for $R^{13}$.

Regarding the linking functional groups, $V^1$, $V^2$, $V^3$ and $V^4$, any convenient linking functional groups may be utilized in the first linker $L^1$. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoramidate, and the like. In some embodiments, $V^1$, $V^2$, $V^3$ and $V^4$ are each independently selected from a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, where q is an integer from 1 to 6. In certain embodiments, q is an integer from 1 to 6 (e.g., 1, 2, 3, 4, 5 or 6). In certain embodiments, q is 1. In certain embodiments, q is 2.

In some embodiments, each $R^{15}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^{15}$ are described in more detail as follows. In certain embodiments, $R^{15}$ is hydrogen. In certain embodiments, each $R^{15}$ is hydrogen. In certain embodiments, $R^{15}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{15}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{15}$ is alkynyl or substituted alkynyl. In certain embodiments, $R^{15}$ is alkoxy or substituted alkoxy. In certain embodiments, $R^{15}$ is amino or substituted amino. In certain embodiments, $R^{15}$ is carboxyl or carboxyl ester. In certain embodiments, $R^{15}$ is acyl or acyloxy. In certain embodiments, $R^{15}$ is acyl amino or amino acyl. In certain embodiments, $R^{15}$ is alkylamide or substituted alkylamide. In certain embodiments, $R^{15}$ is sulfonyl. In certain embodiments, $R^{15}$ is thioalkoxy or substituted thioalkoxy. In certain embodiments, $R^{15}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{15}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{15}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{15}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, the hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl substituents are as described above for $R^{15}$.

In certain embodiments, the tether group includes an acetal group, a disulfide, a hydrazine, or an ester. In some embodiments, the tether group includes an acetal group. In some embodiments, the tether group includes a disulfide. In some embodiments, the tether group includes a hydrazine. In some embodiments, the tether group includes an ester.

As described above, in some embodiments, $L^1$ is a first linker comprising -(T$^1$-V$^1$)$_a$-(T$^2$-V$^2$)$_b$-(T$^3$-V$^3$)$_c$-(T$^4$-V$^4$)$_d$-, where a, b, c and d are each independently 0 or 1, where the sum of a, b, c and d is 1 to 4.

In some embodiments, in the first linker $L^1$:
  $T^1$ is selected from a $(C_1-C_{12})$alkyl and a substituted $(C_1-C_{12})$alkyl;
  $T^2$, $T^3$ and $T^4$ are each independently selected from $(C_1-C_{12})$alkyl, substituted $(C_1-C_{12})$alkyl, (EDA)$_w$, (PEG)$_n$, (AA)$_p$, —(CR$^{13}$OH)$_h$—, 4-amino-piperidine (4AP), an acetal group, a disulfide, a hydrazine, and an ester; and
  $V^1$, $V^2$, $V^3$ and $V^4$ are each independently selected from a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;

wherein:
  (PEG)$_n$ is

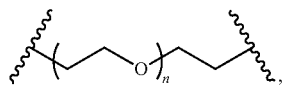

where n is an integer from 1 to 30;
  EDA is an ethylene diamine moiety having the following structure:

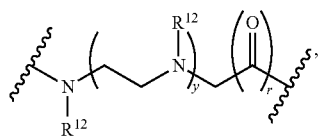

where y is an integer from 1 to 6 and r is 0 or 1;
  4-amino-piperidine (4AP) is

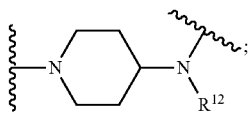

AA is an amino acid residue, where p is an integer from 1 to 20; and
  each $R^{15}$ and $R^{12}$ is independently selected from hydrogen, an alkyl, a substituted alkyl, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In certain embodiments, $T^1$, $T^2$, $T^3$ and $T^4$ and $V^1$, $V^2$, $V^3$ and $V^4$ are selected from the following:

$T^1$ is $(C_1-C_{12})$alkyl and $V^1$ is —CO—;
$T^2$ is 4AP and $V^2$ is a covalent bond;
$T^3$ is $(PEG)_n$ and $V^3$ is —CONR$^{15}$—; and
$T^4$ is $(C_1-C_{12})$alkyl and $V^4$ is —CONR$^{15}$—.

For example, $T^1$, $T^2$, $T^3$ and $T^4$ and $V^1$, $V^2$, $V^3$ and $V^4$ can be selected from the following:

$T^1$ is $CH_2CH_2$ and $V^1$ is —CO—;
$T^2$ is 4AP and $V^2$ is a covalent bond;
$T^3$ is $(PEG)_2$ and $V^3$ is —CONH—; and
$T^4$ is $CH_2CH_2$ and $V^4$ is —CONH—.

In certain embodiments, $T^1$, $T^2$, $T^3$ and $T^4$ and $V^1$, $V^2$, $V^3$ and $V^4$ are selected from the following:

$T^1$ is $(C_1-C_{12})$alkyl and $V^1$ is —CO—;
$T^2$ is 4AP and $V^2$ is a covalent bond;
$T^3$ is $(PEG)_n$ and $V^3$ is —CONR$^{15}$—; and
$T^4$ is $(C_1-C_{12})$alkyl and $V^4$ is —CO—.

For example, $T^1$, $T^2$, $T^3$ and $T^4$ and $V^1$, $V^2$, $V^3$ and $V^4$ can be selected from the following:

$T^1$ is $CH_2CH_2$ and $V^1$ is —CO—;
$T^2$ is 4AP and $V^2$ is a covalent bond;
$T^3$ is $(PEG)_2$ and $V^3$ is —CONH—; and
$T^4$ is $CH_2CH_2$ and $V^4$ is —CO—.

In certain embodiments, the first linker $L^1$ is described by the following structure:

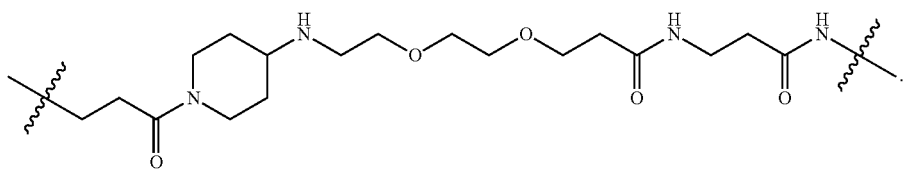 [SMILES: *CCC(=O)N1CCC(NCCOCCOCCC(=O)NCCC(=O)N*)CC1]

In certain embodiments, the first linker $L^1$ is described by the following structure:

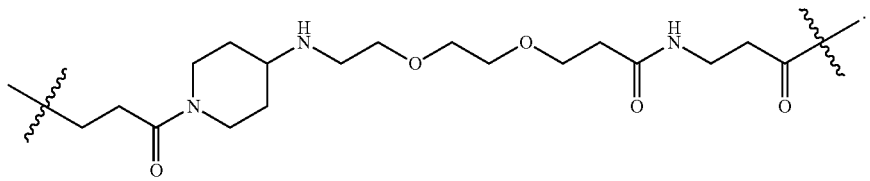 [SMILES: *CCC(=O)N1CCC(NCCOCCOCCC(=O)NCCC(*)=O)CC1]

In certain embodiments, the left-hand side of the above linker structures is attached to the hydrazinyl-indolyl or the hydrazinyl-pyrrolo-pyridinyl coupling moiety, and the right-hand side of the above linker structures is attached to the coupling moiety (e.g., the sulfatase-cleavable moiety, such as the sulfate-containing group).

In some embodiments, $L^2$ is a second linker described by the formula $-(L^{21})_e-(L^{22})_f-(L^{23})_g-(L^{24})_h-$, wherein $L^{21}$, $L^{22}$, $L^{23}$ and $L^{24}$ are each independently a second linker subunit, and e, f, g and h are each independently 0 or 1, wherein the sum of e, f, g and h is 0 to 4.

In certain embodiments, the sum of e, f, g and h is 0. In these instances, the second linker $L^2$ is not present. Stated another way, when the sum of e, f, g and h is 0, then the second linker $L^2$ is a covalent bond. In certain embodiments, the sum of e, f, g and h is 1. In certain embodiments, the sum of e, f, g and h is 2. In certain embodiments, the sum of e, f, g and h is 3. In certain embodiments, the sum of e, f, g and h is 4. In certain embodiments, e, f, g and h are each 1. In certain embodiments, e, f and g are each 1 and h is 0. In certain embodiments, e and f are each 1 and g and h are each 0. In certain embodiments, e is 1 and f, g and h are each 0.

In certain embodiments, $L^{21}$ is attached to the drug (e.g., $W^1$ as shown in formula (I) above). In certain embodiments, $L^{22}$, if present, is attached to the drug. In certain embodiments, $L^{23}$, if present, is attached to the drug. In certain embodiments, $L^{24}$, if present, is attached to the drug.

Any convenient linker subunits may be utilized in the second linker $L^2$. Linker subunits of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocyclic groups, combinations thereof, and substituted versions thereof. In some embodiments, each of $L^{21}$, $L^{22}$, $L^{23}$ and $L^{24}$ (if present) comprise one or more groups independently selected from a polyethylene glycol, a modified polyethylene glycol, an amino acid residue, an alkyl group, a substituted alkyl, an aryl group, a substituted aryl group, and a diamine (e.g., a linking group that includes an alkylene diamine).

In some embodiments, $L^{21}$ (if present) comprises a polyethylene glycol, a modified polyethylene glycol, an amino acid residue, an alkyl group, a substituted alkyl, an aryl group, a substituted aryl group, or a diamine. In some embodiments, $L^{21}$ comprises a polyethylene glycol. In some embodiments, $L^{21}$ comprises a modified polyethylene glycol. In some embodiments, $L^{21}$ comprises an amino acid residue. In some embodiments, $L^{21}$ comprises an alkyl group or a substituted alkyl. In some embodiments, $L^{21}$ comprises an aryl group or a substituted aryl group. In some embodiments, $L^{21}$ comprises a diamine (e.g., a linking group comprising an alkylene diamine).

In some embodiments, $L^{22}$ (if present) comprises a polyethylene glycol, a modified polyethylene glycol, an amino acid residue, an alkyl group, a substituted alkyl, an aryl group, a substituted aryl group, or a diamine. In some embodiments, $L^{22}$ comprises a polyethylene glycol. In some embodiments, $L^{22}$ comprises a modified polyethylene glycol. In some embodiments, $L^{22}$ comprises an amino acid residue. In some embodiments, $L^{22}$ comprises an alkyl group or a substituted alkyl. In some embodiments, $L^{22}$ comprises an aryl group or a substituted aryl group. In some embodiments, $L^{22}$ comprises a diamine (e.g., a linking group comprising an alkylene diamine).

In some embodiments, $L^{23}$ (if present) comprises a polyethylene glycol, a modified polyethylene glycol, an amino acid residue, an alkyl group, a substituted alkyl, an aryl group, a substituted aryl group, or a diamine. In some embodiments, $L^{23}$ comprises a polyethylene glycol. In some embodiments, $L^{23}$ comprises a modified polyethylene glycol. In some embodiments, $L^{23}$ comprises an amino acid residue. In some embodiments, $L^{23}$ comprises an alkyl group or a substituted alkyl. In some embodiments, $L^{23}$ comprises an aryl group or a substituted aryl group. In some embodiments, $L^{23}$ comprises a diamine (e.g., a linking group comprising an alkylene diamine).

In some embodiments, $L^{24}$ (if present) comprises a polyethylene glycol, a modified polyethylene glycol, an amino acid residue, an alkyl group, a substituted alkyl, an aryl group, a substituted aryl group, or a diamine. In some embodiments, $L^{24}$ comprises a polyethylene glycol. In some embodiments, $L^{24}$ comprises a modified polyethylene glycol. In some embodiments, $L^{24}$ comprises an amino acid residue. In some embodiments, $L^{24}$ comprises an alkyl group or a substituted alkyl. In some embodiments, $L^{24}$ comprises an aryl group or a substituted aryl group. In some embodiments, $L^{24}$ comprises a diamine (e.g., a linking group comprising an alkylene diamine).

In some embodiments, $L^2$ is a second linker comprising -$(L^{21})_e$-$(L^{22})_f$-$(L^{23})_g$-$(L^{24})_h$-, where:

-$(L^{21})_e$- is -$(T^5$-$V^5)_e$-;

-$(L^{22})_f$- is -$(T^6$-$V^6)_f$-;

-$(L^{23})_g$- is -$(T^7$-$V^7)_g$-; and

-$(L^{24})_h$- is -$(T^8$-$V^8)_h$-, wherein $T^5$, $T^6$, $T^7$ and $T^8$, if present, are tether groups;
$V^5$, $V^6$, $V^7$ and $V^8$, if present, are covalent bonds or linking functional groups; and
e, f, g and h are each independently 0 or 1, wherein the sum of e, f, g and h is 0 to 4.

In certain embodiments, $L^{21}$ is attached to the sulfatase-cleavable moiety (e.g., the sulfate-containing group as shown in formula (I) above). As such, in certain embodiments, $T^5$ is attached to the sulfatase-cleavable moiety (e.g., the sulfate-containing group). In certain embodiments, $V^5$ is attached to the drug (e.g., $W^1$ as shown in formula (I) above). In certain embodiments, $L^{22}$, if present, is attached to the drug. As such, in certain embodiments, $T^6$, if present, is attached to the drug, or $V^6$, if present, is attached to the drug. In certain embodiments, $L^{23}$, if present, is attached to the drug. As such, in certain embodiments, $T^7$, if present, is attached to the drug, or $V^7$, if present, is attached to the drug. In certain embodiments, $L^{24}$, if present, is attached to the drug. As such, in certain embodiments, $T^8$, if present, is attached to the drug, or $V^8$, if present, is attached to the drug.

Regarding the tether groups, $T^5$, $T^6$, $T^7$ and $T^8$, any convenient tether groups may be utilized in the subject linkers. In some embodiments, $T^5$, $T^6$, $T^7$ and $T^8$ each comprise one or more groups independently selected from a $(C_1$-$C_{12})$alkyl, a substituted $(C_1$-$C_{12})$alkyl, an $(EDA)_w$, $(PEG)_n$, $(AA)_p$, —$(CR^{13}OH)_h$—, piperidin-4-amino (4AP), an acetal group, a disulfide, a hydrazine, and an ester, where w is an integer from 1 to 20, n is an integer from 1 to 30, p is an integer from 1 to 20, and h is an integer from 1 to 12.

In certain embodiments, the tether group (e.g., $T^5$, $T^6$, $T^7$ and/or $T^8$) includes a $(C_1$-$C_{12})$alkyl or a substituted $(C_1$-$C_{12})$alkyl. In certain embodiments, $(C_1$-$C_{12})$alkyl is a straight chain or branched alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, $(C_1$-$C_{12})$alkyl may be an alkyl or substituted alkyl, such as $C_1$-$C_{12}$ alkyl, or $C_1$-$C_{10}$ alkyl, or $C_1$-$C_6$ alkyl, or $C_1$-$C_3$ alkyl. In some instances, $(C_1$-$C_{12})$alkyl is a $C_2$-alkyl. For example, $(C_1$-$C_{12})$alkyl may be an alkylene or substituted alkylene, such as $C_1$-$C_{12}$ alkylene, or $C_1$-$C_{10}$ alkylene, or $C_1$-$C_6$ alkylene, or $C_1$-$C_3$ alkylene. In some instances, $(C_1$-$C_{12})$alkyl is a $C_2$-alkylene (e.g., $CH_2CH_2$). In some instances, $(C_1$-$C_{12})$alkyl is a $C_1$-alkylene (e.g., $CH_2$).

In certain embodiments, substituted $(C_1$-$C_{12})$alkyl is a straight chain or branched substituted alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, substituted $(C_1$-$C_{12})$alkyl may be a substituted alkyl, such as substituted $C_1$-$C_{12}$ alkyl, or substituted $C_1$-$C_{10}$ alkyl, or substituted $C_1$-$C_6$ alkyl, or substituted $C_1$-$C_3$ alkyl. In some instances, substituted $(C_1$-$C_{12})$alkyl is a substituted $C_2$-alkyl. For example, substituted $(C_1$-$C_{12})$alkyl may be a substituted alkylene, such as substituted $C_1$-$C_{12}$ alkylene, or substituted $C_1$-$C_{10}$ alkylene, or substituted $C_1$-$C_6$ alkylene, or substituted $C_1$-$C_3$ alkylene. In some instances, substituted $(C_1$-$C_{12})$alkyl is a substituted $C_2$-alkylene. In some instances, substituted $(C_1$-$C_{12})$alkyl is a substituted $C_1$-alkylene.

In certain embodiments, the tether group (e.g., $T^5$, $T^6$, $T^7$ and/or $T^8$) includes an ethylene diamine (EDA) moiety, e.g., an EDA moiety as described above, such as an EDA moiety described by the structure:

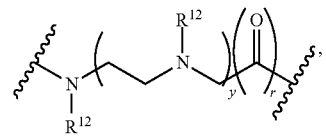

where y is an integer from 1 to 6, or is 0 or 1, and each $R^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, y is 1, 2, 3, 4, 5 or 6. In certain embodiments, y is 1 and r is 0. In certain embodiments, y is 1 and r is 1. In certain embodiments, y is 2 and r is 0. In certain embodiments, y is 2 and r is 1. In certain embodiments, each $R^{12}$ is independently selected from hydrogen, an alkyl, a substituted alkyl, an aryl and a substituted aryl. In certain embodiments, any two adjacent $R^{12}$ groups of the EDA may be cyclically linked, e.g., to form a piperazinyl ring. In certain embodiments, y is 1 and the two adjacent $R^{12}$ groups are an alkyl group, cyclically linked to form a piperazinyl ring. In certain embodiments, y is 1 and the adjacent $R^{12}$ groups are selected from hydrogen, an alkyl (e.g., methyl) and a substituted alkyl (e.g., lower alkyl-OH, such as ethyl-OH or propyl-OH).

In certain embodiments, the tether group (e.g., $T^5$, $T^6$, $T^7$ and/or $T^8$) includes a 4-amino-piperidine (4AP) moiety as described above, such as a 4AP moiety described by the structure:

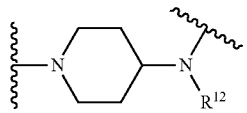

where $R^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is a polyethylene glycol moiety. In certain embodiments, $R^{12}$ is a carboxy modified polyethylene glycol.

In certain embodiments, $R^{12}$ includes a polyethylene glycol moiety described by the formula: $(PEG)_k$, which may be represented by the structure:

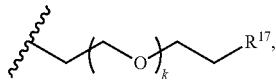

where k is an integer from 1 to 20, such as from 1 to 18, or from 1 to 16, or from 1 to 14, or from 1 to 12, or from 1 to 10, or from 1 to 8, or from 1 to 6, or from 1 to 4, or 1 or 2, such as 1, 2, 3, 4, 5, 6, 7, 8, 9, 10, 11, 12, 13, 14, 15, 16, 17, 18, 19 or 20. In some instances, k is 2. In certain embodiments, $R^{17}$ is selected from OH, COOH, or COOR, where R is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{17}$ is COOH.

In certain embodiments, a tether group (e.g., $T^5$, $T^6$, $T^7$ and/or $T^8$) includes a polyethylene glycol moiety $(PEG)_n$ as described above, such as a $(PEG)_n$ moiety described by the structure:

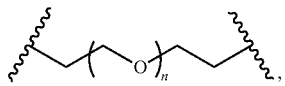

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 2. In some instances, n is 3. In some instances, n is 6. In some instances, n is 12.

In certain embodiments, a tether group (e.g., $T^5$, $T^6$, $T^7$ and/or $T^8$) includes $(AA)_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In certain embodiments, p is 1. In certain embodiments, p is 2.

In certain embodiments, a tether group (e.g., $T^5$, $T^6$, $T^7$ and/or $T^8$) includes a moiety described by the formula $-(CR^{13}OH)_h-$, where h is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, h is 1. In certain embodiments, h is 2. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{13}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{13}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{13}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{13}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^{13}$ is selected from hydrogen, an alkyl, a substituted alkyl, an aryl, and a substituted aryl. In these embodiments, alkyl, substituted alkyl, aryl, and substituted aryl are as described above for $R^{13}$.

Regarding the linking functional groups, $V^5$, $V^6$, $V^7$ and $V^8$, any convenient linking functional groups may be utilized in the second linker $L^2$. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoramidate, and the like. In some embodiments, $V^5$, $V^6$, $V^7$ and $V^8$ are each independently selected from a covalent bond, $-CO-$, $-NR^{15}-$, $-NR^{15}(CH_2)_q-$, $-NR^{15}(C_6H_4)-$, $-CONR^{15}-$, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, where q is an integer from 1 to 6. In certain embodiments, q is an integer from 1 to 6 (e.g., 1, 2, 3, 4, 5 or 6). In certain embodiments, q is 1. In certain embodiments, q is 2.

In some embodiments, each R$^{15}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each R$^{15}$ are described in more detail as follows. In certain embodiments, R$^{15}$ is hydrogen. In certain embodiments, each R$^{15}$ is hydrogen. In certain embodiments, R$^{15}$ is alkyl or substituted alkyl, such as C$_{1-6}$ alkyl or C$_{1-6}$ substituted alkyl, or C$_{1-4}$ alkyl or C$_{1-4}$ substituted alkyl, or C$_{1-3}$ alkyl or C$_{1-3}$ substituted alkyl. In certain embodiments, R$^{15}$ is alkenyl or substituted alkenyl, such as C$_{2-6}$ alkenyl or C$_{2-6}$ substituted alkenyl, or C$_{2-4}$ alkenyl or C$_{2-4}$ substituted alkenyl, or C$_{2-3}$ alkenyl or C$_{2-3}$ substituted alkenyl. In certain embodiments, R$^{15}$ is alkynyl or substituted alkynyl. In certain embodiments, R$^{15}$ is alkoxy or substituted alkoxy. In certain embodiments, R$^{15}$ is amino or substituted amino. In certain embodiments, R$^{15}$ is carboxyl or carboxyl ester. In certain embodiments, R$^{15}$ is acyl or acyloxy. In certain embodiments, R$^{15}$ is acyl amino or amino acyl. In certain embodiments, R$^{15}$ is alkylamide or substituted alkylamide. In certain embodiments, R$^{15}$ is sulfonyl. In certain embodiments, R$^{15}$ is thioalkoxy or substituted thioalkoxy. In certain embodiments, R$^{15}$ is aryl or substituted aryl, such as C$_{5-8}$ aryl or C$_{5-8}$ substituted aryl, such as a C$_5$ aryl or C$_5$ substituted aryl, or a C$_6$ aryl or C$_6$ substituted aryl. In certain embodiments, R$^{15}$ is heteroaryl or substituted heteroaryl, such as C$_{5-8}$ heteroaryl or C$_{5-8}$ substituted heteroaryl, such as a C$_5$ heteroaryl or C$_5$ substituted heteroaryl, or a C$_6$ heteroaryl or C$_6$ substituted heteroaryl. In certain embodiments, R$^{15}$ is cycloalkyl or substituted cycloalkyl, such as C$_{3-8}$ cycloalkyl or C$_{3-8}$ substituted cycloalkyl, such as a C$_{3-6}$ cycloalkyl or C$_{3-6}$ substituted cycloalkyl, or a C$_{3-5}$ cycloalkyl or C$_{3-5}$ substituted cycloalkyl. In certain embodiments, R$^{15}$ is heterocyclyl or substituted heterocyclyl, such as C$_{3-8}$ heterocyclyl or C$_{3-8}$ substituted heterocyclyl, such as a C$_{3-6}$ heterocyclyl or C$_{3-6}$ substituted heterocyclyl, or a C$_{3-5}$ heterocyclyl or C$_{3-5}$ substituted heterocyclyl.

In certain embodiments, each R$^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, the hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl substituents are as described above for R$^{15}$.

In certain embodiments, the tether group includes an acetal group, a disulfide, a hydrazine, or an ester. In some embodiments, the tether group includes an acetal group. In some embodiments, the tether group includes a disulfide. In some embodiments, the tether group includes a hydrazine. In some embodiments, the tether group includes an ester.

As described above, in some embodiments, L$^2$ is a second linker comprising -(T$^5$-V$^5$)$_e$-(T$^6$-V$^6$)$_f$-(T$^7$-V$^7$)$_g$-(T$^8$-V$^8$)$_h$—, where e, f, g and h are each independently 0 or 1, where the sum of e, f, g and h is 0 to 4.

In some embodiments, in the second linker L$^2$:
T$^5$, T$^6$, T$^7$ and T$^8$ are each independently selected from (C$_1$-C$_{12}$)alkyl, substituted (C$_1$-C$_{12}$)alkyl, (EDA)$_w$, (PEG)$_n$, (AA)$_p$, —(CR$^{13}$OH)$_h$—, 4-amino-piperidine (4AP), an acetal group, a disulfide, a hydrazine, and an ester; and V$^5$, V$^6$, V$^7$ and V$^8$ are each independently selected from a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein q is an integer from 1 to 6;

wherein:
(PEG)$_n$ is

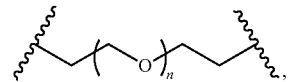

where n is an integer from 1 to 30;
EDA is an ethylene diamine moiety having the following structure:

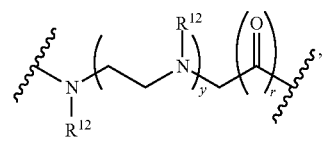

where y is an integer from 1 to 6 and r is 0 or 1;
4-amino-piperidine (4AP) is

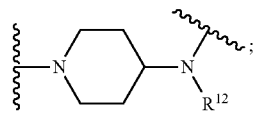

AA is an amino acid residue, where p is an integer from 1 to 20;
each R$^{13}$ is independently selected from hydrogen, an alkyl, a substituted alkyl, an aryl, and a substituted aryl; and each R$^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In certain embodiments, T$^5$, T$^6$, T$^7$ and T$^8$ and V$^5$, V$^6$, V$^7$ and V$^8$ are selected from the following:
T$^5$ is (C$_1$-C$_{12}$)alkyl and V$^5$ is —OC(O)—;
T$^6$ and V$^6$ are not present;
T$^7$ and V$^7$ are not present; and
T$^8$ and V$^8$ are not present.
For example, T$^5$, T$^6$, T$^7$ and T$^8$ and V$^5$, V$^6$, V$^7$ and V$^8$ can be selected from the following:
T$^5$ is CH$_2$ and V$^5$ is —OC(O)—;
T$^6$ and V$^6$ are not present;

$T^7$ and $V^7$ are not present; and $T^8$ and $V^8$ are not present.

In certain embodiments, $T^5$, $T^6$, $T^7$ and $T^8$ and $V^5$, $V^6$, $V^7$ and $V^8$ are not present (i.e., the sum of e, f, g, and h is 0).

In certain embodiments, the second linker $L^2$ is described by the following structure:

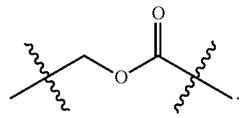 [SMILES: *COC(*)=O]

In certain embodiments, the left-hand side of the above linker structure is attached to the sulfatase-cleavable moiety (e.g., sulfate-containing group), and the right-hand side of the above linker structures is attached to the drug.

Any of the chemical entities, linkers and coupling moieties set forth in the structures above may be adapted for use in the subject compounds and conjugates.

Additional disclosure related to hydrazinyl-indolyl and hydrazinyl-pyrrolo-pyridinyl compounds and methods for producing a conjugate is found in U.S. Application Publication No. 2014/0141025, filed Mar. 11, 2013, and U.S. Application Publication No. 2015/0157736, filed Nov. 26, 2014, the disclosures of each of which are incorporated herein by reference.

Compounds Useful for Producing Conjugates

The present disclosure provides hydrazinyl-indolyl and hydrazinyl-pyrrolo-pyridinyl compounds useful for producing the conjugates described herein. In certain embodiments, the hydrazinyl-indolyl or hydrazinyl-pyrrolo-pyridinyl compound may be a coupling moiety useful for conjugation of an antibody and a drug. For example, the hydrazinyl-indolyl or hydrazinyl-pyrrolo-pyridinyl compound may be bound to the antibody and also bound to the drug, thus indirectly binding the antibody and the drug together.

In certain embodiments, the compound is a compound of formula (II):

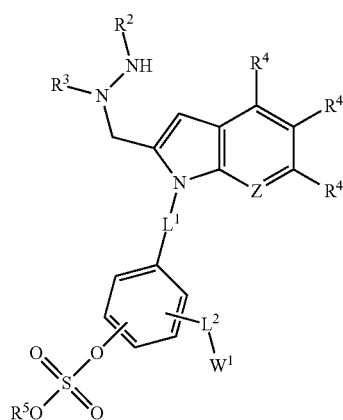

wherein

Z is $CR^4$ or N;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$R^5$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$L^1$ is a first linker;

$L^2$ is a second linker; and $W^1$ is a drug.

For example, the compound may be a compound of formula (IIa):

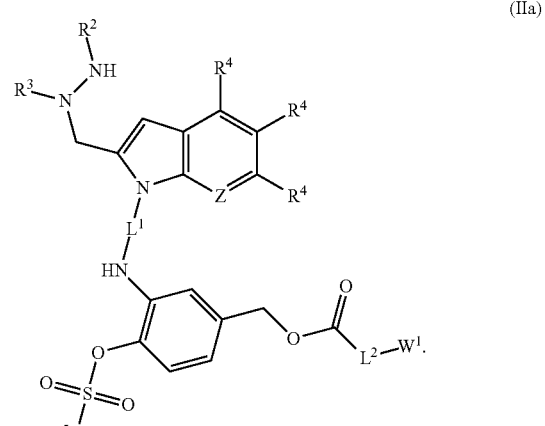

In some instances, the compound may be a compound of formula (IIb):

(IIb)

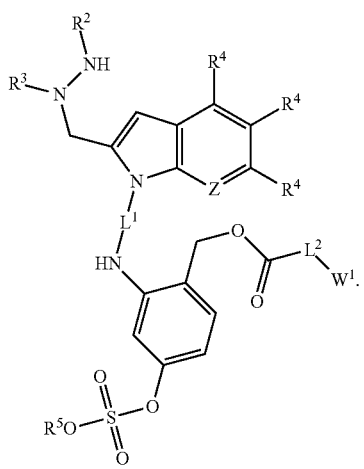

In some instances, the compound may be a compound of formula (IId):

(IId)

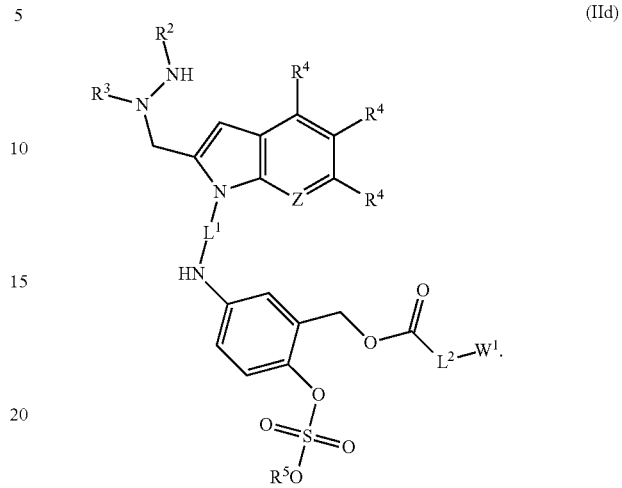

In some instances, the compound may be a compound of formula (IIe):

(IIe)

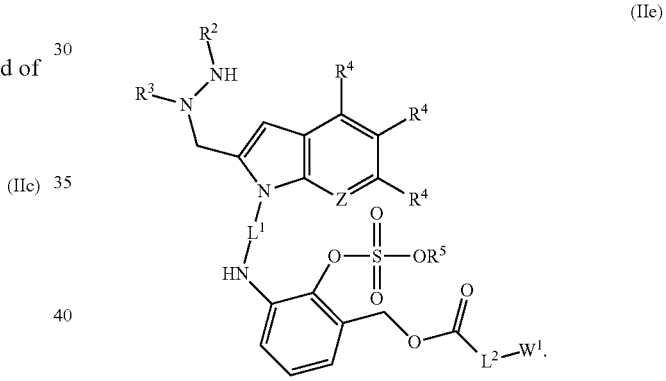

In some instances, the compound may be a compound of formula (IIc):

(IIc)

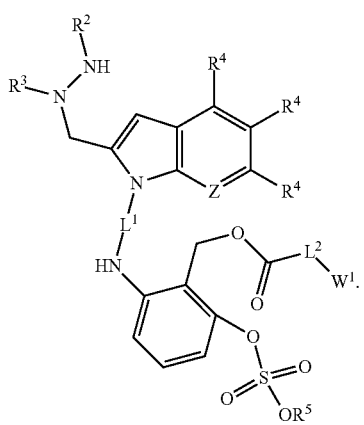

The substituents related to conjugates of formula (II) are described herein. References to formula (II) are intended to also encompass formulae (IIa), (IIb), (IIc), (IId), and (IIe).

Regarding compound of formula (II), the substituents Z, $R^2$, $R^3$, $R^4$, $R^5$, $L^1$, $L^2$, and $W^1$ are as described above in relation to the conjugates of formula (I). Similarly, regarding the first linker $L^1$ and the second linker $L^2$ of formula (II), the $T^1$, $T^2$, $T^3$, $T^4$, $V^1$, $V^2$, $V^3$ and $V^4$, and $T^5$, $T^6$, $T^7$, $T^8$, $V^5$, $V^6$, $V^7$ and $V^8$ substituents are as described above in relation to the conjugates of formula (I).

In certain embodiments, the compound is of the following structure:

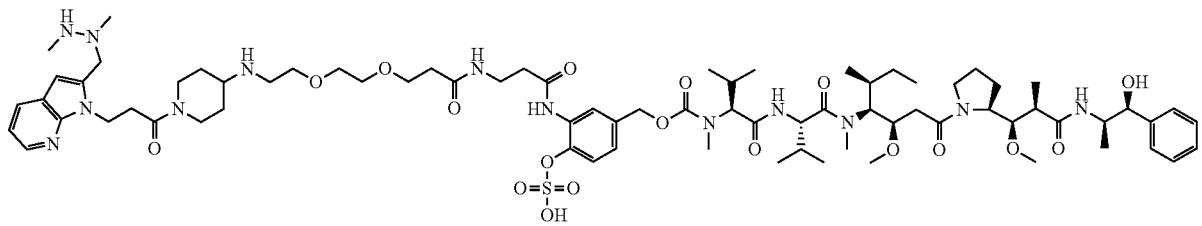 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(OS(=O)(=O)O)c(NC(=O)CCNC(=O)CCOCCOCCNC2CCN(C(=O)CCn3c(CN(C)NC)cc4cccnc43)CC2)c1)C(C)C]

In certain embodiments, the compound is of the following structure:

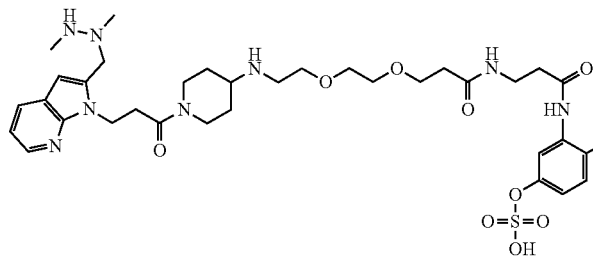

Antibodies

As noted above, a subject conjugate can comprise as substituent W² an antibody, where the antibody has been modified to include a 2-formylglycine (FGly) residue. As used herein, amino acids may be referred to by their standard name, their standard three letter abbreviation and/or their standard one letter abbreviation, such as: Alanine or Ala or A; Cysteine or Cys or C; Aspartic acid or Asp or D; Glutamic acid or Glu or E; Phenylalanine or Phe or F; Glycine or Gly or G; Histidine or His or H; Isoleucine or Ile or I; Lysine or Lys or K; Leucine or Leu or L; Methionine or Met or M; Asparagine or Asn or N; Proline or Pro or P; Glutamine or Gln or Q; Arginine or Arg or R; Serine or Ser or S; Threonine or Thr or T; Valine or Val or V; Tryptophan or Trp or W; and Tyrosine or Tyr or Y.

In certain embodiments, the amino acid sequence of an antibody is modified to include a sulfatase motif that contains a serine or cysteine residue that is capable of being converted (oxidized) to a 2-formylglycine (FGly) residue by action of a formylglycine generating enzyme (FGE) either in vivo (e.g., at the time of translation of an aldehyde tag-containing protein in a cell) or in vitro (e.g., by contacting an aldehyde tag-containing protein with an FGE in a cell-free system). Such sulfatase motifs may also be referred to herein as an FGE-modification site.

Sulfatase Motifs

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8, 7 or 6 amino acid residues in length.

In certain embodiments, polypeptides of interest include those where one or more amino acid residues, such as 2 or more, or 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, or 16 or more, or 17 or more, or 18 or more, or 19 or more, or 20 or more amino acid residues have been inserted, deleted, substituted (replaced) relative to the native amino acid sequence to provide for a sequence of a sulfatase motif in the polypeptide. In certain embodiments, the polypeptide includes a modification (insertion, addition, deletion, and/or substitution/replacement) of less than 20, 19, 18, 17, 16, 15, 14, 13, 12, 11, 10, 9, 8, 7, 6, 5, 4, 3 or 2 amino acid residues of the amino acid sequence relative to the native amino acid sequence of the polypeptide. Where an amino acid sequence native to the polypeptide (e.g., antibody) contains one or more residues of the desired sulfatase motif, the total number of modifications of residues can be reduced, e.g., by site-specification modification (insertion, addition, deletion, substitution/replacement) of amino acid residues flanking the native amino acid residues to provide a sequence of the desired sulfatase motif. In certain embodiments, the extent of modification of the native amino acid sequence of the target antibody is minimized, so as to minimize the number of amino acid residues that are inserted, deleted, substituted (replaced), or added (e.g., to the N- or C-terminus). Minimizing the extent of amino acid sequence modification of the target antibody may minimize the impact such modifications may have upon antibody function and/or structure.

It should be noted that while aldehyde tags of particular interest are those comprising at least a minimal sulfatase motif (also referred to a "consensus sulfatase motif"), it will be readily appreciated that longer aldehyde tags are both contemplated and encompassed by the present disclosure and can find use in the compositions and methods of the present disclosure. Aldehyde tags can thus comprise a minimal sulfatase motif of 5 or 6 residues, or can be longer and comprise a minimal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

An aldehyde tag can be present at or near the C-terminus of an Ig heavy chain; e.g., an aldehyde tag can be present within 1, 2, 3, 4, 5, 6, 7, 8, 9, or 10 amino acids of the C-terminus of a native, wild-type Ig heavy chain. An aldehyde tag can be present within a CH1 domain of an Ig heavy chain. An aldehyde tag can be present within a CH2 domain of an Ig heavy chain. An aldehyde tag can be present within a CH3 domain of an Ig heavy chain. An aldehyde tag can be present in an Ig light chain constant region, e.g., in a kappa light chain constant region or a lambda light chain constant region.

In certain embodiments, the sulfatase motif used may be described by the formula:

$$X^1Z^{10}X^2Z^{20}X^3Z^{30} \qquad (I')$$

where $Z^{10}$ is cysteine or serine (which can also be represented by (C/S));

$Z^{20}$ is either a proline or alanine residue (which can also be represented by (P/A));

$Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I;

$X^1$ is present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M, S or V, with the proviso that when the sulfatase motif is at the N-terminus of the target polypeptide, $X^1$ is present; and $X^2$ and $X^3$ independently can be any amino acid, though usually an aliphatic amino acid, a polar, uncharged amino acid, or a sulfur containing amino acid (i.e., other than an aromatic amino acid or a charged amino acid), e.g., S, T, A, V, G or C, e.g., S, T, A, V or G.

The amino acid sequence of an antibody heavy and/or light chain can be modified to provide a sequence of at least 5 amino acids of the formula $X^1Z^{10}X^2Z^{20}X^3Z^{30}$, where $Z^{10}$ is cysteine or serine;

$Z^{20}$ is a proline or alanine residue;

$Z^{30}$ is an aliphatic amino acid or a basic amino acid;

$X^1$ is present or absent and, when present, is any amino acid, with the proviso that when the heterologous sulfatase motif is at an N-terminus of the polypeptide, $X^1$ is present;

$X^2$ and $X^3$ are each independently any amino acid.

The sulfatase motif is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

For example, where the FGE is a eukaryotic FGE (e.g., a mammalian FGE, including a human FGE), the sulfatase motif can be of the formula:

$$X^1CX^2PX^3Z^{30} \quad (I'')$$

where $X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, S or V, with the proviso that when the sulfatase motif is at the N-terminus of the target polypeptide, $X^1$ is present;

$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G, or C, e.g., S, T, A, V or G; and $Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I.

Specific examples of sulfatase motifs include LCTPSR (SEQ ID NO://), MCTPSR (SEQ ID NO://), VCTPSR (SEQ ID NO://), LCSPSR (SEQ ID NO://), LCAPSR (SEQ ID NO://), LCVPSR (SEQ ID NO://), LCGPSR (SEQ ID NO://), ICTPAR (SEQ ID NO://), LCTPSK (SEQ ID NO://), MCTPSK (SEQ ID NO://), VCTPSK (SEQ ID NO://), LCSPSK (SEQ ID NO://), LCAPSK (SEQ ID NO://), LCVPSK (SEQ ID NO://), LCGPSK (SEQ ID NO://), LCTPSA (SEQ ID NO://), ICTPAA (SEQ ID NO://), MCTPSA (SEQ ID NO://), VCTPSA (SEQ ID NO://), LCSPSA (SEQ ID NO://), LCAPSA (SEQ ID NO://), LCVPSA (SEQ ID NO://), and LCGPSA (SEQ ID NO://).

FGly-Containing Sequences

Upon action of FGE on the modified antibody heavy and/or light chain, the serine or the cysteine in the sulfatase motif is modified to FGly. Thus, the FGly-containing sulfatase motif can be of the formula:

$$X^1(FGly)X^2Z^{20}X^3Z^{30} \quad (I''')$$

where

FGly is the formylglycine residue;

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and $X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

As described above, the modified polypeptide containing the FGly residue may be conjugated to a drug (e.g., a maytansinoid) by reaction of the FGly with the drug (e.g., a drug containing a hydrazinyl-indolyl or a hydrazinyl-pyrrolo-pyridinyl coupling moiety, as described above) to produce an FGly'-containing sulfatase motif. As used herein, the term FGly' refers to the modified amino acid residue of the sulfatase motif that is coupled to the drug, such as a maytansine or an auristatin. Thus, the FGly'-containing sulfatase motif can be of the formula:

$$X^1(FGly')X^2Z^{20}X^3Z^{30} \quad (II)$$

where

FGly' is the modified amino acid residue of formula (I);

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and $X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

Site of Modification

As noted above, the amino acid sequence of an antibody is modified to include a sulfatase motif that contains a serine or cysteine residue that is capable of being converted (oxidized) to an FGly residue by action of an FGE either in vivo (e.g., at the time of translation of an aldehyde tag-containing protein in a cell) or in vitro (e.g., by contacting an aldehyde tag-containing protein with an FGE in a cell-free system). The antibody used to generate a conjugate of the present disclosure include at least an Ig constant region, e.g., an Ig heavy chain constant region (e.g., at least a CH1 domain; at least a CH1 and a CH2 domain; a CH1, a CH2, and a CH3 domain; or a CH1, a CH2, a CH3, and a CH4 domain), or an Ig light chain constant region. Such Ig polypeptides are referred to herein as "target Ig polypeptides" or "target antibodies".

The site in an antibody into which a sulfatase motif is introduced can be any convenient site. As noted above, in some instances, the extent of modification of the native amino acid sequence of the target polypeptide is minimized, so as to minimize the number of amino acid residues that are inserted, deleted, substituted (replaced), and/or added (e.g., to the N- or C-terminus). Minimizing the extent of amino acid sequence modification of the target antibody may minimize the impact such modifications may have upon antibody function and/or structure.

An antibody heavy chain constant region can include Ig constant regions of any heavy chain isotype, non-naturally occurring Ig heavy chain constant regions (including consensus Ig heavy chain constant regions). An Ig constant region can be modified to include an aldehyde tag, where the aldehyde tag is present in or adjacent a solvent-accessible loop region of the Ig constant region. An Ig constant region can be modified by insertion and/or substitution of 1, 2, 3, 4, 5, 6, 7, 8, 9, 10, 11, 12, 13, 14, 15, or 16 amino acids, or more than 16 amino acids, to provide an amino acid sequence of a sulfatase motif as described above.

In some cases, an aldehyde-tagged antibody comprises an aldehyde-tagged Ig heavy chain constant region (e.g., at least a CH1 domain; at least a CH1 and a CH2 domain; a CH1, a CH2, and a CH3 domain; or a CH1, a CH2, a CH3, and a CH4 domain). The aldehyde-tagged Ig heavy chain constant region can include heavy chain constant region sequences of an IgA, IgM, IgD, IgE, IgG1, IgG2, IgG3, or IgG4 isotype heavy chain or any allotypic variant of same, e.g., human heavy chain constant region sequences or mouse heavy chain constant region sequences, a hybrid heavy chain constant region, a synthetic heavy chain constant region, or a consensus heavy chain constant region sequence, etc., modified to include at least one sulfatase motif that can be modified by an FGE to generate an FGly-modified Ig polypeptide. Allotypic variants of Ig heavy chains are known in the art. See, e.g., Jefferis and Lefranc (2009) *MAbs* 1:4.

In some cases, an aldehyde-tagged antibody comprises an aldehyde-tagged Ig light chain constant region. The aldehyde-tagged Ig light chain constant region can include constant region sequences of a kappa light chain, a lambda light chain, e.g., human kappa or lambda light chain constant regions, a hybrid light chain constant region, a synthetic light chain constant region, or a consensus light chain constant region sequence, etc., modified to include at least one sulfatase motif that can be modified by an FGE to generate an FGly-modified antibody. Exemplary constant regions include human gamma 1 and gamma 3 regions. With the exception of the sulfatase motif, a modified constant region may have a wild-type amino acid sequence, or it may have an amino acid sequence that is at least 70% identical (e.g., at least 80%, at least 90% or at least 95% identical) to a wild type amino acid sequence.

In some embodiments the sulfatase motif is at a position other than, or in addition to, the C-terminus of the Ig polypeptide heavy chain. As noted above, an isolated aldehyde-tagged antibody can comprise a heavy chain constant region modified to include a sulfatase motif as described above, where the sulfatase motif is in or adjacent a surface-accessible loop region of the antibody heavy chain constant region.

A sulfatase motif can be provided within or adjacent one or more of these amino acid sequences of such modification sites of an Ig heavy chain. For example, an Ig heavy chain polypeptide can be modified (e.g., where the modification includes one or more amino acid residue insertions, deletions, and/or substitutions) at one or more of these amino acid sequences to provide a sulfatase motif adjacent and N-terminal and/or adjacent and C-terminal to these modification sites. Alternatively or in addition, an Ig heavy chain polypeptide can be modified (e.g., where the modification includes one or more amino acid residue insertions, deletions, and/or substitutions) at one or more of these amino acid sequences to provide a sulfatase motif between any two residues of the Ig heavy chain modifications sites. In some embodiments, an Ig heavy chain polypeptide may be modified to include two motifs, which may be adjacent to one another, or which may be separated by one, two, three, four or more (e.g., from about 1 to about 25, from about 25 to about 50, or from about 50 to about 100, or more, amino acids. Alternatively or in addition, where a native amino acid sequence provides for one or more amino acid residues of a sulfatase motif sequence, selected amino acid residues of the modification sites of an Ig heavy chain polypeptide amino acid sequence can be modified (e.g., where the modification includes one or more amino acid residue insertions, deletions, and/or substitutions) so as to provide a sulfatase motif at the modification site.

An antibody used in an antibody-drug conjugate of the present disclosure can have any of a variety of antigen-binding specificities, including but not limited to, e.g., an antigen present on a cancer cell; an antigen present on an autoimmune cell; an antigen present on a pathogenic microorganism; an antigen present on a virus-infected cell (e.g., a human immunodeficiency virus-infected cell); an antigen present on a diseased cell; and the like. For example, an antibody conjugate can bind an antigen, where the antigen is present on the surface of the cell. An antibody conjugate of the present disclosure can bind antigen with a suitable binding affinity, e.g., from $5 \times 10^{-6}$ M to $10^{-7}$ M, from $10^{-7}$ M to $5 \times 10^{-7}$ M, from $5 \times 10^{-7}$ M to $10^{-8}$ M, from $10^{-8}$ M to $5 \times 10^{-8}$ M, from $5 \times 10^{-8}$ M to $10^{-9}$ M, or a binding affinity greater than $10^{-9}$ M.

As non-limiting examples, a subject antibody conjugate can bind an antigen present on a cancer cell (e.g., a tumor-specific antigen; an antigen that is over-expressed on a cancer cell; etc.), and the conjugated moiety can be a drug, such as a cytotoxic compound (e.g., a cytotoxic small molecule, a cytotoxic synthetic peptide, etc.). For example, a subject antibody conjugate can be specific for an antigen on a cancer cell, where the conjugated moiety is a drug, such as a cytotoxic compound (e.g., a cytotoxic small molecule, a cytotoxic synthetic peptide, etc.).

As further non-limiting examples, a subject antibody conjugate can bind an antigen present on a cell infected with a virus (e.g., where the antigen is encoded by the virus; where the antigen is expressed on a cell type that is infected by a virus; etc.), and the conjugated moiety can be a drug, such as a viral fusion inhibitor. For example, a subject antibody conjugate can bind an antigen present on a cell infected with a virus, and the conjugated moiety can be a drug, such as a viral fusion inhibitor.

Drugs for Conjugation to a Polypeptide

The present disclosure provides drug-polypeptide conjugates (e.g., antibody-drug conjugates). Any of a number of drugs are suitable for use, or can be modified to be rendered suitable for use, as a reactive partner to conjugate to an antibody. Examples of drugs include small molecule drugs and peptide drugs.

"Small molecule drug" as used herein refers to a compound, e.g., an organic compound, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight. Suitable peptides include, but are not limited to, cytotoxic peptides; angiogenic peptides; anti-angiogenic peptides; peptides that activate B cells; peptides that activate T cells; anti-viral peptides; peptides that inhibit viral fusion; peptides that increase production of one or more lymphocyte populations; anti-microbial peptides; growth factors; growth hormone-releasing factors; vasoactive peptides; anti-inflammatory peptides; peptides that regulate glucose metabolism; an anti-thrombotic peptide; an anti-nociceptive peptide; a vasodilator peptide; a platelet aggregation inhibitor; an analgesic; and the like.

Examples of drugs include small molecule drugs, such as a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used.

Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD)).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethiylenethiophosphoramide, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxazine biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N- desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

In certain embodiments, the drug is an antimitotic agent, such as an auristatin or an active auristatin analog or derivative thereof (e.g., Monomethyl auristatin D (MMAD), monomethyl auristatin E (MMAE), monomethyl auristatin F (MMAF), and the like). In certain embodiments, the drug is MMAE, which has the following structure:

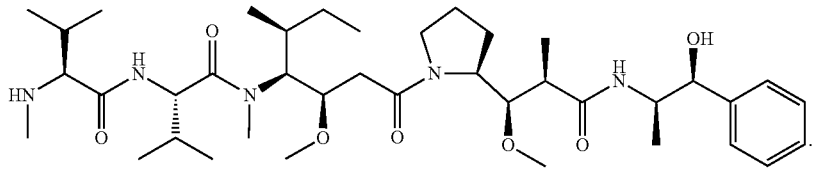

For example, the MMAE active agent can be included in an antibody-drug conjugate as follows:

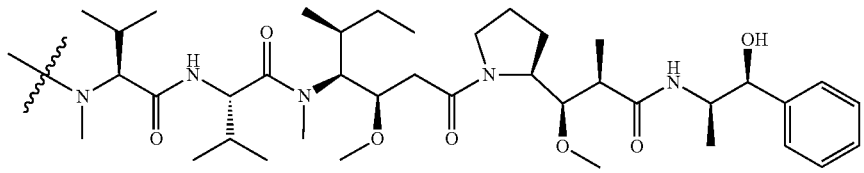 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

where ∼∼ indicates the point of attachment between the auristatin and the second linker, $L^2$, in formula (I). For example, the ∼∼ symbol indicates the bond between the N of the auristatin and the second linker, $L^2$, e.g., as shown in formula (I). For instance, in formula (I), $W^2$ can be an auristatin, such as MMAE, where ∼∼ in the structure above indicates the point of attachment between MMAE and the linker, $L^2$.

In certain embodiments, the drug is a microtubule affecting agent that has antiproliferative activity, such as a maytansine or a maytansinoid. In certain embodiments, the drug is a maytansine or a maytansinoid, which as the following structure:

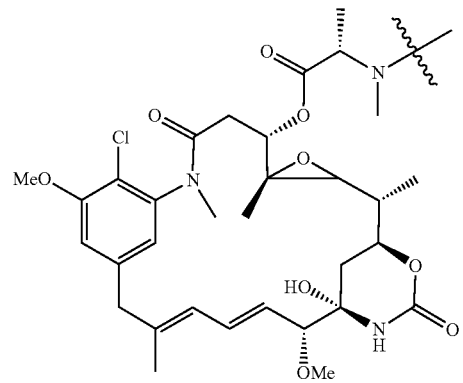

where ∼∼ indicates the point of attachment between the maytansine and the second linker, $L^2$, in formula (I). For example, the ∼∼ symbol indicates the bond between the N of the maytansine and the linker, $L^2$, e.g., as shown in formula (I). For instance, in formula (I), $W^2$ can be a maytansine, such as a maytansinoid of the structure above, where ∼∼ indicates the point of attachment between the maytansinoid and the linker, $L^2$. As shown in the structure above, in certain embodiments, the drug is deacyl maytansine.

As described above, in certain embodiments, $L^2$ is a second linker described by the formula -$(L^{21})_e$-$(L^{22})_f$-$(L^{23})_g$-$(L^{24})_h$-, wherein $L^{21}$, $L^{22}$, $L^{23}$ and $L^{24}$ are each independently a second linker subunit. In certain embodiments, $L^{21}$ is attached to the sulfatase-cleavable moiety, such as a sulfate-containing group (e.g., as shown in formula (I) above). In certain embodiments, if present, is also attached to $W^1$ (the drug). In certain embodiments, $L^{22}$, if present, is attached to $W^1$ (the drug). In certain embodiments, $L^{23}$, if present, is attached to $W^1$ (the drug). In certain embodiments, $L^{24}$, if present, is attached to $W^1$ (the drug).

As described above, in certain embodiments, the second linker -$(L^{21})_e$-$(L^{22})_f$-$(L^{23})_g$-$(L^{24})_h$- is described by the formula -$(T^5$-$V^5)_e$-$(T^6$-$V^6)_f$-$(T^7$-$V^7)_g$-$(T^8$-$V^8)_h$—, where e, f, g and h are each independently 0 or 1, where the sum of e, f, g and h is 0 to 4. In certain embodiments, as described above, $L^{21}$ is attached to the sulfatase-cleavable moiety (e.g., the sulfate-containing group as shown in formula (I) above). As such, in certain embodiments, $T^5$ is attached to the sulfatase-cleavable moiety (e.g., the sulfate-containing group as shown in formula (I) above). In certain embodiments, $V^5$ is attached to $W^1$ (the drug). In certain embodiments, as described above, $L^{22}$, if present, is attached to $W^1$ (the drug). As such, in certain embodiments, $T^6$, if present, is attached to $W^1$ (the drug), or $V^6$, if present, is attached to $W^1$ (the drug). In certain embodiments, as described above, $L^{23}$, if present, is attached to $W^1$ (the drug). As such, in certain embodiments, $T^7$, if present, is attached to $W^1$ (the drug), or $V^7$, if present, is attached to $W^1$ (the drug). In certain embodiments, as described above, $L^{24}$, if present, is attached to $W^1$ (the drug). As such, in certain embodiments, $T^8$, if present, is attached to $W^1$ (the drug), or $V^8$, if present, is attached to $W^1$ (the drug).

Embodiments of the present disclosure include conjugates where an antibody is conjugated to one or more drug moieties, such as 2 drug moieties, 3 drug moieties, 4 drug moieties, 5 drug moieties, 6 drug moieties, 7 drug moieties, 8 drug moieties, 9 drug moieties, or 10 or more drug moieties. The drug moieties may be conjugated to the antibody at one or more sites in the antibody, as described herein. In certain embodiments, the conjugates have an average drug-to-antibody ratio (DAR) (molar ratio) in the range of from 0.1 to 10, or from 0.5 to 10, or from 1 to 10, such as from 1 to 9, or from 1 to 8, or from 1 to 7, or from 1 to 6, or from 1 to 5, or from 1 to 4, or from 1 to 3, or from 1 to 2. In certain embodiments, the conjugates have an average DAR from 1 to 2, such as 1, 1.1, 1.2, 1.3, 1.4, 1.5, 1.6, 1.7, 1.8, 1.9 or 2. In certain embodiments, the conjugates have an average DAR of 1 to 1.5. In certain embodiments, the conjugates have an average DAR of 1.5 to 2. By average is meant the arithmetic mean.

Drugs to be conjugated to a polypeptide may be modified to incorporate a reactive partner for reaction with the polypeptide. Where the drug is a peptide drug, the reactive moiety (e.g., aminooxy or hydrazide can be positioned at an N-terminal region, the N-terminus, a C-terminal region, the C-terminus, or at a position internal to the peptide. For example, an example of a method involves synthesizing a peptide drug having an aminooxy group. In this example, the peptide is synthesized from a Boc-protected precursor. An amino group of a peptide can react with a compound comprising a carboxylic acid group and oxy-N-Boc group. As an example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-—N-methylmethanaminium hexafluorophosphate N-oxide), BOP—Cl (bis(2-oxo-3-oxazolidinyl)phosphinic chloride), PyBOP ((1-H-1,2,3-benzotriazol-1-yloxy)-tris(pyrrolidino)phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). As a non-limiting example, HOBt and DIC can be used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999, John Wiley & Sons, NY and Harrison et al. Certain deprotection conditions include a hydrazine reagent, amino reagent, or sodium borohydride. Deprotection of a Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the amino acid residue to reaction with a reactive partner of interest) are of importance, Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

Small molecule compounds containing, or modified to contain, an α-nucleophilic group that serves as a reactive partner with a compound or conjugate disclosed herein are also contemplated for use as drugs in the polypeptide-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Formulations

The conjugates of the present disclosure can be formulated in a variety of different ways. In general, where the conjugate is an antibody-drug conjugate, the conjugate is formulated in a manner compatible with the drug, the antibody, the condition to be treated, and the route of administration to be used.

In some embodiments, provided is a pharmaceutical composition that includes any of the conjugates of the present disclosure and a pharmaceutically-acceptable excipient.

The conjugate (e.g., antibody-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those readily available. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The antibody-drug conjugates of the present disclosure find use in treatment of a condition or disease in a subject that is amenable to treatment by administration of the parent drug (i.e., the drug prior to conjugation to the antibody).

In some embodiments, provided are methods that include administering to a subject an effective amount (e.g., a therapeutically effective amount) of any of the conjugates of the present disclosure.

In certain aspects, provided are methods of delivering a drug to a target site in a subject, the method including administering to the subject a pharmaceutical composition including any of the conjugates of the present disclosure, where the administering is effective to release a therapeutically effective amount of the drug from the conjugate at the target site in the subject. For example, as described herein, antibody-drug conjugates of the present disclosure can include a cleavable linker, such as an enzymatically cleavable linker that includes a sulfatase-cleavable moiety, which can be cleaved under appropriate conditions to separate or release the drug from the antibody at a desired target site of action for the drug. For example, a sulfatase enzyme may facilitate the hydrolysis of the sulfatase-cleavable moiety to cleave or separate the cleavable linker into two or more portions, thus releasing the drug from the antibody-drug conjugate at a desired site of action.

In some instances, the sulfatase enzyme that facilitates cleavage of the sulfatase-cleavable moiety is a sulfatase enzyme that is administered to the subject to be treated (i.e., exogenous to the subject to be treated). For example, the sulfatase enzyme can be administered before, concurrently with, or after administration of an antibody-drug conjugate described herein.

In other instances, the sulfatase enzyme that facilitates cleavage of the sulfatase-cleavable moiety is a sulfatase enzyme that is present in the subject to be treated (i.e., endogenous to the subject to be treated). For instance, the sulfates enzyme may be present at the desired site of action for the drug of the antibody-drug conjugate. The antibody of the antibody-drug conjugate may be specifically targeted to a desired site of action (e.g., may specifically bind to an antigen present at a desired site of action), where the desired site of action also includes the presence of a sulfatase enzyme. In some instances, the sulfatase enzyme is present in an overabundance at the desired site of action as compared to other areas in the body of the subject to be treated. For example, the sulfatase enzyme may be overexpressed at the desired site of action as compared to other areas in the body of the subject to be treated. In some instances, the sulfatase enzyme if present in an overabundance at the desired site of action due to localization of the sulfatase enzyme at a particular area or location. For instance, the sulfatase enzyme may be associated with a certain structure within the desired site of action, such as lysosomes. In some cases, the sulfatase enzyme is present in an overabundance in lysosomes as compared to other areas in the body of the subject. In some embodiments, the lysosomes that include sulfatase enzymes, are found at a desired site of action for the drug of the antibody-drug conjugate, such as the site of a cancer or tumor that is to be treated with the drug. In certain embodiments, the sulfatase enzyme is a human sulfatase enzyme. Examples of substrates and subcellular locations of human sulfatases are listed in Table 1 below.

TABLE 1

| Sulfatase | Physiological substrate | Subcellular location |
|---|---|---|
| Aryl sulfatase A (ARSA) | Sulfatide | Lysosome |
| Aryl sulfatase B (ARSB) | Dermatan sulfate, chondroitin sulfate | Lysosome |
| Aryl sulfatase C (ARSC) | Steroid sulfates | Endoplasmic reticulum (ER) |
| Aryl sulfatase D (ARSD) | Unknown | ER |
| Aryl sulfatase E (ARSE) | Unknown | Golgi network |
| Aryl sulfatase F (ARSF) | Unknown | ER |
| Aryl sulfatase G (ARSG) | Unknown | ER |
| Galactosamine-6-sulfatase (GalN6S) | Chondroitin sulfate, keratan sulfate | Lysosome |
| Glucosamine-3-sulfatase (GlcN3S) | Heparan sulfate | Lysosome |
| Glucosamine-6-sulfatase (GlcN6S) | Heparan sulfate, keratan sulfate | Lysosome |
| Glucouronate-2-sulfatase (GlcA2S) | Heparan sulfate | Lysosome |
| Heparin-N-sulfatase (GlcNS) | Heparan sulfate | Lysosome |
| Iduronate-2-sulfatase (IdoA2S) | Heparan sulfate, dermatan sulfate | Lysosome |

TABLE 1-continued

| Sulfatase | Physiological substrate | Subcellular location |
|---|---|---|
| Endo sulfatase 1 (Sulf1) | Heparan sulfate | Extra cellular matrix (ECM) |
| Endo sulfatase 2 (SULF2) | Heparan sulfate | ECM |

Any suitable sulfatase enzyme can be used for cleavage of the sulfatase-cleavable moiety of the antibody-drug conjugates described herein. Non-limiting examples of suitable sulfatase enzymes are listed in Table 1. Other sulfatases may also be suitable for use in cleavage of the sulfatase-cleavable moiety of the antibody-drug conjugates described herein, such as but not limited to, sulfatases from other vertebrates (e.g., primates, mice, rats, cats, pigs, quails, goats, dogs, etc.).

In certain embodiments, the sulfatase enzyme may facilitate the hydrolysis of the sulfatase-cleavable moiety to cleave or separate the cleavable linker into two or more portions as described above. An example of a mechanism of action for the cleavage of a sulfatase-cleavable moiety in a cleavable linker and release of a drug (e.g., auristatin, MMAE) is shown in the scheme below.

the desired site of action. In certain embodiments, after administration to a subject the antibody-drug conjugate is stable for an extended period of time in the absence of a sulfatase enzyme, such as 1 hr or more, or 2 hrs or more, or 3 hrs or more, or 4 hrs or more, or 5 hrs or more, or 6 hrs or more, or 7 hrs or more, or 8 hrs or more, or 9 hrs or more, or 10 hrs or more, or 15 hrs or more, or 20 hrs or more, or 24 hrs (1 day) or more, or 2 days or more, or 3 days or more, or 4 days or more, or 5 days or more, or 6 days or more, or 7 days (1 week) or more. In certain embodiments, the antibody-drug conjugate is stable at a range pH values for an extended period of time in the absence of a sulfatase enzyme, such as at a pH ranging from 2 to 10, or from 3 to 9, or from 4 to 8, or from 5 to 7, or from 6 to 7.

As described above, the antibody-drug conjugates of the present disclosure find use in treatment of a condition or

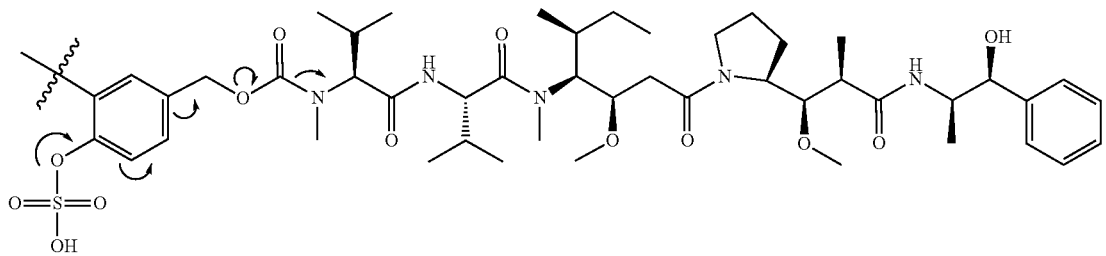 [SMILES: *c1cc(COC(=O)N(C)[C@H](C(=O)N[C@H](C(=O)N(C)[C@@H]([C@@H](C)CC)[C@@H](CC(=O)N2CCC[C@H]2[C@H](OC)[C@@H](C)C(=O)N[C@H](C)[C@@H](O)c2ccccc2)OC)C(C)C)C(C)C)ccc1OS(=O)(=O)O]

where ∿∿ indicates the point of attachment between the sulfatase-cleavable moiety and the first linker, $L^1$, e.g., as shown in formula (I) above. For example, as shown in the structure above, the ∿∿ symbol indicates the bond between the sulfate-containing group of the sulfatase-cleavable moiety and the first linker, $L^1$, e.g., as shown in formula (I) above.

In certain embodiments, the antibody-drug conjugate is substantially stable under standard conditions. By substantially stable is meant that the sulfatase-cleavable linker of the antibody-drug conjugate does not undergo a significant amount of cleavage in the absence of a sulfatase enzyme. For instance, the sulfatase-cleavable linker of the antibody-drug conjugate may be substantially stable such that 25% or less of the antibody-drug conjugate is cleaved in the absence of a sulfatase enzyme, such as 20% or less, or 15% or less, or 10% or less, or 5% or less, or 4% or less, or 3% or less, or 2% or less, or 1% or less. In some cases, the antibody-drug conjugate is substantially stable such that the sulfatase-cleavable linker of the antibody-drug conjugate does not undergo a significant amount of cleavage in the absence of a sulfatase enzyme, but can be cleaved when in the presence of a sulfatase enzyme. For example, the antibody-drug conjugate can be substantially stable after administration to a subject. In some cases, the antibody-drug conjugate is substantially stable after administration to a subject, and then, when the antibody-drug conjugate is in the presence of a sulfatase enzyme at a desired site of action, the sulfatase-cleavable moiety of the antibody-drug conjugate can be cleaved by the sulfatase enzyme, thus releasing the drug at disease in a subject that is amenable to treatment by administration of the parent drug. By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The subject to be treated can be one that is in need of therapy, where the subject to be treated is one amenable to treatment using the parent drug. Accordingly, a variety of subjects may be amenable to treatment using the antibody-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees and monkeys).

The amount of antibody-drug conjugate administered can be initially determined based on guidance of a dose and/or dosage regimen of the parent drug. In general, the antibody-drug conjugates can provide for targeted delivery and/or enhanced serum half-life of the bound drug, thus providing for at least one of reduced dose or reduced administrations in a dosage regimen. Thus, the antibody-drug conjugates can provide for reduced dose and/or reduced administration in a dosage regimen relative to the parent drug prior to being conjugated in an antibody-drug conjugate of the present disclosure.

Furthermore, as noted above, because the antibody-drug conjugates can provide for controlled stoichiometry of drug delivery, dosages of antibody-drug conjugates can be calculated based on the number of drug molecules provided on a per antibody-drug conjugate basis.

In some embodiments, multiple doses of an antibody-drug conjugate are administered. The frequency of administration of an antibody-drug conjugate can vary depending on any of a variety of factors, e.g., severity of the symptoms, condition of the subject, etc. For example, in some embodiments, an antibody-drug conjugate is administered once per month, twice per month, three times per month, every other week, once per week (qwk), twice per week, three times per week, four times per week, five times per week, six times per week, every other day, daily (qd/od), twice a day (bds/bid), or three times a day (tds/tid), etc.

Methods of Treating Cancer

The present disclosure provides methods that include delivering a conjugate of the present disclosure to an individual having a cancer. The methods are useful for treating a wide variety of cancers, including carcinomas, sarcomas, leukemias, and lymphomas. In the context of cancer, the term "treating" includes one or more (e.g., each) of: reducing growth of a solid tumor, inhibiting replication of cancer cells, reducing overall tumor burden, and ameliorating one or more symptoms associated with a cancer.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

In certain aspects, provided are methods of treating cancer in a subject, such methods including administering to the subject a therapeutically effective amount of a pharmaceutical composition including any of the conjugates of the present disclosure, where the administering is effective to treat cancer in the subject.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H. D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

Synthesis of Construct 13, an MMAE Payload Containing a Sulfatase Cleavable Linker Synthetic reagents were purchased from Sigma-Aldrich, Acros, and TCI and were used without purification. Anhydrous solvents were obtained from commercial sources in sealed bottles. 4-Hydroxymethyl-2-nitrophenol (1) and MMAE (8) were purchased from commercial sources. Compound 11 was purchased from Medicilon (Shanghai, China) and used without purification. All reactions were carried out in flame-dried glassware under $N_2$ unless otherwise noted. In all cases, solvent was removed by reduced pressure with a Buchi Rotovapor R-114 equipped with a Buchi V-700 vacuum pump. Column chromatography was performed with a Biotage Isolera Prime chromatograph. Purifications were performed using Waters preparative HPLC unit equipped with Phenomenex Kinetex 5 μm EVO C18 150× 21.2 mm column. HPLC analyses were conducted on an Agilent 1100 Series Analytical HPLC equipped with a Model G1322A Degasser, Model G1311A Quaternary Pump, Model G1329A Autosampler, Model G1314 Variable Wavelength Detector, Agilent Poroshell 120 SB C18, 4.6 mm×50 mm column at room temperature using a 10-100% gradient of water and acetonitrile containing 0.1% formic acid. HPLCs were monitored at 254 nm.

Scheme 1. Synthesis of intermediate 7.

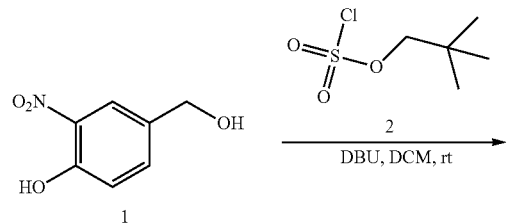

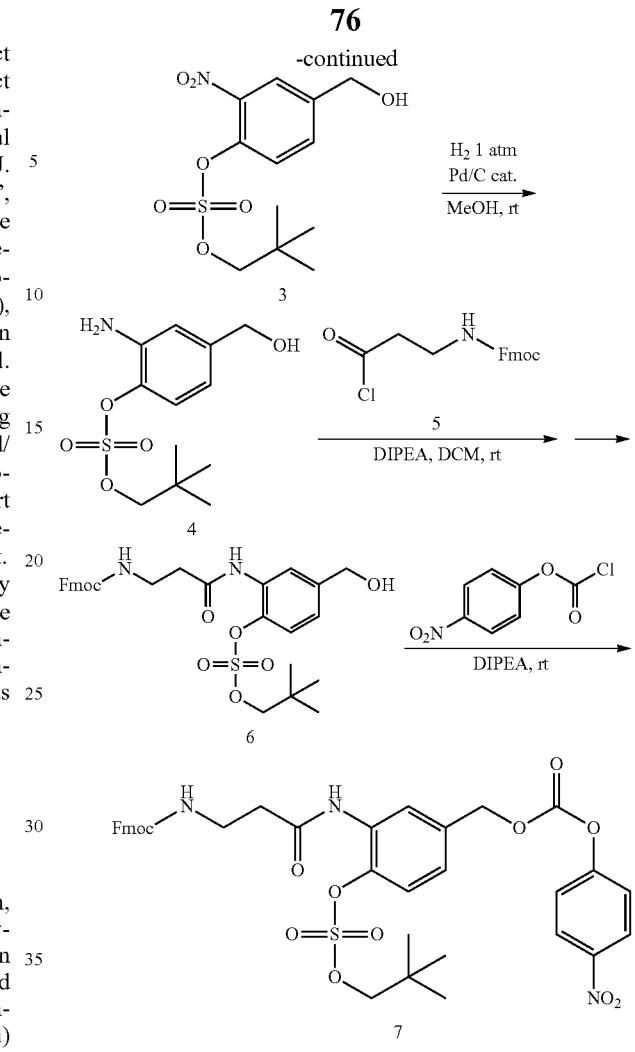

A sulfated analog of p-hydroxybenzyl alcohol was synthesized starting from 4-(hydroxymethyl)-2-nitrophenol 1 and neopentyl chlorosulfate 2 (Scheme 1). See, e.g., Simpson L S, Widlanski T S., *J. Am Chem Soc.* 2006; 128(5): 1605-1610. The nitro group was further elaborated to include β-alanine moiety for linker attachment. Next, the hydroxyl group was activated for coupling as p-nitrophenyl carbonate (compound 7, Scheme 1).

4-(Hydroxymethyl)-2-nitrophenyl neopentyl sulfate (3)

To an oven-dried 25 mL round-bottom flask were added 0.85 g (5 mmol) of 4-hydroxymethyl-2-nitrophenol (1), 8 mL of anhydrous THF, and 0.91 mL (6 mmol) of DBU. To this mixture, 1.18 g (6 mmol) of chlorosulfate $2^4$ was added slowly at ambient temperature with vigorous stirring. Reaction mixture was allowed to stir at room temperature for 4 hours until reaction was judged complete by LCMS analysis. Product was isolated by chromatography on silica gel eluting with 20% ethyl acetate-hexane mixture to obtain 0.76 g (2.4 mmol, 48% yield) of the title compound as yellow oil.

LRMS (ESI): m/z 337.1 $[M+H_2O]^+$, Calcd for $C_{12}H_{19}NO_8S$ m/z 337.1.

2-Amino-4-(hydroxymethyl)phenyl neopentyl sulfate (4)

Starting material (155 mg, 0.48 mmol) was combined with 102 mg (0.1 mmol) of palladium on carbon (10% wt) in 5 mL anhydrous methanol. Reaction flask was sealed and equipped with a hydrogen balloon, and the mixture was allowed to stir at ambient temperature for three days. Reaction mixture was filtered through a pad of Celite and evaporated to dryness. The resulting yellow oil was subjected to the next step without purification.

LRMS (ESI): m/z 290.1 [M+H]$^+$, Calcd for $C_{12}H_{20}NO_5S$ m/z 290.1.

2-(3-((((9H-fluoren-9-yl)methoxy)carbonyl)amino)propanamido)-4-(hydroxymethyl)phenyl neopentyl sulfate (6)

Crude 2-amino-4-(hydroxymethyl)phenyl neopentyl sulfate (4) (0.48 mmol) was dissolved in 3 mL of anhydrous dichloromethane and treated with DIPEA (0.21 mL, 1.2 mmol), followed by freshly prepared Fmoc-β-alanine chloride[6] (160 mg, 0.48 mmol) at room temperature. Reaction mixture was allowed to stir at room temperature for two hours until full consumption of starting material. Reaction mixture was purified on silica gel with 1:1 ethyl acetate-dichloromethane mixture as eluent to obtain 32 mg of compound 6 (0.055 mmol, 12% yield over two steps).

LRMS (ESI): m/z 583.2 [M+H]$^+$, Calcd for $C_{30}H_{35}N_2O_8S$ m/z 583.2.

2-(3-((((9H-fluoren-9-yl)methoxy)carbonyl)amino)propanamido)-4-((((4-nitrophenoxy)carbonyl)oxy)methyl)phenyl neopentyl sulfate (7)

Benzyl alcohol starting material (6) (18.7 mg, 32 μmol) was dissolved in 0.30 mL of anhydrous dichloromethane and treated with DIPEA (18.5 μL, 96 μmol), followed by 14.2 mg (64 μmol) of p-nitrophenyl chloroformate in one portion at room temperature. The resulting mixture was allowed to stir at room temperature for three hours until starting material was fully consumed as judged by LCMS analysis. Reaction mixture was diluted with 20 mL of dichloromethane, washed with 10% aqueous citric acid solution (3×5 mL), followed by wash with 5 mL of saturated sodium bicarbonate solution and 5 mL of brine. Organic layer was dried over magnesium sulfate, filtered, and evaporated to dryness to obtain crude PNP carbonate 7, which was submitted to the next step without purification.

LRMS (ESI): m/z 748.2 [M+H]$^+$, Calcd for $C_{37}H_{38}N_3O_{12}S$ m/z 748.2.

Scheme 2. Synthesis of sulfatase cleavable HIPS-MMAE construct 13.

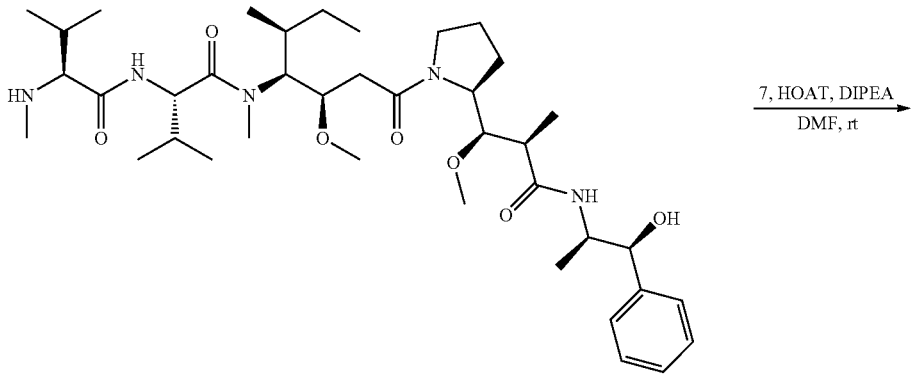

8

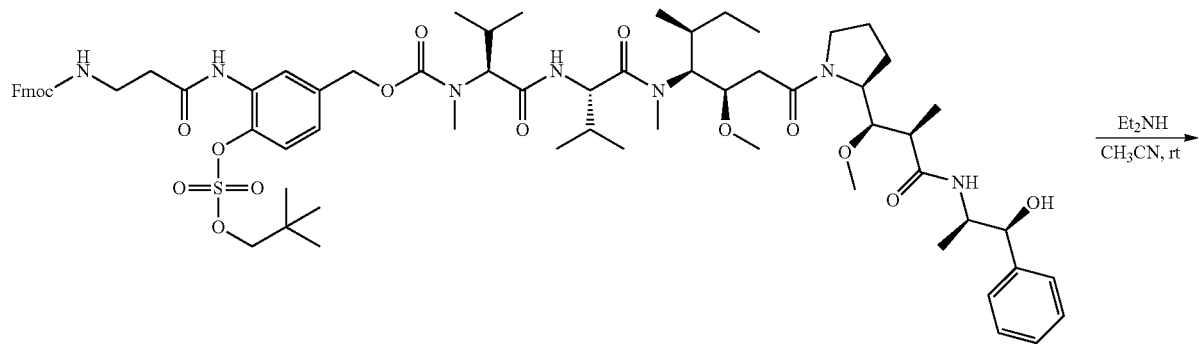

9

-continued
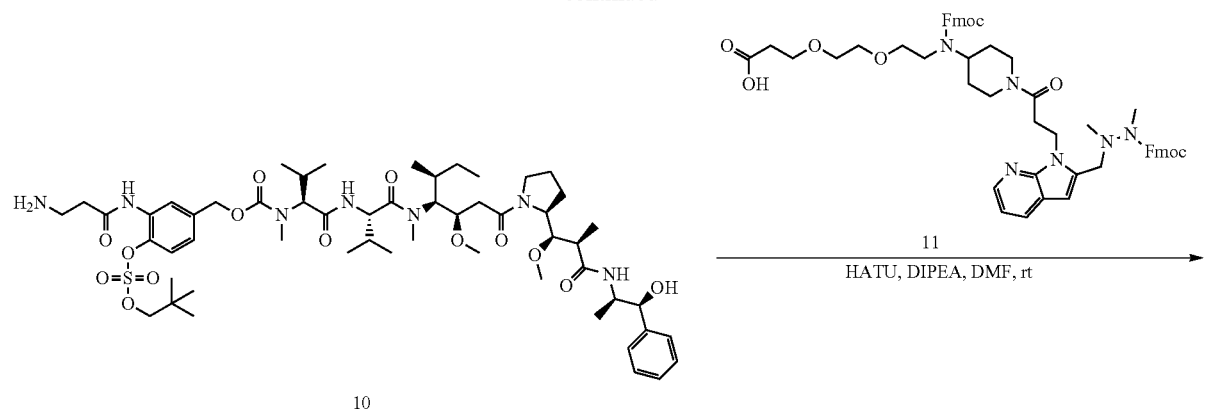
10
11
HATU, DIPEA, DMF, rt
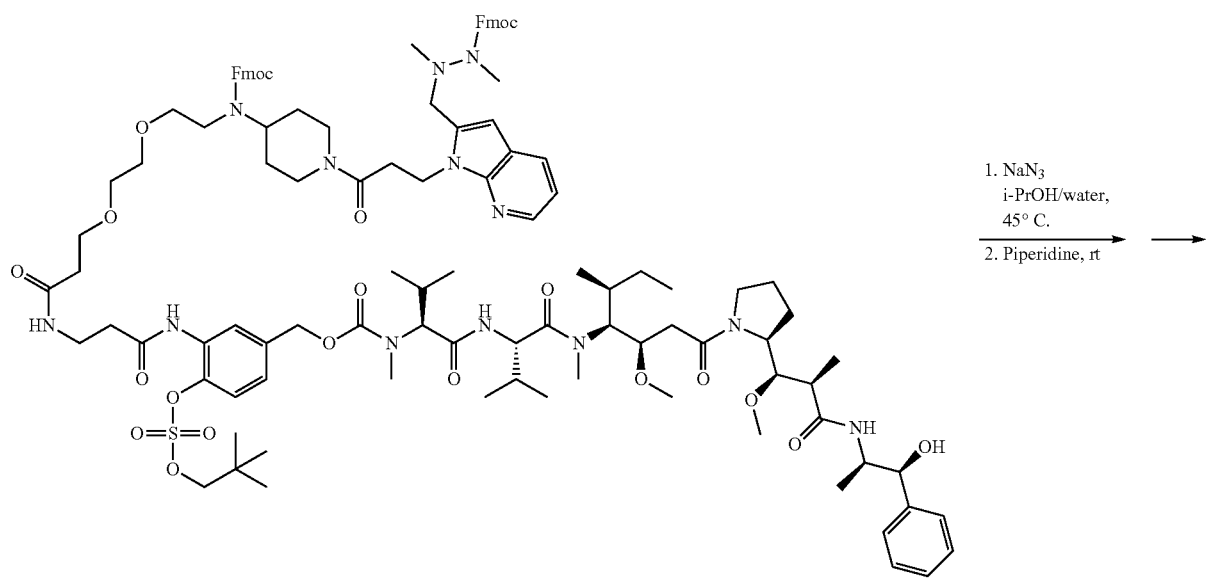
12
1. NaN₃
   i-PrOH/water,
   45° C.
2. Piperidine, rt

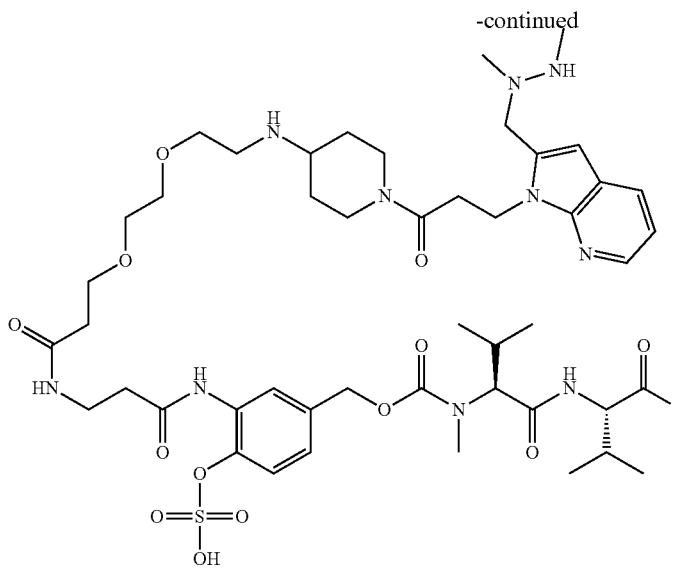
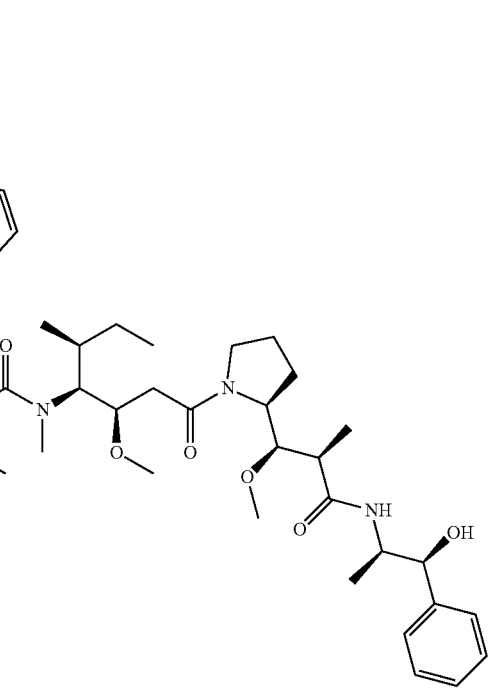

13

Compound 7 was coupled with MMAE payload, and further elaborated with separately synthesized linker 11, containing the HIPS conjugation moiety (Scheme 2). Global deprotection of compound 12 afforded free phenylsulfate-containing MMAE construct 13 with the HIPS moiety ready for conjugation.

2-(3-((((9H-fluoren-9-yl)methoxy)carbonyl)amino)
propanamido)-4-((5S,8S,11S,12R)-11-((S)-sec-
butyl)-12-(2-((S)-2-((1R,2R)-3-(((1S,2R)-1-hydroxy-
1-phenylpropan-2-yl)amino)-1-methoxy-2-methyl-3-
oxopropyl)pyrrolidin-1-yl)-2-oxoethyl)-5,8-
diisopropyl-4,10-dimethyl-3,6,9-trioxo-2,13-dioxa-4,
7,10-triazatetradecyl)phenyl neopentyl sulfate (9)

Crude PNP carbonate 7 (30 mol) was dissolved in DMF (0.50 mL), and combined with MMAE-TFA salt (30 mg). The resulting mixture was treated with 31 µL of DIPEA and 5 mg of HOAt, and stirred for two hours until reaction was complete judged by LCMS analysis. Product was isolated directly from the reaction mixture using reversed-phase chromatography (C18 Biotage cartridge), eluting with 0-100% acetonitrile-water with 0.1% formic acid additive to obtain 14.4 mg of product 9 (34% yield over two steps).

LRMS (ESI): m/z 1326.6 [M+H]$^+$, Calcd for $C_{70}H_{100}N_7O_{16}S$ m/z 1326.7.

2-(3-aminopropanamido)-4-((5S,8S,11S,12R)-11-
(S)-sec-butyl)-12-(2-((S)-2-((1R,2R)-3-(((1S,2R)-1-
hydroxy-1-phenylpropan-2-yl)amino)-1-methoxy-2-
methyl-3-oxopropyl)pyrrolidin-1-yl)-2-oxoethyl)-5,
8-diisopropyl-4,10-dimethyl-3,6,9-trioxo-2,13-
dioxa-4,7,10-triazatetradecyl)phenyl neopentyl
sulfate (10)

Fmoc-protected starting material (9, 14.4 mg, 11 µmol) was dissolved in 200 µL of anhydrous acetonitrile and treated with 20 µL of diethylamine at room temperature. The resulting mixture was allowed to stand for three hours until completion was confirmed by LCMS analysis. Solvents were removed under vacuum; the residue was azeotropically dried using acetonitrile (3×1 mL). Crude product was dried under high vacuum overnight and subjected to the subsequent step.

LRMS (ESI): m/z 1104.5 [M+H]$^+$, Calcd for $C_{55}H_{90}N_7O_{14}S$ m/z 1104.6.

(9H-fluoren-9-yl)methyl2-((1-(3-(4-((((9H-fluoren-
9-yl)methoxy)carbonyl)(2-(2-(3-((3-((5-((5S,8S,11S,
12R)-11-((S)-sec-butyl)-12-(2-((S)-2-((1R,2R)-3-
(((1S,2R)-1-hydroxy-1-phenylpropan-2-yl)amino)-1-
methoxy-2-methyl-3-oxopropyl)pyrrolidin-1-yl)-2-
oxoethyl)-5,8-diisopropyl-4,10-dimethyl-3,6,9-
trioxo-2,13-dioxa-4,7,10-triazatetradecyl)-2-
(((neopentyloxy)sulfonyl)oxy)phenyl)amino)-3-
oxopropyl)amino)-3-oxopropoxy)ethoxy)ethyl)
amino)piperidin-1-yl)-3-oxopropyl)-1H-pyrrolo[2,3-
b]pyridin-2-yl)methyl)-1,2-dimethylhydrazine-1-
carboxylate (12)

Crude free amine 10 (11 µmol) was combined with compound 11 (11.8 mg, 12 mol), DIPEA (6.5 µL, 37 mol), and HATU (4.7 mg, 12 mol) in anhydrous DMF (200 µL) at ambient temperature. Reaction mixture was allowed to stand for three hours until no more of amine 10 was detected by LCMS analysis. The coupling product was directly isolated using HPLC (C18 prep. column, 20-70% gradient of CH$_3$CN/water/0.05% TFA) to obtain 18.8 mg (9.2 µmol, 84% yield) of compound 12.

LRMS (ESI): m/z 1018.2 [M+H]$^{++}$, Calcd for $C_{110}H_{149}N_{13}O_{22}S$ m/z 1018.5.

4-(((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)-2-(3-(3-(2-(2-((1-(3-(2-((1,2-dimethylhydrazinyl)methyl)-1H-pyrrolo[2,3-b]pyridin-1-yl)propanoyl)piperidin-4-yl)amino)ethoxy)ethoxy)propanamido)propanamido)phenyl hydrogen sulfate (13)

Starting material 12 (18.8 mg, 9.2 μmol) was dissolved in 1.2 mL of isopropanol and combined with 9.0 mg (0.14 mmol) of sodium azide in 0.5 mL of water. The resulting mixture was heated to 45° C. for 24 hours, cooled to room temperature and treated with 100 μL of piperidine. After 6 hours, product was directly isolated on C18 Biotage cartridge, eluting with 0-100% acetonitrile/water gradient. Lyophilized pure fractions afforded 7.5 mg (4.9 μmol, 54% yield) of the title compound 13.

LRMS (ESI): m/z 1520.7 [M+H]$^+$, Calcd for $C_{75}H_{118}N_{13}O_{18}S$ m/z 1520.8.

Example 2

Synthesis of Construct 29, an MMAE Payload Containing a Sulfatase Cleavable Linker Aryl sulfate linker with meta-orientation of amino-group and sulfate moiety was accessed starting from 4-(hydroxymethyl)-3-nitrophenyl (19) using synthetic route shown in Scheme 3. After installation of the neopentyl-protected sulfate as previously described in Simpson L S, Widlanski T S, *J. Am Chem Soc.*, 2006, 128(5):1605-1610, the remaining benzylic hydroxy group was THP-protected to give compound 21. Reduction of nitro group, followed by acylation with Fmoc-β-Ala chloride 5 and removal of the THP-protection gave benzyl alcohol 24, which was further activated by forming PNP carbonate 25.

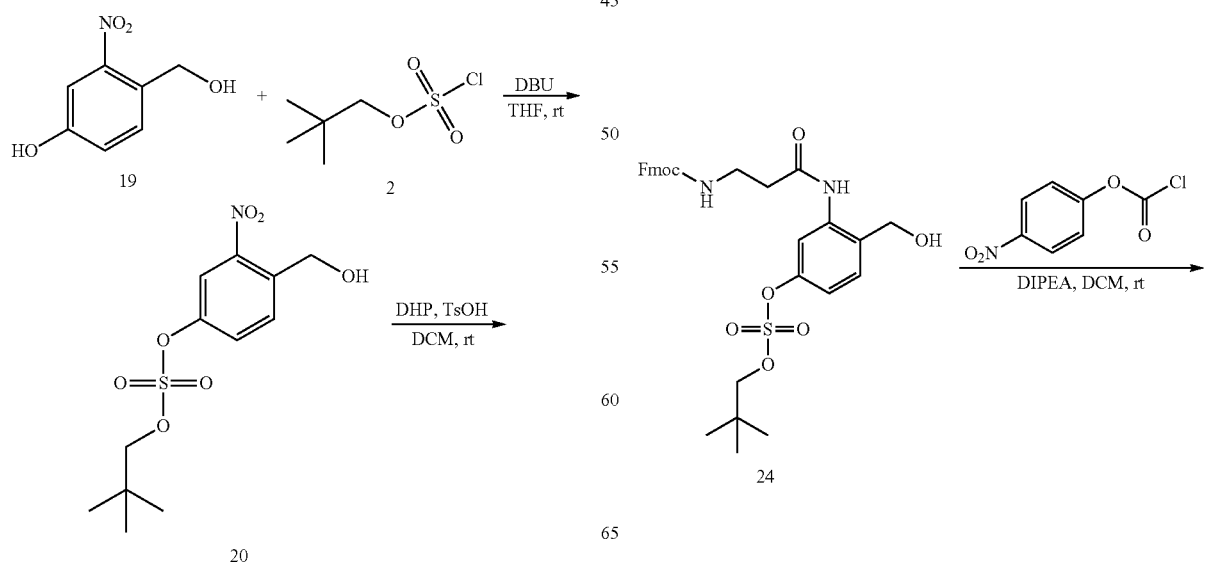

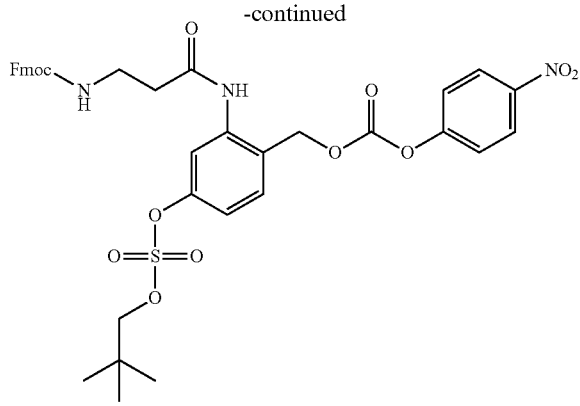

4-(Hydroxymethyl)-3-nitrophenyl neopentyl sulfate (20)

To a mixture of 4-(hydroxymethyl)-3-nitrophenol 19 (340 mg, 2 mmol) and 0.60 mL (2 mmol) of DBU in 10 mL of anhydrous THF, were added neat freshly prepared neopentyl chlorosulfate (0.64 mL, 2.2 mmol) in one portion at room temperature. The resulting dark-colored biphasic mixture was vigorously stirred at room temperature for two hours, until reaction was judged compete by HPLC analysis. Reaction mixture was quenched by adding 25 mL of saturated ammonium chloride solution, extracted with ethyl acetate (2×25 mL). Organic layer was washed with saturated sodium bicarbonate solution and brine, dried over sodium sulfate, and purified on silica gel, eluting with 0-25% ethyl acetate-hexanes gradient to afford 370 mg of sulfated product 20 (1.16 mmol, 58% yield) as yellow oil which solidified under high vacuum.

LRMS (ESI): m/z 336.9 [M+H$_2$O]$^+$, Calcd for C$_{12}$H$_{17}$NO$_7$S m/z 337.1.

Neopentyl (3-nitro-4-(((tetrahydro-2H-pyran-2-yl)oxy)methyl)phenyl) sulfate (21)

Benzyl alcohol derivative 20 (370 mg, 1.16 mmol) was dissolved in 5 mL of anhydrous dichloromethane, combined with dihydropyran (127 μL, 1.4 mmol) and p-toluenesulfonic acid monohydrate (11 mg, 0.06 mmol) at room temperature. The resulting mixture was stirred for 16 hours until reaction was rendered complete by TLC analysis. Reaction mixture was directly purified on silica gel, eluting with 0-25% ethyl acetate-hexane gradient to give 367 mg (0.91 mmol, 78% yield) of product 21 as colorless oil.

LRMS (ESI): m/z 425.8 [M+Na]$^+$, Calcd for C$_{17}$H$_{25}$NO$_8$S m/z 426.1.

3-Amino-4-(((tetrahydro-2H-pyran-2-yl)oxy)methyl)phenyl neopentyl sulfate (22)

Nitro compound 21 (375 mg, 0.93 mmol) was dissolved in a mixture of THF (2 mL) and methanol (1 mL). The resulting mixture was combined with a solution of ammonium chloride (400 mg, 7.4 mmol) in 3 mL of water, vigorously stirred, and treated with zinc powder (485 mg, 7.4 mmol) in small portions over five minutes period. The resulting suspension was stirred at room temperature for two hours, until reaction was rendered complete by HPLC analysis. Solids were filtered off; most solvents were removed from the filtrate under vacuum. Aqueous residue was diluted with saturated ammonium chloride (50 mL) and extracted with ethyl acetate (2×50 mL). Organic layer was washed with brine, dried over sodium sulfate, and purified on silica gel, eluting with 0-25% ethyl acetate-hexanes gradient to afford 303 mg (0.81 mmol, 87% yield) of the title compound 22 as slightly yellow oil, which slowly solidified into tan solid.

LRMS (ESI): m/z 373.9 [M+H]$^+$, Calcd for C$_{17}$H$_{27}$NO$_6$S m/z 374.2.

3-(3-((((9H-Fluoren-9-yl)methoxy)carbonyl)amino)propanamido)-4-(((tetrahydro-2H-pyran-2-yl)oxy)methyl)phenyl neopentyl sulfate (23)

To a mixture of aniline derivative 22 (303 mg, 0.81 mmol) and DIPEA (0.28 mL, 1.62 mmol) in 2 mL of anhydrous dichloromethane, freshly prepared Fmoc-β-alanine chloride (295 mg, 0.89 mmol) was added as a solid in one portion at room temperature. Reaction mixture was stirred for one hour until starting material was fully consumed as judged by HPLC and TLC analysis. Reaction mixture was directly applied to a silica gel column, and eluted with 50% ethyl acetate-hexane mixture to give 430 mg (0.65 mmol, 80% yield) of product 23 as white solid foam.

LRMS (ESI): m/z 688.8 [M+Na]$^+$, Calcd for C$_{35}$H$_{42}$N$_2$O$_9$S m/z 689.3.

3-(3-((((9H-Fluoren-9-yl)methoxy)carbonyl)amino)propanamido)-4-(hydroxymethyl)phenyl neopentyl sulfate (24)

A solution of THP-Protected compound 23 (430 mg, 0.65 mmol) in 2 mL of methanol was treated with 25 mg (0.013 mmol) of p-toluenesulfonic acid monohydrate. Reaction mixture was stirred at room temperature for one hour until deprotection was judged complete by HPLC analysis. Methanol was removed under vacuum, the residue was taken into 60 mL of ethyl acetate, washed with saturated sodium bicarbonate solution (30 mL) and brine, dried over sodium sulfate. After removal of solvents, the residue was purified on silica gel eluting with 50-70% ethyl acetate-hexanes gradient to give 290 mg (0.50 mmol, 77% yield) of title compound 24 as white solid.

LRMS (ESI): m/z 582.8 [M+H]$^+$, Calcd for C$_{30}$H$_{34}$N$_2$O$_8$S m/z 583.2.

3-(3-((((9H-Fluoren-9-yl)methoxy)carbonyl)amino)propanamido)-4-((((4-nitrophenoxy)carbonyl)oxy)methyl)phenyl neopentyl sulfate (25)

Benzylic alcohol 24 (290 mg, 0.5 mmol) was combined with DIPEA (0.26 mL, 1.5 mmol) in 2 mL of anhydrous DCM. To this mixture, p-nitrophenyl chloroformate (300 mg, 1.5 mmol) was added as a solid in one portion at ambient temperature. In one hour, reaction mixture was quenched by adding 50 mL of 10% aqueous citric acid solution, extracted with DCM (2×50 mL). Combined organic layer was dried over sodium sulfate and purified on silica gel eluting with 0-50% ethyl acetate-hexanes gradient to give 288 mg of product 25 (0.38 mmol, 77% yield) as white foamy solid.

LRMS (ESI): m/z 747.7 [M+H]$^+$, Calcd for C$_{37}$H$_{37}$N$_3$O$_{12}$S m/z 748.2.

Next, compound 25 was allowed to couple with the secondary amine of MMAE molecule, followed by a stepwise removal of protecting groups to give construct 27, which was further elaborated by a coupling with HIPS linker 11 (Scheme 4). The resulting compound 28 was deprotected to afford construct 29.

Scheme 4. Synthesis of Construct 29.

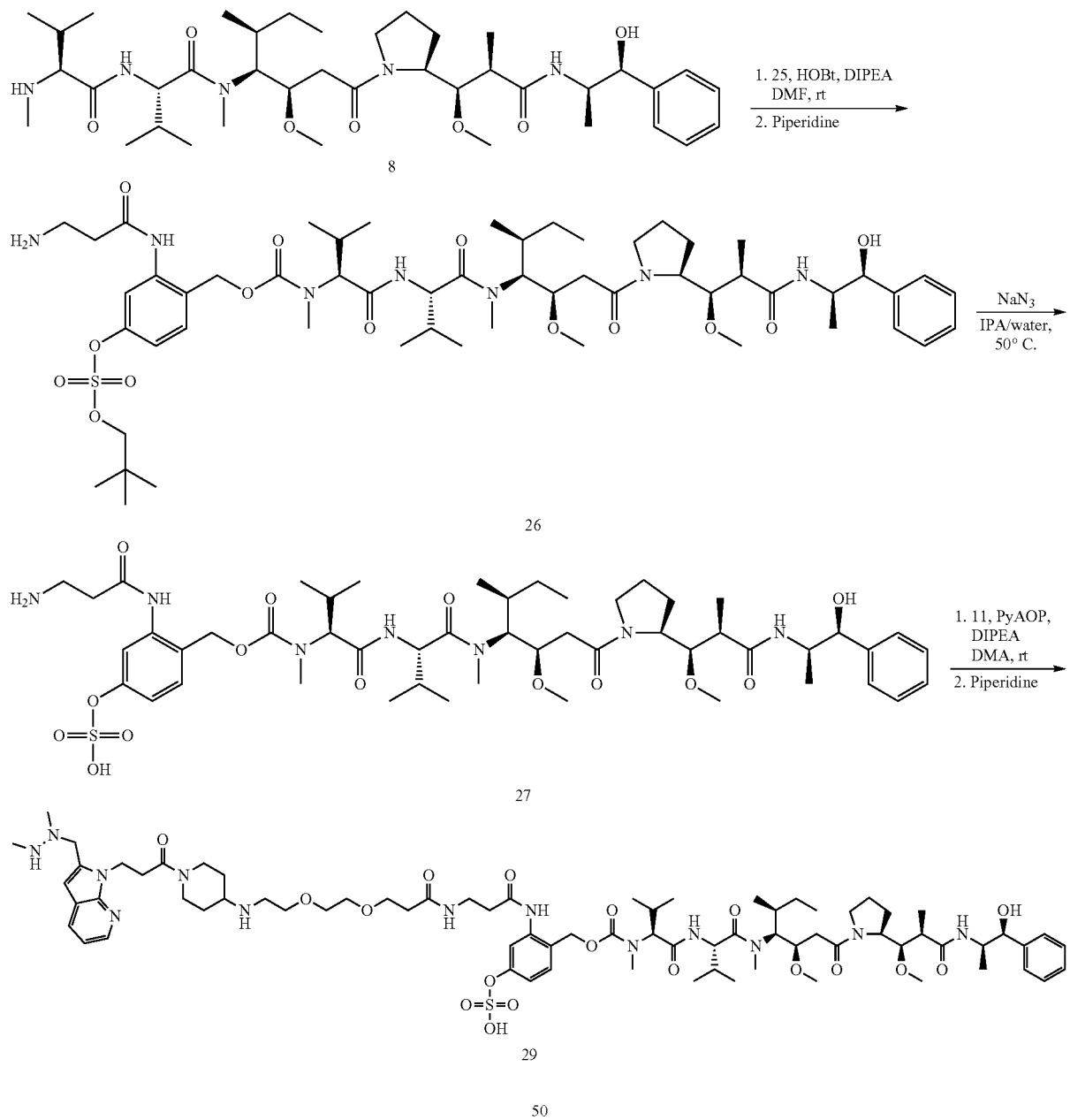

3-(3-Aminopropanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl neopentyl sulfate (26)

p-Nitrophenyl carbonate 25 (50 mg, 67 μmol) was added to a mixture of MMAE (47 mg, 67 μmol) and DIPEA (35 μL, 0.20 mmol) in 2 mL of anhydrous DMF, followed by addition of HOBt (9 mg, 67 μmol). Reaction mixture was allowed to stand at ambient temperature for two hours, until starting material was completely consumed as judged by HPLC analysis. Piperidine (35 μL) was added directly to the reaction mixture. After 30 minutes, reaction mixture was purified on reversed-phase column (C18), eluting with 0-100% gradient of acetonitrile-water/0.05% TFA. Pure fractions were lyophilized to give 41.5 mg (38 μmol, 58% yield) of compound 26 as colorless powder.

LRMS (ESI): m/z 1103.9 [M+H]$^+$, Calcd for $C_{55}H_{89}N_7O_{14}S$ m/z 1104.6.

3-(3-Aminopropanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl hydrogen sulfate (27)

Compound 26 (41 mg, 37 μmol) was combined with 37 mg of sodium azide (0.56 mmol) in a mixture of 2 mL of isopropanol and 1 mL of water. The resulting mixture was heated to 50° C. for 24 hours in a sealed vial until no more starting material was detected by HPLC analysis. Reaction mixture was directly purified on reversed-phase (C18) column, eluted with 0-100% $CH_3CN$—$H_2O$/0.05% TFA. Pure fractions were lyophilized to afford 7.5 mg (7.3 µmol, 19% yield) of compound 27 as white powder.

LRMS (ESI): m/z 1031.9 $[M-H]^+$, Calcd for $C_{50}H_{79}N_7O_{14}S$ m/z 1032.5.

4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)-3-(3-(3-(2-(2-((1-(3-(2-((1,2-dimethylhydrazinyl)methyl)-1H-pyrrolo[2,3-b]pyridin-1-yl)propanoyl)piperidin-4-yl)amino)ethoxy)ethoxy)propanamido)propanamido)phenyl hydrogen sulfate (29)

Amine starting material 27 (7.5 mg, 7.2 µmol) was dissolved in 1 mL of anhydrous DMA and combined with compound 11 (6.9 mg, 7.2 mol). The resulting mixture was treated with DIPEA (3.8 µL, 21.5 µmol) and PyAOP (3.8 mg, 7.2 µmol), let stand at RT for 20 minutes. Piperidine (14 µL, 0.15 mmol) was added directly to the reaction mixture. After 15 minutes, product was purified using HPLC (C18 column, 0-50% $CH_3CN$-water/0.05% TFA gradient). Pure fractions were lyophilized to give 7.5 mg (4.9 µmol, 68% yield) of the title compound 29 as white powder.

LRMS (ESI): m/z 1520.8 $[M+H]^+$, Calcd for $C_{75}H_{117}N_{13}O_{18}S$ m/z 1520.8.

Example 3

Bioconjugation

The conjugation reactions of Constructs 13 and 29 with antibodies containing an aldehyde tag at the C-terminus were carried out according to the procedure shown in Scheme 5. See Drake P M, Carlson A, McFarland J M, et al., *Mol Cancer Ther.* 2017:1-9. The drug-antibody ratios (DARs) were 1.8 and 1.6 for anti-CD79b and anti-HER ADCs respectively. These two ADCs were used for the following studies without further enrichment.

General Bioconjugation Conditions

The aldehyde-tagged antibody was conjugated to MMAE Construct 13 at 15 mg/mL and 8 drug:antibody equivalents for 72 h at 37° C. in 50 mM sodium citrate, pH 5.5, 50 mM NaCl in the presence of 0.85% DMA. Free drug was removed using tangential flow filtration (TFF) and exchanging into 20 mM NaCitrate, pH 5.5, 50 mM NaCl. To determine the DAR of the final product, ADCs were examined by hydrophobic interaction chromatography (Tosoh #14947 TSK gel Butyl-NPR 4.6 mm×35 mm; mobile phase A: 25 mM $NaPO_4$, 1.5 M $(NH_4)_2SO_4$, pH 7.0 and mobile phase B: 18.75 mM NaPO4, pH 7.0, 25% isopropanol). To monitor aggregation, samples were analyzed using size exclusion chromatography (SEC; Tosoh #08541) with a mobile phase of 300 mM NaCl, 25 mM sodium phosphate, pH 6.8, 5% isopropanol. Final products contained less than 5% aggregate.

Figure 4:
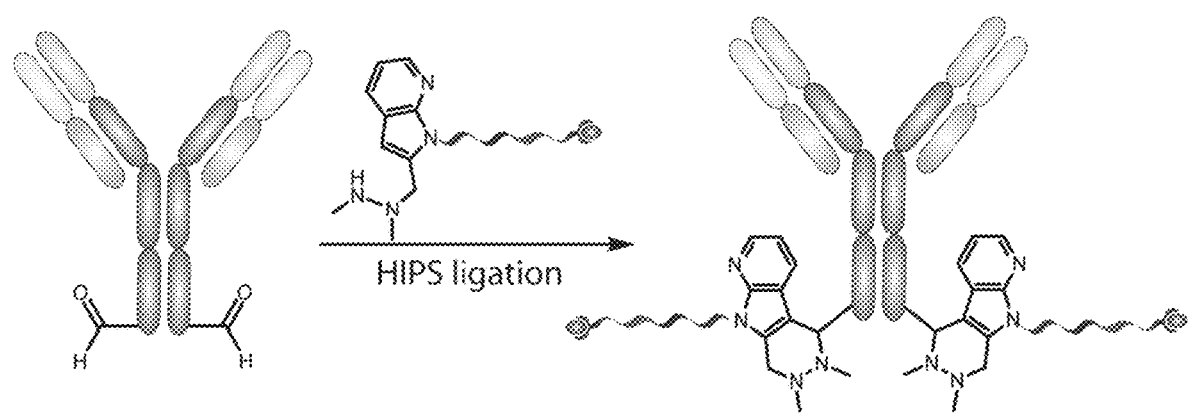
FIG. 4 shows a scheme of the HIPS ligation for the synthesis of ADCs, according to embodiments of the presently claimed invention.

Scheme 5. HIPS ligation for the synthesis of ADCs. Antibodies carrying aldehyde moieties were reacted with a Hydrazino-iso-Pictet-Spengler (HIPS) linker and payload to generate a site-specifically conjugated ADC with a stable azacarboline linkage (see FIG. 4).

Example 4

Serum Stability Assay

ADCs were spiked into rat serum at 40 µg/mL. The samples were aliquoted and stored at −80° C. until use. Aliquots were placed at 37° C. under 5% $CO_2$ for the indicated times, and then were analyzed by ELISA to assess the anti-MMAE (total ADC) and anti-Fab (total antibody) signals. A freshly thawed aliquot was used as a reference starting value for conjugation. All analytes were measured together on one plate to enable comparisons across time points. Analytes diluted 1:1000 in casein blocking buffer were captured on plates coated with an anti-human Fab-specific antibody. Then, the payload was detected with an anti-MMAE antibody followed by an HRP-conjugated goat anti-mouse Fcγ-specific antibody; the total antibody was detected with an HRP-conjugated goat anti-human Fcγ-specific antibody. Bound HRP-conjugated antibodies were visualized with TMB substrate. The colorimetric reaction was stopped with $H_2SO_4$, and the absorbance at 450 nm was determined using a Molecular Devices SpectraMax M5 plate reader. Data analysis was performed in Excel. Each sample was analyzed in quadruplicate, and the average values were used. The ratio of anti-MMAE signal to anti-Fab signal was used as a measure of antibody conjugation.

The stabilities of ADCs containing Construct 13 at the C-terminus in rat serum were examined using an ELISA-based assay to measure MMAE levels. The results indicated that both anti-HER2 and anti-CD22 MMAE ADCs were very stable (FIG. 1). There was no change in the ratio of anti-MMAE signal (total conjugate) to anti-Fab signal (total antibody) after incubation in rat serum at 37° C. for 7 d. FIG. 1 shows a graph of the serum stability over time of antibody-drug conjugates (ADCs) containing a sulfatase-cleavable linker.

Example 5

In Vitro Cytotoxicity

NCI—N87 and JeKo-1 cell lines are maintained in RPMI-1640 medium (Invitrogen) supplemented with 10% fetal bovine serum (Seradigm) and Glutamax (Invitrogen) in a 37° C. incubator with 5% $CO_2$. Cells are passaged regularly to ensure log-phase growth. On the day of plating, 5000 cells are added per well into 96-well plates in 100 µL normal growth medium and returned to the incubator for 24 h to equilibrate to plating conditions. Cells are then treated with 20 µL of serially diluted ADCs at 6× final desired concentration. After 5 d of incubation, cell viability is measured using CellTiter-Glo reagent (Promega) following manufacturer's recommendation. Luminescence is read on Spectra-Max M5 plate reader. GraphPad Prism software is used for data analysis, including calculation of an $IC_{50}$ from luminescence values normalized to controls present on each plate.

Figure 2A:
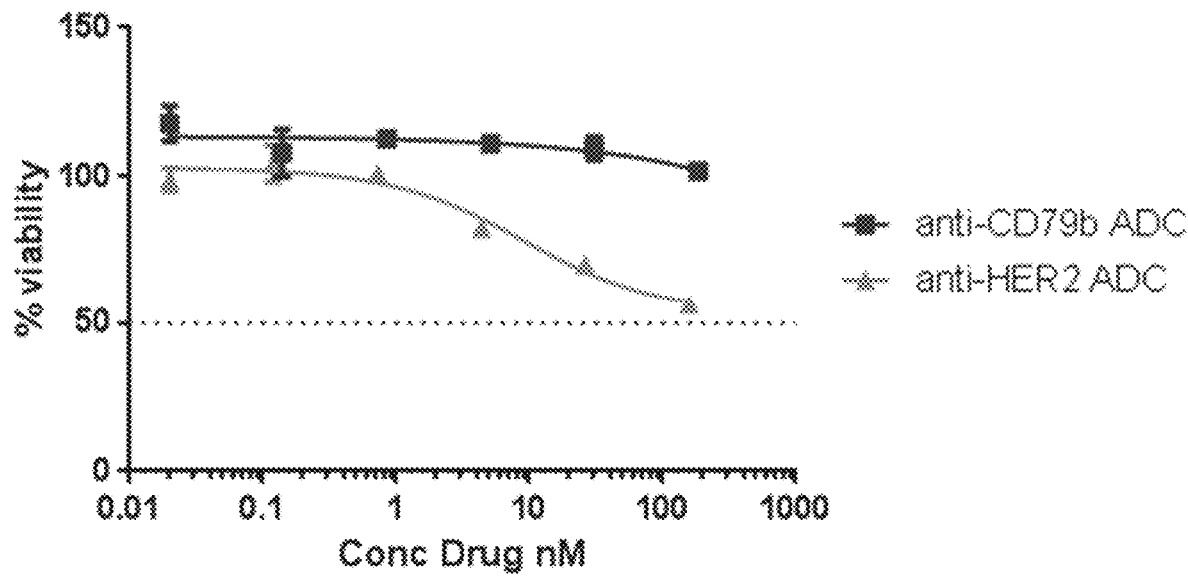
FIG. 2A shows a graph of % viability vs. drug concentration (nM) for an in vitro cytotoxicity assay of antibody-drug conjugates, according to embodiments of the present disclosure.

The in vitro cytotoxicity of anti-HER2 modified by the MMAE construct 13 at the C-terminus was assessed using the HER2-positive cell line, NCI—N87. As shown in FIG. 2A, the ADC exhibited potent dose-dependent toxicity with an $IC_{50}$ value of 9.3 nM. In contrast, the isotype ADC (anti-CD79b) showed minimal activity at concentrations up to 200 nM. FIG. 2A shows a graph of in vitro efficacy of ADCs containing a sulfatase cleavable linker against NCI—N87 cell line.

Figure 2B:
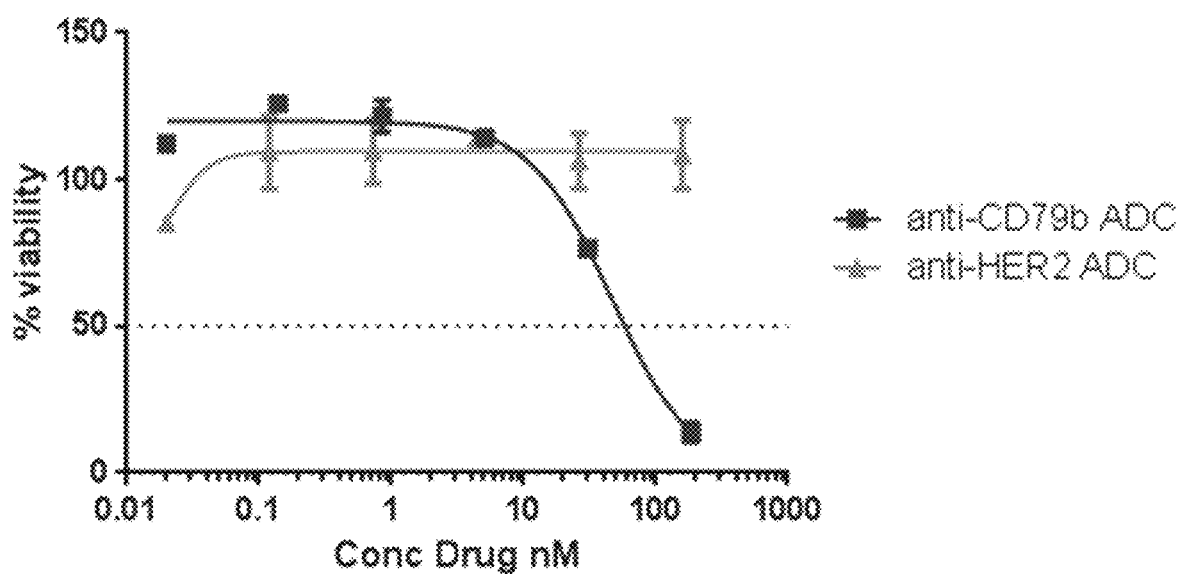
FIG. 2B shows a graph of % viability vs. drug concentration (nM) for an in vitro cytotoxicity assay of antibody-drug conjugates, according to embodiments of the present disclosure.

In another study, the in vitro cytotoxicity of anti-CD79b modified by the MMAE construct 13 at the C-terminus was assessed using the CD79b-positive cell line, JeKo-1. As shown in FIG. 2B, the conjugate exhibited dose-dependent toxicity with an $IC_{50}$ value of 47 nM. In contrast, an isotype ADC (anti-HER2) showed minimal activity at concentrations up to 200 nM. FIG. 2B shows a graph of in vitro efficacy of ADCs containing a sulfatase cleavable linker against JeKo-1 cell line.

Figure 2C:
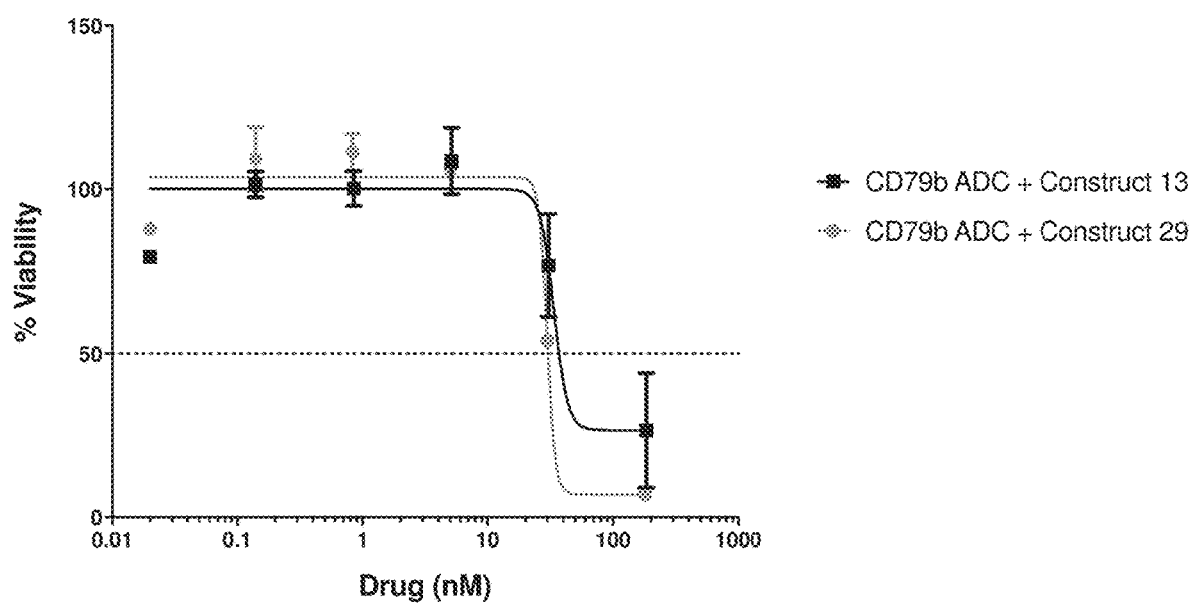
FIG. 2C shown a graph of % viability vs. drug concentration (nM) for an in vitro cytotoxicity assay of antibody-drug conjugates, according to embodiments of the present disclosure.

In a separate study, the in vitro cytotoxicity of ADCs synthesized from anti-CD79b and both Constructs 13 and 29 attached to C-terminus was assessed using CD79-expressing Jeko-1 cell line. As shown in FIG. 2C, the conjugates exhibited dose-dependent toxicity with $IC_{50}$ values of 30-34 nM. In contrast, an isotype C-terminus ADCs showed minimal activity at up to 200 nM concentration. FIG. 2C shows a graph of in vitro efficacy of ADCs containing sulfatase cleavable linker against Jeko-1 cell line.

Example 6

In Vivo Efficacy Study

All animal studies were conducted in accordance with Institutional Animal Care and Use Committee guidelines and were performed at Sundia (Shanghai, China). The murine anti-MMAE antibody was made by ProMab and validated in-house. The rabbit anti-AF488 antibody was purchased from Life Technologies. The horseradish peroxidase (HRP)-conjugated secondary antibodies were from Jackson ImmunoResearch (West Grove, PA). Cell lines were obtained from ATCC and DSMZ cell banks where they were authenticated by morphology, karyotyping, and PCR-based approaches.

Male CB17 SCID mice were inoculated subcutaneously with $1.0 \times 10^6$ JeKo-1 cells in 50% Matrigel. Dosing was initiated when the tumors reached an average of 167 $mm^3$. Animals (5 mice/group) were given an intravenous single dose (3 mg/kg ADC or vehicle alone). The animals were monitored twice weekly for body weight and tumor size. Tumor volume was calculated using the formula:

$$\text{Tumor volume (mm}^3) = \frac{w^2 \times l}{2}$$

Figure 3:
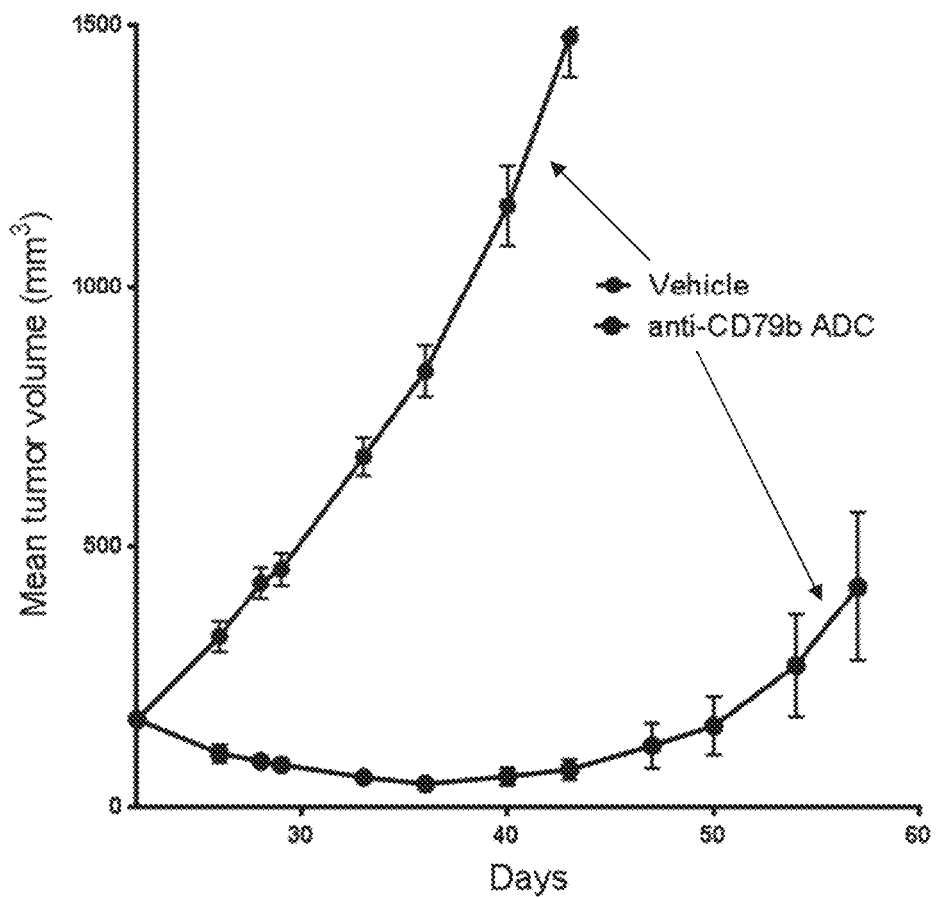
FIG. 3 shows a graph of mean tumor volume (mm$^3$) vs. time (days) for an in vivo efficacy study of an antibody-drug conjugate with a sulfatase-cleavable linker, according to embodiments of the presently claimed invention.

To test the in vivo efficacy of an anti-CD79b conjugated to MMAE construct 13 at the C-terminus, a JeKo-1 xenograft study was performed. Male CB17 SCID mice bearing a mantle cell lymphoma cell line Jeko-1 were treated with a single dose of 3 mg/kg of the anti-CD79b ADC or vehicle as a negative control. No severe toxicities were observed. A single dose of the ADC was sufficient to significantly stop tumor growth for about 36 days in treated animals (FIG. 3). FIG. 3 shows a graph of the in vivo efficacy of an anti-CD79b MMAE ADC with a sulfatase-cleavable linker against JeKo-1 xenografts in mice.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A conjugate of formula (I):

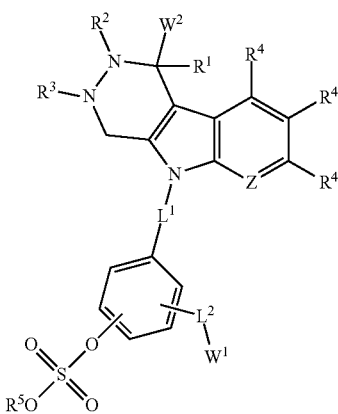

(I)

wherein

Z is $CR^4$ or N;

$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

each $R^4$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

$R^5$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$L^1$ is a first linker;

$L^2$ is a second linker;

$W^1$ is a drug; and $W^2$ is an antibody.

2. The conjugate of claim 1, wherein the conjugate is of formula (Ia):

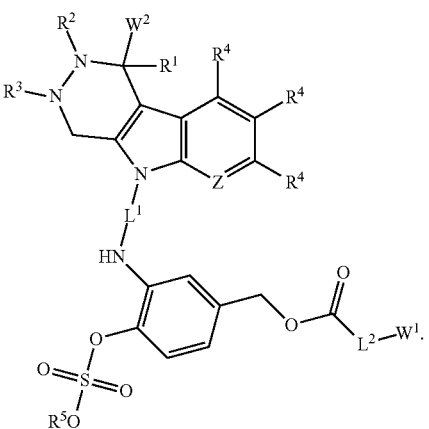

(Ia)

3. The conjugate of claim 1, wherein the conjugate is of formula (Ib):

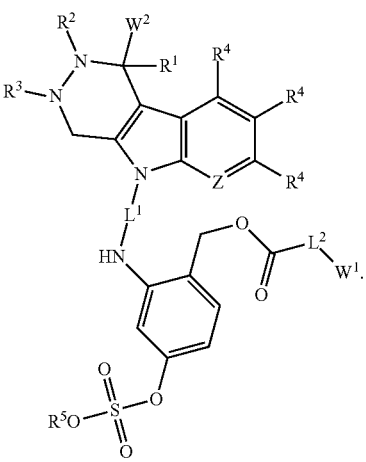

(Ib)

4. The conjugate of claim 1, wherein the conjugate is of formula (Ic):

(Ic)

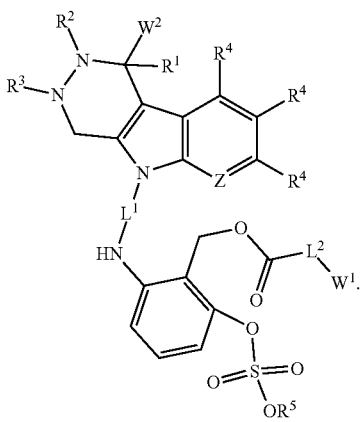

5. The conjugate of claim 1, wherein the conjugate is of formula (Id):

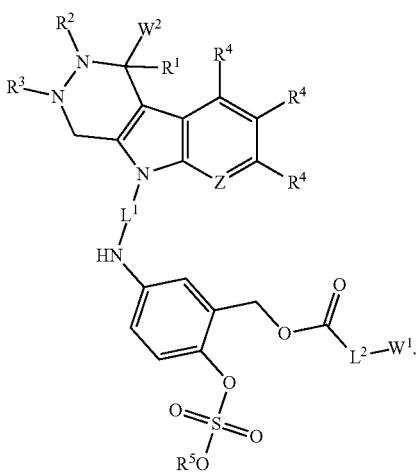

(Id)

6. The conjugate of claim 1, wherein the conjugate is of formula (Ie):

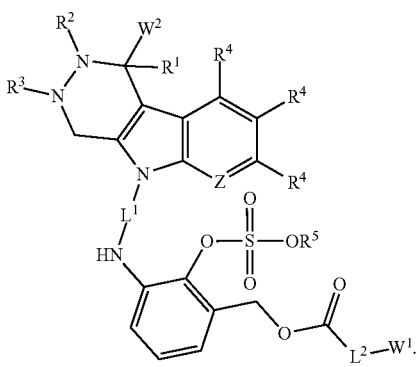

(Ie)

7. The conjugate of claim 1, wherein $L^1$ comprises:

$$-(T^1\text{-}V^1)_a\text{-}(T^2\text{-}V^2)_b\text{-}(T^3\text{-}V^3)_c\text{-}(T^4\text{-}V^4)_d\text{-},$$

wherein a, b, c and d are each independently 0 or 1;

$T^1$, $T^2$, $T^3$ and $T^4$ are each independently selected from ($C_1$-$C_{12}$)alkyl, substituted ($C_1$-$C_{12}$)alkyl, (EDA)w, (PEG)n, (AA)p, —(CR$^{13}$OH)$_m$—, piperidin-4-amino (4AP), an acetal group, a hydrazine, a disulfide, and an ester, wherein EDA is an ethylene diamine moiety, PEG is a polyethylene glycol, and AA is an amino acid residue, wherein each w is an integer from 1 to 20, each n is an integer from 1 to 30, each p is an integer from 1 to 20, and each m is an integer from 1 to 12;

$V^1$, $V^2$, $V^3$ and $V^4$ are each independently selected from the group consisting of a covalent bond, —CO—, —NR$^{15}$—, —NR$^{15}$(CH$_2$)$_q$—, —NR$^{15}$ (C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein each q is an integer from 1 to 6;

each $R^{13}$ is independently selected from hydrogen, an alkyl, a substituted alkyl, an aryl, and a substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

8. The conjugate of claim 1, wherein $L^2$ comprises:

$$-(T^5\text{-}V^5)_e\text{-}(T^6\text{-}V^6)_f\text{-}(T^7\text{-}V^7)_g\text{-}(T^8\text{-}V^8)_h\text{-},$$

wherein e, f, g and h are each independently 0 or 1;

$T^5$, $T^6$, $T^7$ and $T^8$ are each independently selected from ($C_1$-$C_{12}$)alkyl, substituted ($C_1$-$C_{12}$)alkyl, (EDA)$_w$, (PEG)$_n$, (AA)$_p$, —(CR$^{13}$OH)$_m$—, piperidin-4-amino (4AP), an acetal group, a hydrazine, a disulfide, and an ester, wherein EDA is an ethylene diamine moiety, PEG is a polyethylene glycol, and AA is an amino acid residue, wherein each w is an integer from 1 to 20, each n is an integer from 1 to 30, each p is an integer from 1 to 20, and each m is an integer from 1 to 12;

$V^5$, $V^6$, $V^7$ and $V^8$ are each independently selected from the group consisting of a covalent bond, —CO—, —NR$^{15}$—, —NR$^{15}$(CH$_2$)$_q$—, —NR$^{15}$ (C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein each q is an integer from 1 to 6;

each $R^{13}$ is independently selected from hydrogen, an alkyl, a substituted alkyl, an aryl, and a substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

9. The conjugate of claim 7, wherein:

$T^1$ is selected from a ($C_1$-$C_{12}$)alkyl and a substituted ($C_1$-$C_{12}$)alkyl;

$T^2$, $T^3$, and $T^4$ are each independently selected from (EDA)$_w$, (PEG)$_n$, ($C_1$-$C_{12}$)alkyl, substituted ($C_1$-$C_{12}$)

alkyl, $(AA)_p$, $-(CR^{13}OH)_m-$, 4-amino-piperidine (4AP), an acetal group, a hydrazine, and an ester; and $V^1$, $V^2$, $V^3$ and $V^4$ are each independently selected from the group consisting of a covalent bond, $-CO-$, $-NR^{15}$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$, and $-P(O)OH-$;

wherein:

$(PEG)_n$ is

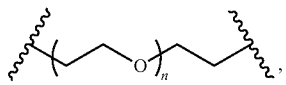

where n is an integer from 1 to 30;

EDA is an ethylene diamine moiety having the following structure:

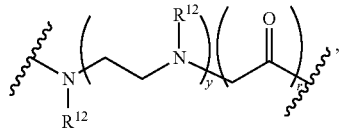

where y is an integer from 1 to 6 and r is 0 or 1;

4-amino-piperidine (4AP) is

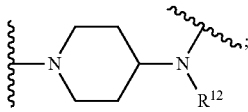

each $R^{12}$ and $R^{15}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

10. The conjugate of claim 7, wherein:

$T^1$ is $(C_1$-$C_{12})$alkyl and $V^1$ is $-CO-$;

$T^2$ is 4AP and $V^2$ is a covalent bond;

$T^3$ is $(PEG)_n$ and $V^3$ is $-CONR^{15}-$; and $T^4$ is $(C_1$-$C_{12})$alkyl and $V^4$ is $-CO-$.

11. The conjugate of claim 1, wherein the drug is an auristatin.

12. The conjugate of claim 1, wherein the drug is a maytansine.

13. A pharmaceutical composition comprising:

a conjugate of claim 1; and a pharmaceutically-acceptable excipient.

14. A method comprising:

administering to a subject an effective amount of a conjugate of claim 1.

15. A method of treating cancer in a subject, the method comprising:

administering to the subject a therapeutically effective amount of a pharmaceutical composition comprising a conjugate of claim 1, wherein the administering is effective to treat cancer in the subject.

* * * * *

UNITED STATES PATENT AND TRADEMARK OFFICE
CERTIFICATE OF CORRECTION

PATENT NO. : 11,980,668 B2
APPLICATION NO. : 17/287792
DATED : May 14, 2024
INVENTOR(S) : Rabuka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

Signed and Sealed this
Eighth Day of October, 2024

Katherine Kelly Vidal
*Director of the United States Patent and Trademark Office*